United States Patent
Lim et al.

(10) Patent No.: US 8,852,956 B2
(45) Date of Patent: Oct. 7, 2014

(54) METHOD FOR DIAGNOSING PRIMARY BILIARY CIRRHOSIS (PBC) USING NOVEL AUTOANTIGENS

(75) Inventors: Mark J. Lim, Reading, MA (US); Heather P. Ostendorf, Framingham, MA (US); Kenneth J. Rothschild, Newton, MA (US); Donald B. Bloch, Newton, MA (US)

(73) Assignees: Ambergen, Inc., Watertown, MA (US); Massachusetts General Hospital, Boston, MA (US)

( * ) Notice: Subject to any disclaimer, the term of this patent is extended or adjusted under 35 U.S.C. 154(b) by 0 days.

(21) Appl. No.: 13/500,411

(22) PCT Filed: Oct. 5, 2010

(86) PCT No.: PCT/US2010/051475
§ 371 (c)(1),
(2), (4) Date: Jun. 8, 2012

(87) PCT Pub. No.: WO2011/044125
PCT Pub. Date: Apr. 14, 2011

(65) Prior Publication Data
US 2012/0244562 A1 Sep. 27, 2012

Related U.S. Application Data

(60) Provisional application No. 61/248,768, filed on Oct. 5, 2009.

(51) Int. Cl.
*G01N 33/564* (2006.01)
*G01N 33/543* (2006.01)

(52) U.S. Cl.
USPC ............................ 436/518; 436/501; 435/7.94

(58) Field of Classification Search
None
See application file for complete search history.

(56) References Cited

U.S. PATENT DOCUMENTS 5,891,436 A 4/1999 Coppel et al.
2009/0047689 A1* 2/2009 Kolman et al. ............ 435/7.23

OTHER PUBLICATIONS

Colman et al., Res Immunol. Jan. 1994;145(1):33-6.*
Lerner et al., Nature 1982; 299:592-596, see p. 595-596.*
Mathupala et al.: 'Hexokinase-2 bound to mitochondria: Cancer's stygian link to the Warburg effect and a pivotal target for effective therapy.' Semin Cancer Biol, vol, 19, No. 1. Feb. 2009 pp. 17-24.
Uchida et al: 'Identification of specific autoantigens in Sjogren's syndrome by SEREX.' Immunology, vol. 116, No. 1, 2005, pp. 53-63.
Watt et al.: 'Patterns of autoimmunity in primary binary cirrhosis patients and their families: a population-based cohort study.' QJM. vol. 97, No. 7, 2004, pp. 397-406.
HUGO_Kelch-like family, Nov. 13, 2012 [online]. [Retrieved on Nov. 12, 2012], Retrieved from the Internet: <URL: http://www.genenames.org/genefamilies/KLHL> Entire document.
Ota et al. NCBI_NP_079406.2, hexokinase domain containing 1 [*Homo sapiens*] Nov. 17, 2006 [online]. [Retrieved on Jan. 5, 2011] Retrieved from the Internet: <URL: http://www.ncbi.nlm.nih.gov/protein/33342276> The previous version of NP_079406.3 in Table VI.
Ota et al., Complete sequencing and characterization of 21,243 full-length human cDNAs, Nat. Genet. 36 (1); 40-45 (2004).
Ota et al., Supplement to Complete sequencing and characterization of 21,243 full-length human cDNAs, Nat. Genet. 36 (1); 40-45 (2004).
Lowes W, et al: "Hexokinase isoenzymes in normal and cirrhotic human liver: suppression of glucokinase in cirrhosis", Biochimica et Biophysica Acta, Jan. 8, 1998, vol. 1379, No. 1, p. 134-142, Elsevier Science Publishers, NL.
Selmi C, et al: "The enigma of primary biliary cirrhosis", Clinical Reviews in Allergy & Immunology, Apr. 2005, vol. 28, No. 2, p. 73-81.

* cited by examiner

*Primary Examiner* — Shafiqul Haq
*Assistant Examiner* — Carmencita M Belei
(74) *Attorney, Agent, or Firm* — Jones Day

(57) ABSTRACT

Methods and compositions are described for the diagnosis of primary biliary cirrhosis. Novel autoantigens are described for use in assays which employ test samples from individuals.

12 Claims, 18 Drawing Sheets

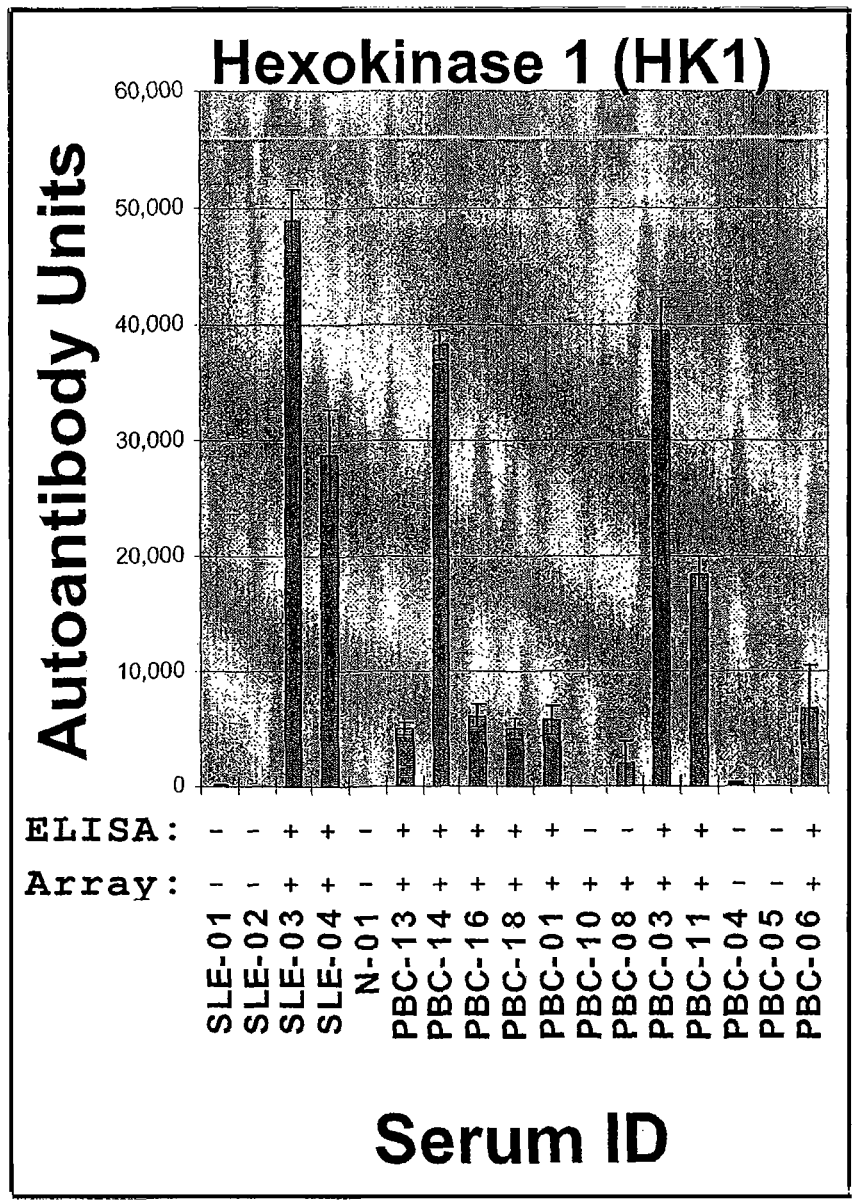
Figure 1: Pre-Validation of Hexokinase 1 (HK1) by ELISA.

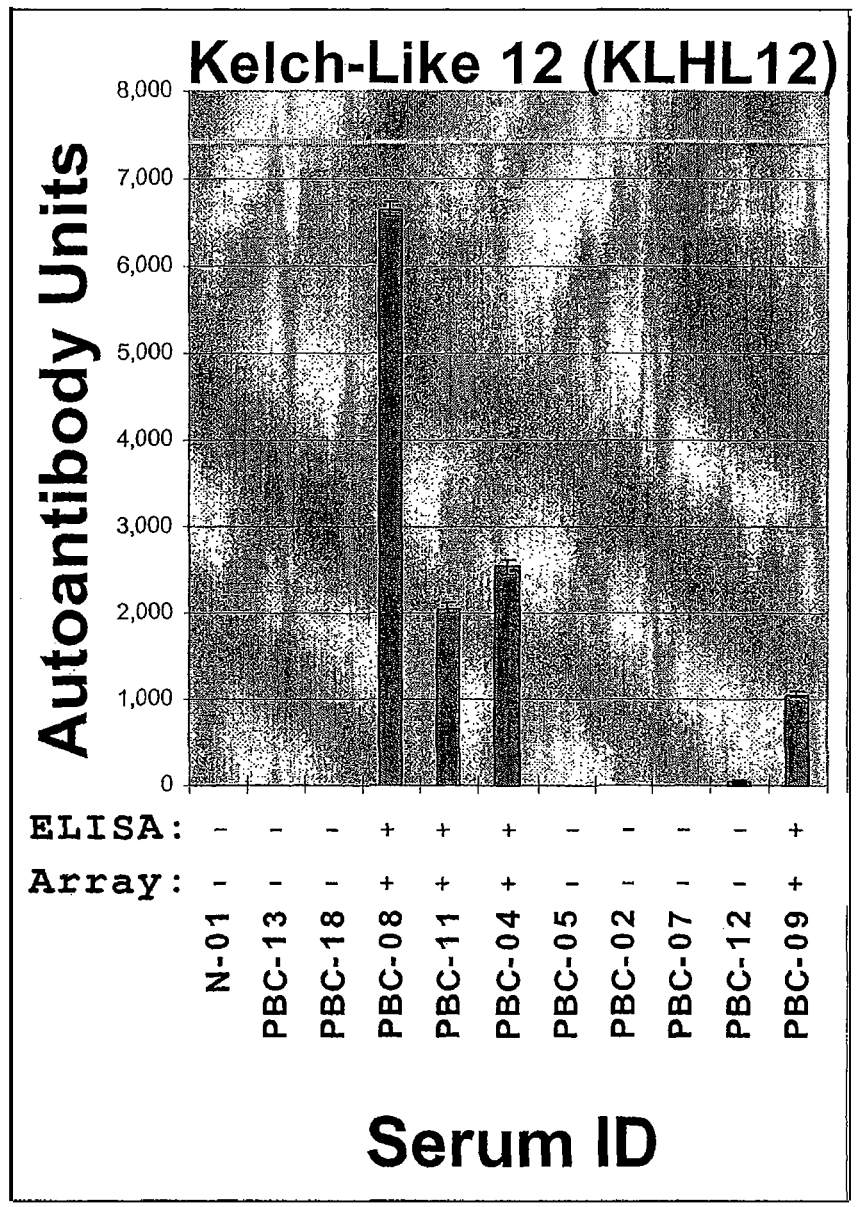
Figure 2: Pre-Validation of Kelch-Like 12 (KLHL12) by ELISA.

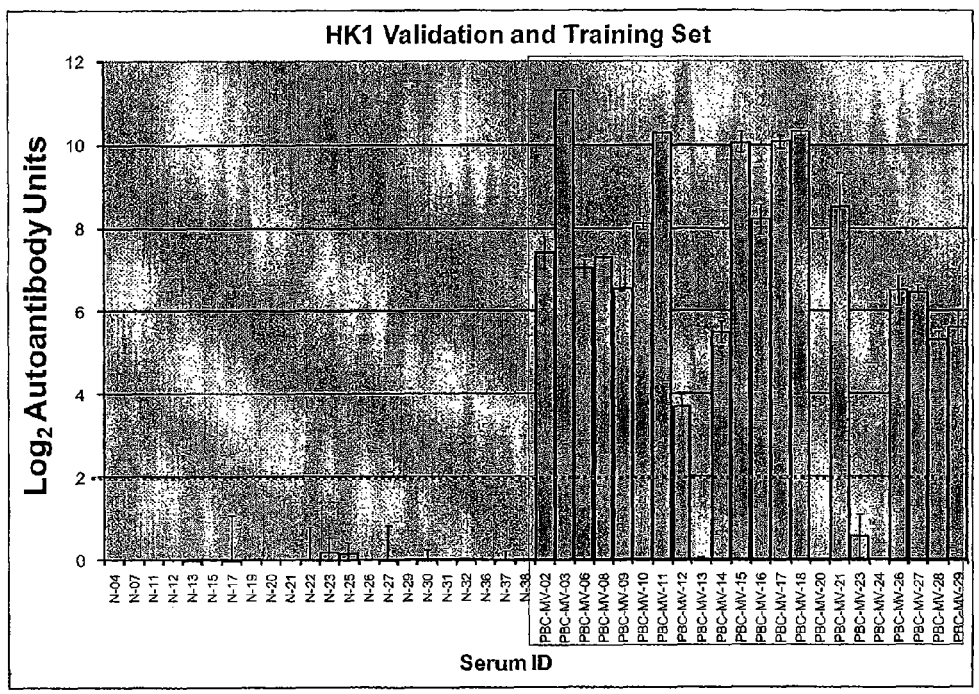
Figure 3: Validation of Hexokinase 1 (HK1) on a New PBC Patient Cohort by ELISA. Red box is the PBC patient cohort and unboxed the normal patients (82% sensitivity).

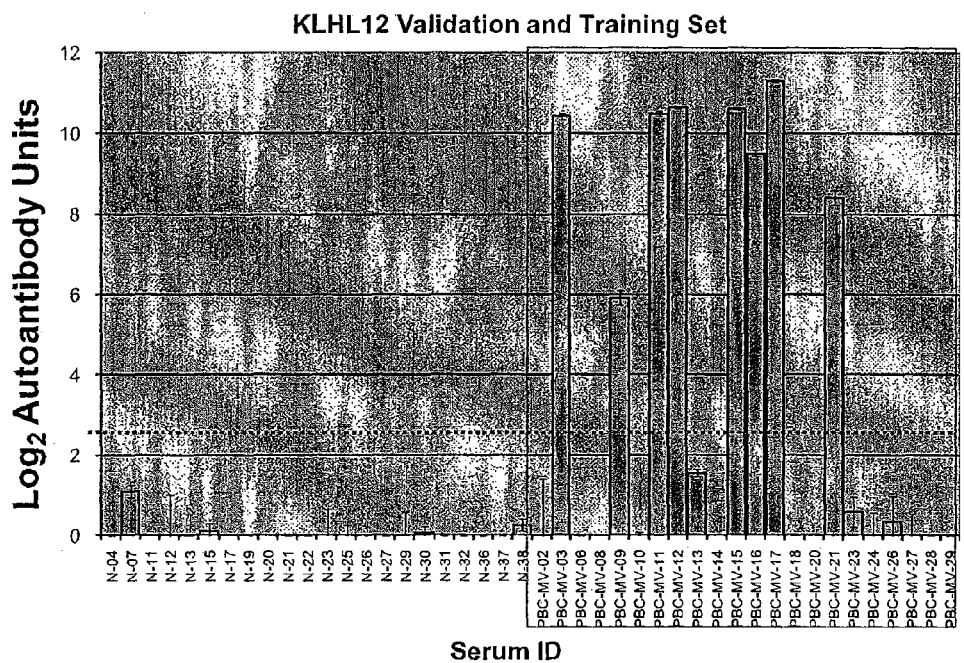
Figure 4: Validation of Kelch-Like 12 (KLHL12) on a New PBC Patient Cohort by ELISA. Red box is the PBC patient cohort and unboxed the normal patients (36% sensitivity).

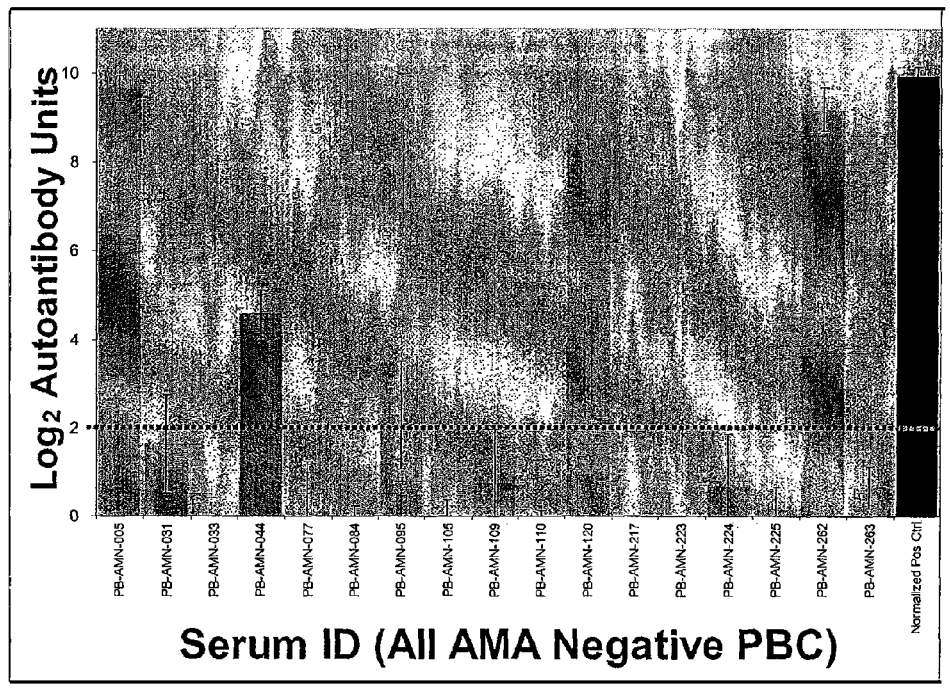
Figure 5: Hexokinase 1 (HK1) Detection on a New AMA-Negative PBC Patient Cohort by ELISA. Red line is the diagnostic threshold. HK1 detected 4 of 17 AMA-Negative PBC Patients (24% Sensitivity).

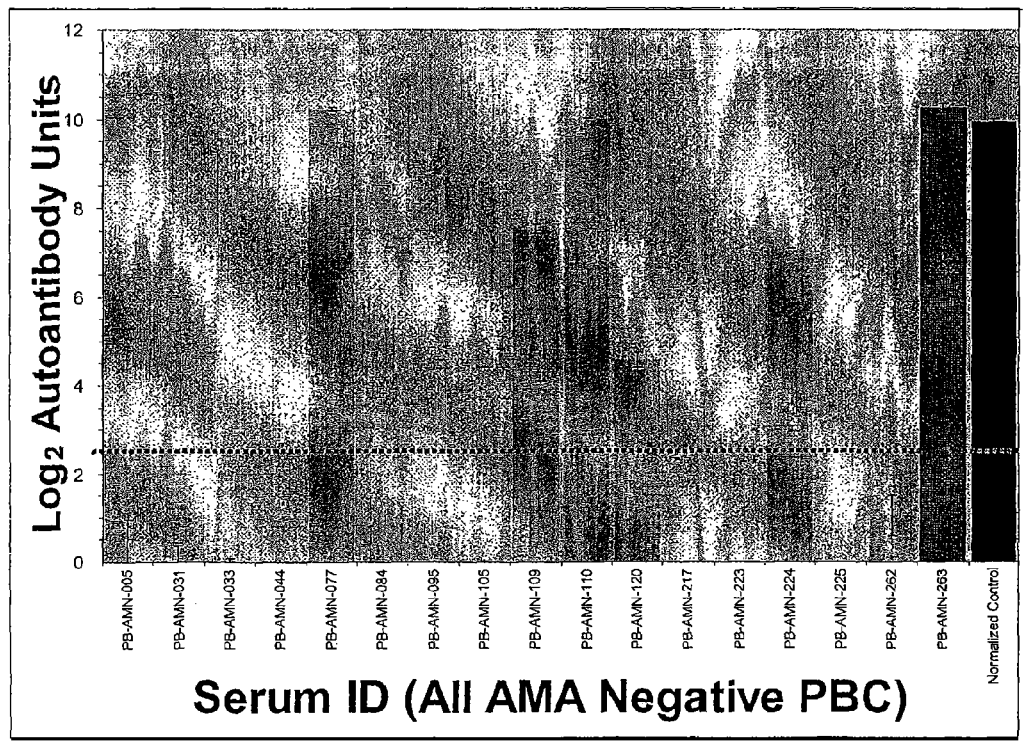
Figure 6: Kelch-like 12 (KLHL12) Detection on a New AMA-Negative PBC Patient Cohort by ELISA. Red line is the diagnostic threshold. KLHL12 detected 6 of 17 AMA-Negative PBC Patients (35% Sensitivity).

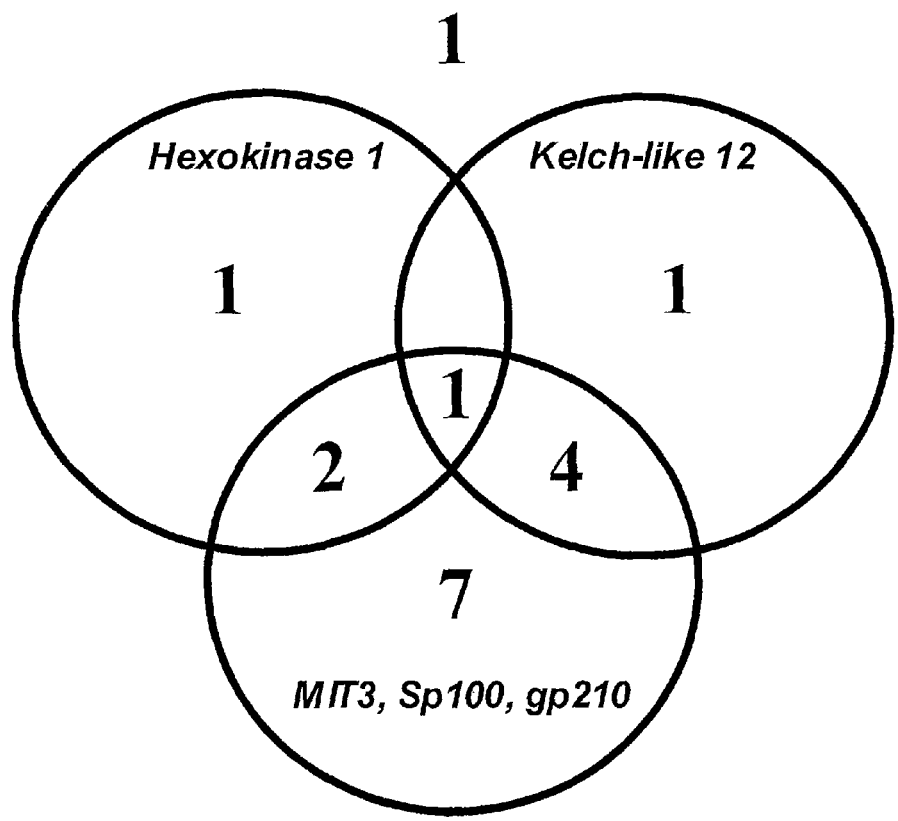
Figure 7: Venn Diagram. Novel PBC-Specific Autoantigens, HK1 and KLHL12, Capture Previously Undetectable AMA-Negative PBC Patients.

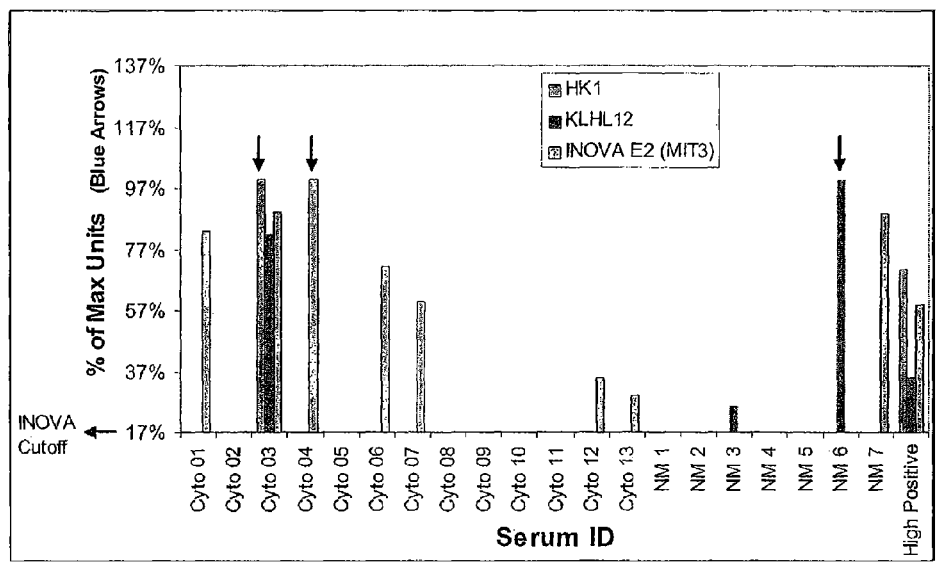
Figure 8: Detection of Hexokinase 1 (HK1) and Kelch-like 12 (KLHL12), in Addition to INOVA Diagnostic's MIT3 Assay, May Reveal a Large Number of Previously Undiagnosed PBC Patients With Atypical Indirect Immunofluorescence (IIF) Staining.

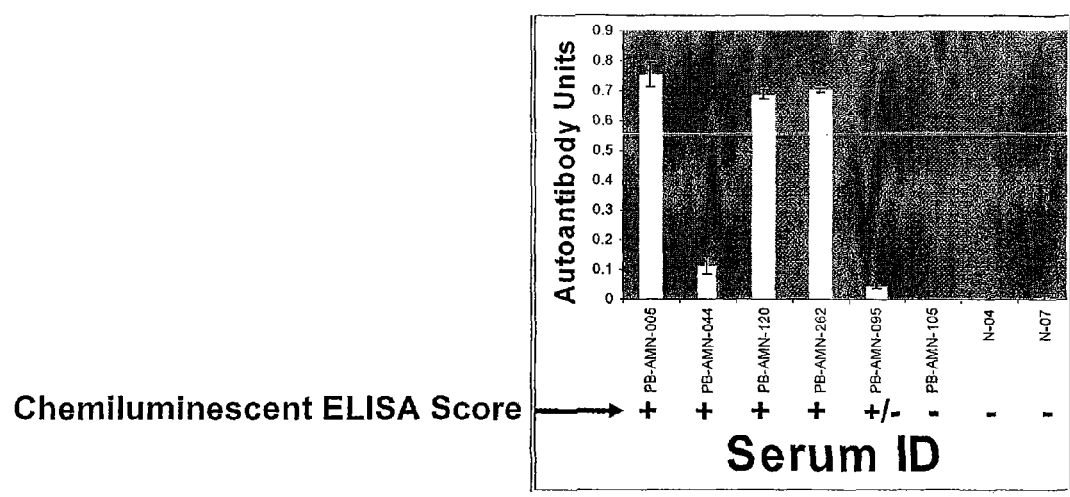
Figure 9A: HK1 Detection By Colorimetric and Chemiluminescence ELISA on Sera from PBC Patients and Normal Sera.

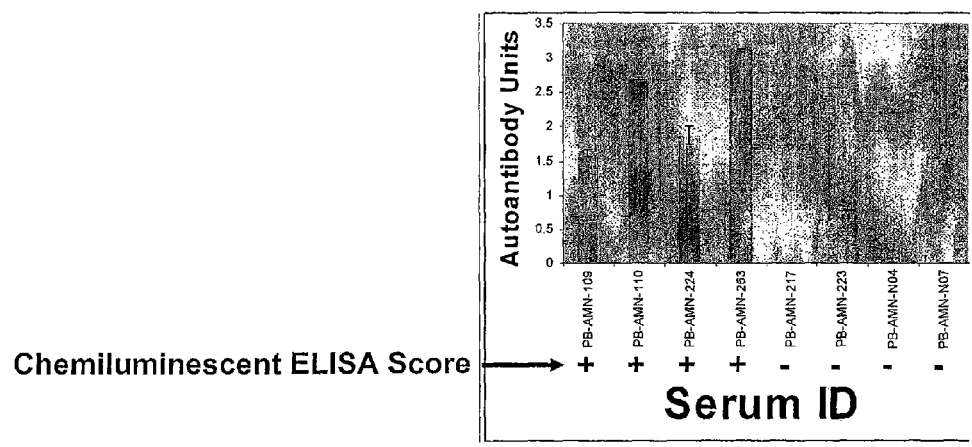
Figure 9B: KLHL12 Detection By Colorimetric and Chemiluminescence ELISA on Sera from PBC Patients and Normal Sera.

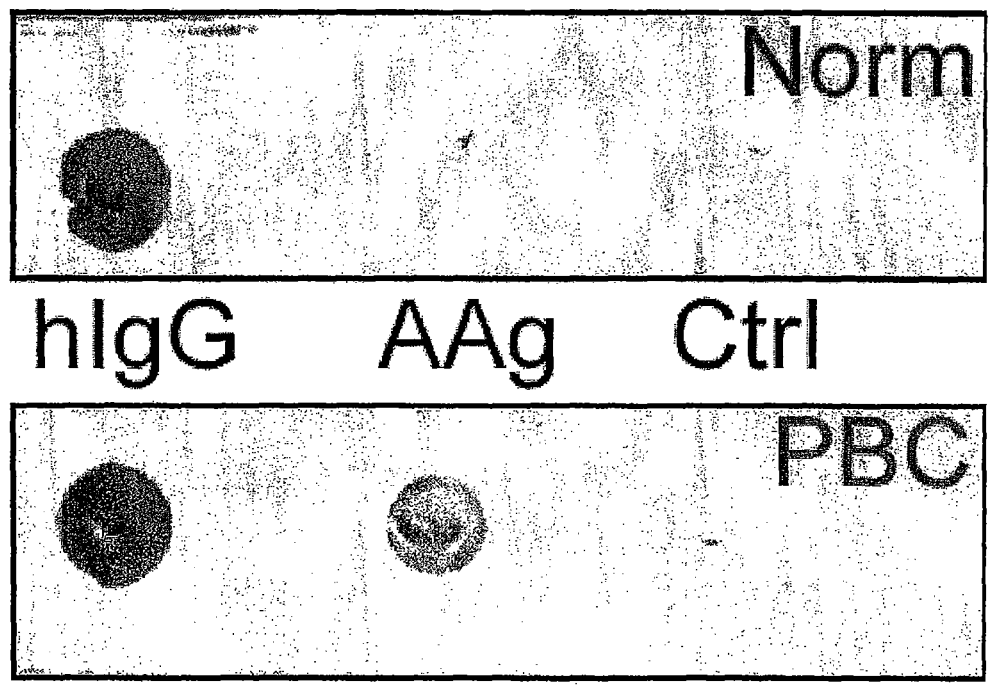
Figure 10: Colorimetric Dot Blot of PBC Autoantigen HK1 Probed with PBC and Normal Patient Sera.

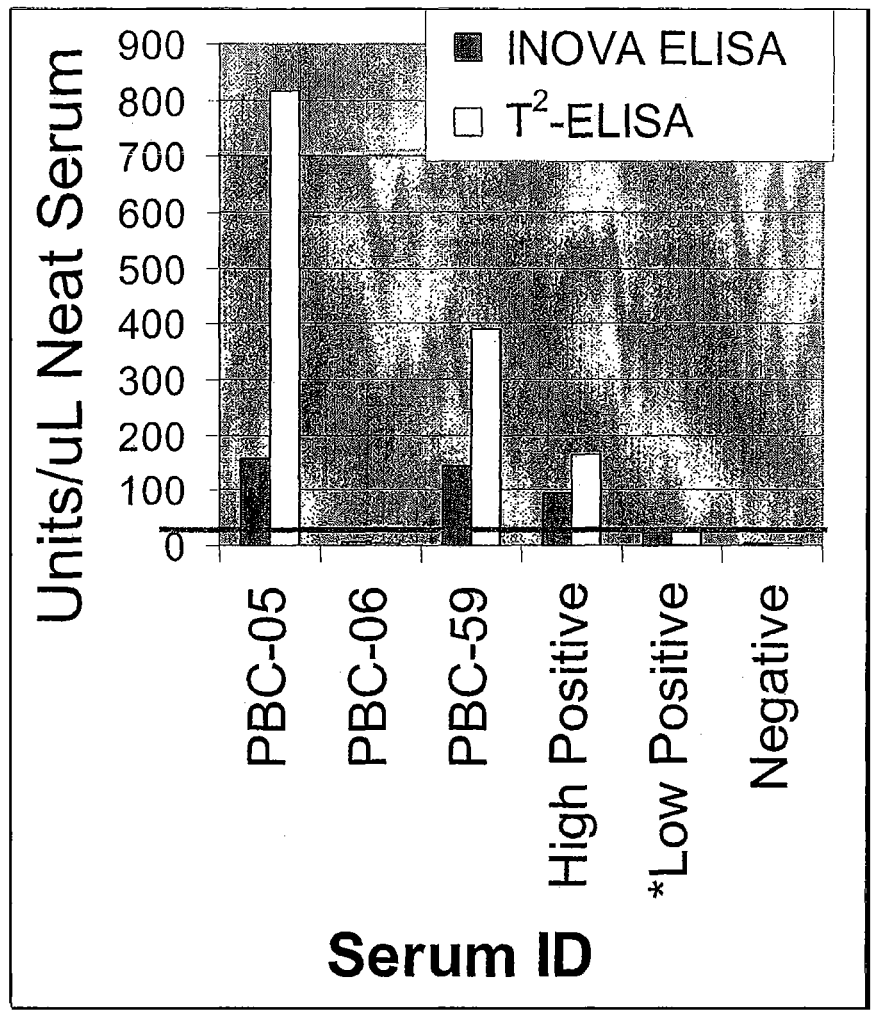
Figure 11: Comparison of $T^2$-ELISA to a Commercial ELISA (INOVA Diagnostics) Using the Sp100 Autoantigen and PBC Sera.

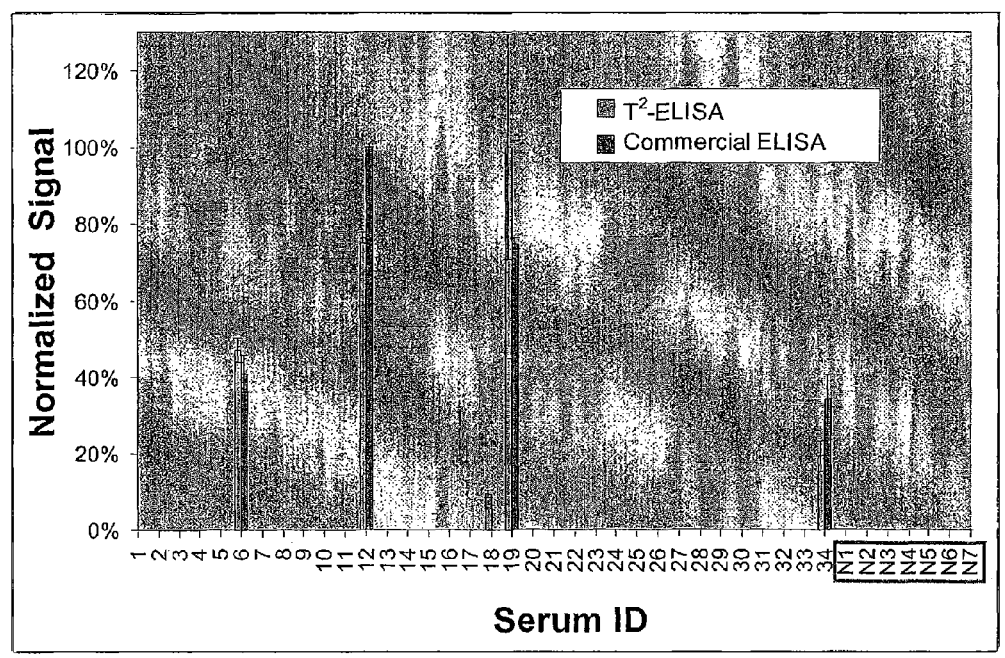
Figure 12: T²-ELISA Versus Conventional ELISA for p53 Autoantibody Detection in Cancer Sera.

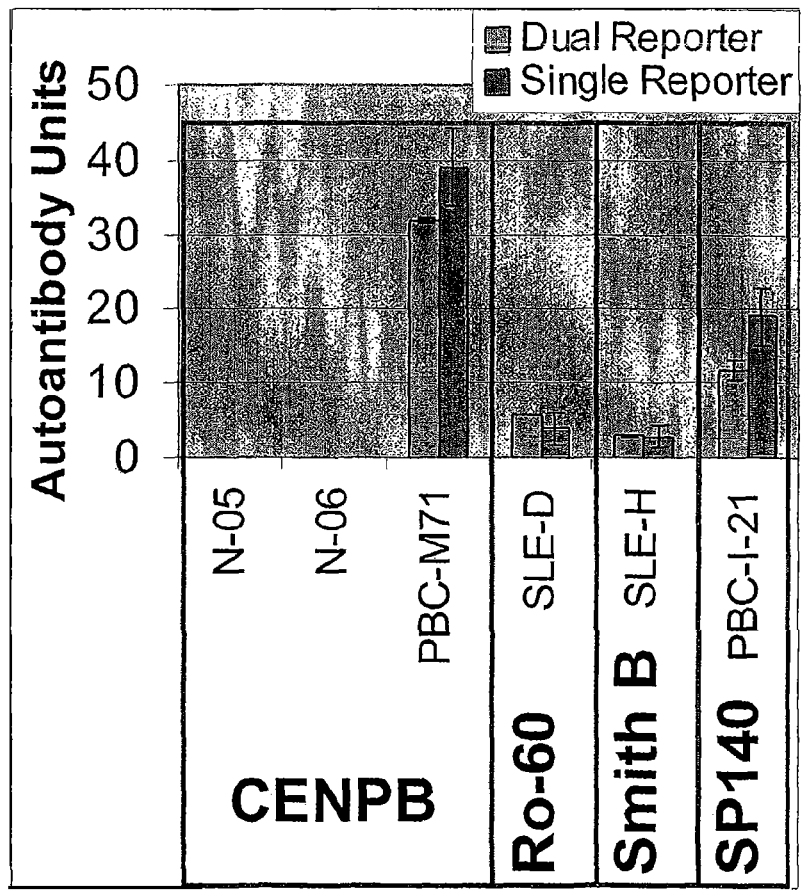
Figure 13: Dual-Reporter and Single-Reporter $T^2$-ELISA Assays Against Various Serum-Antigen Pairs.

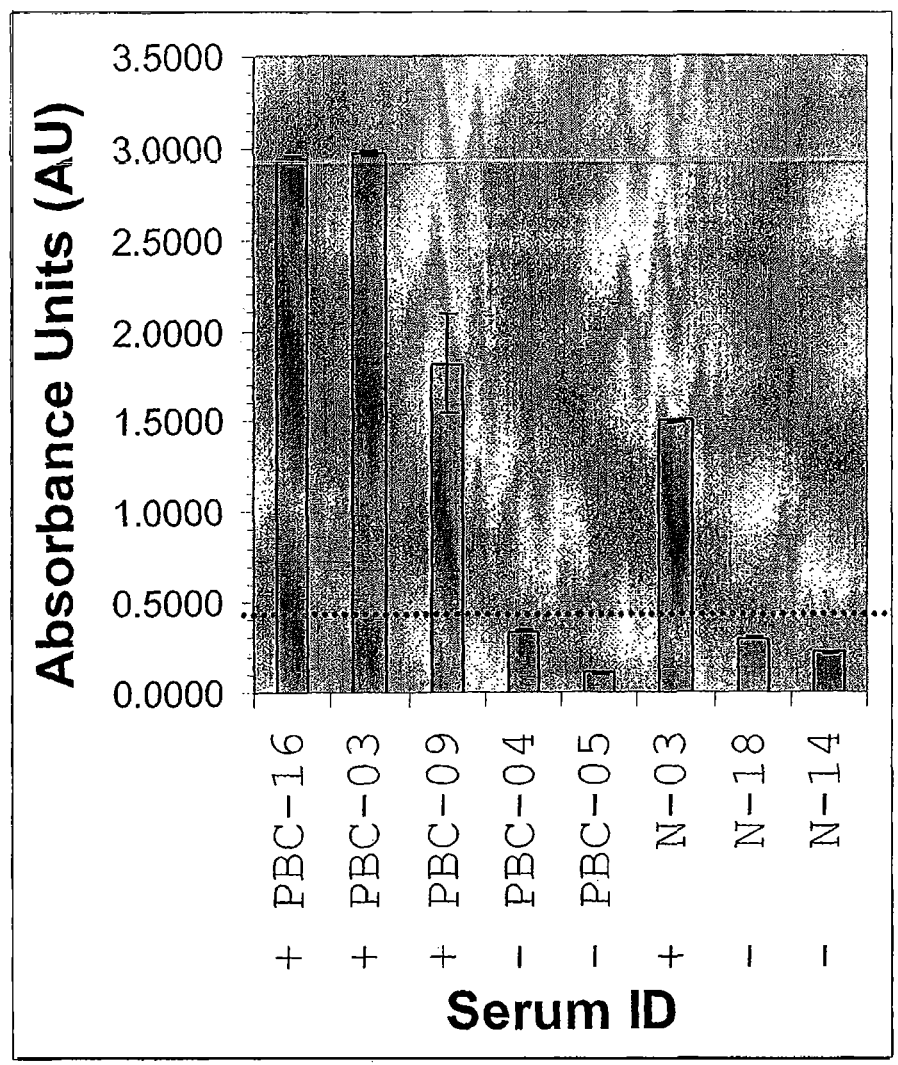
Figure 14: Autoantibody Detection in ELISA with Pre-Purified Hexokinase 1 (HK1) Coated Directly to Polystyrene Microtiter Plate Surface.

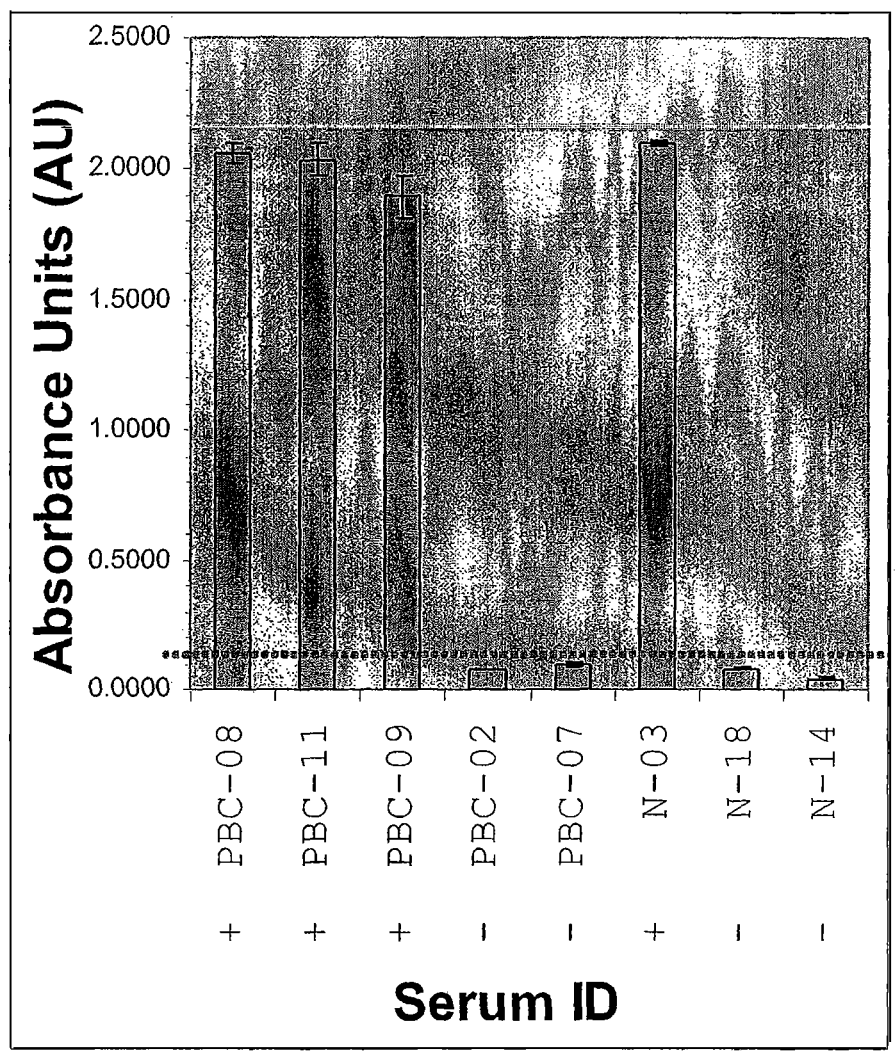
Figure 15: Autoantibody Detection in ELISA with Pre-Purified Kelch-Like 12 (KLHL12) Coated Directly to Polystyrene Microtiter Plate Surface.

Microarray Lot #1
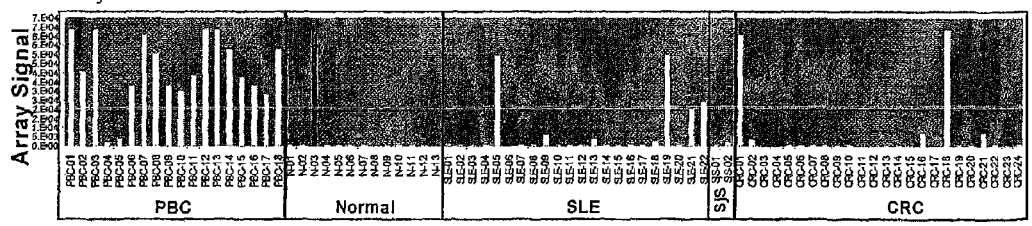
Microarray Lot #2
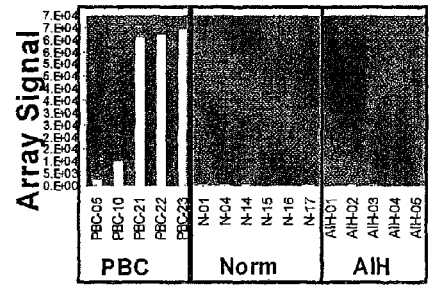
Figure 16: Quantile Normalized Proteome Microarray (ProtoArray) Autoantibody Data for Human Hexokinase 1 (HK1) for 92 Distinct Serum Samples.

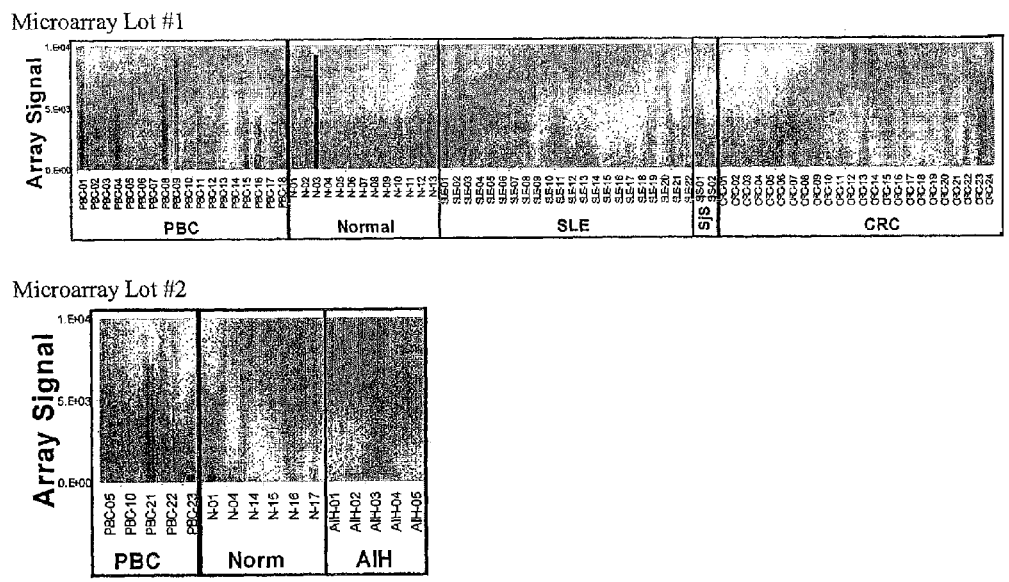
Figure 17: Quantile Normalized Proteome Microarray (ProtoArray) Autoantibody Data for Human Kelch-Like 12 (KLHL12) for 92 Distinct Serum Samples.

SEQUENCE LISTING

<160> NUMBER OF SEQ ID NOS: 20

<210> SEQ ID NO 1
<211> LENGTH: 917
<212> TYPE: PRT
<213> ORGANISM: Homo sapiens

<400> SEQUENCE: 1

```
Met Ile Ala Ala Gln Leu Leu Ala Tyr Tyr Phe Thr Glu Leu Lys Asp
1               5                   10                  15

Asp Gln Val Lys Lys Ile Asp Lys Tyr Leu Tyr Ala Met Arg Leu Ser
            20                  25                  30

Asp Glu Thr Leu Ile Asp Ile Met Thr Arg Phe Arg Lys Glu Met Lys
        35                  40                  45

Asn Gly Leu Ser Arg Asp Phe Asn Pro Thr Ala Thr Val Lys Met Leu
    50                  55                  60

Pro Thr Phe Val Arg Ser Ile Pro Asp Gly Ser Glu Lys Gly Asp Phe
65                  70                  75                  80

Ile Ala Leu Asp Leu Gly Gly Ser Ser Phe Arg Ile Leu Arg Val Gln
                85                  90                  95

Val Asn His Glu Lys Asn Gln Asn Val His Met Glu Ser Glu Val Tyr
            100                 105                 110

Asp Thr Pro Glu Asn Ile Val His Gly Ser Gly Ser Gln Leu Phe Asp
        115                 120                 125
```

-continued

```
His Val Ala Glu Cys Leu Gly Asp Phe Met Glu Lys Arg Lys Ile Lys
130                 135                 140

Asp Lys Lys Leu Pro Val Gly Phe Thr Phe Ser Phe Pro Cys Gln Gln
145                 150                 155                 160

Ser Lys Ile Asp Glu Ala Ile Leu Ile Thr Trp Thr Lys Arg Phe Lys
        165                 170                 175

Ala Ser Gly Val Glu Gly Ala Asp Val Val Lys Leu Leu Asn Lys Ala
            180                 185                 190

Ile Lys Lys Arg Gly Asp Tyr Asp Ala Asn Ile Val Ala Val Val Asn
        195                 200                 205

Asp Thr Val Gly Thr Met Met Thr Cys Gly Tyr Asp Asp Gln His Cys
210                 215                 220

Glu Val Gly Leu Ile Ile Gly Thr Gly Thr Asn Ala Cys Tyr Met Glu
225                 230                 235                 240

Glu Leu Arg His Ile Asp Leu Val Glu Gly Asp Glu Gly Arg Met Cys
                245                 250                 255

Ile Asn Thr Glu Trp Gly Ala Phe Gly Asp Asp Gly Ser Leu Glu Asp
            260                 265                 270

Ile Arg Thr Glu Phe Asp Arg Glu Ile Asp Arg Gly Ser Leu Asn Pro
        275                 280                 285

Gly Lys Gln Leu Phe Glu Lys Met Val Ser Gly Met Tyr Leu Gly Glu
290                 295                 300

Leu Val Arg Leu Ile Leu Val Lys Met Ala Lys Glu Gly Leu Leu Phe
305                 310                 315                 320

Glu Gly Arg Ile Thr Pro Glu Leu Leu Thr Arg Gly Lys Phe Asn Thr
                325                 330                 335

Ser Asp Val Ser Ala Ile Glu Lys Asn Lys Glu Gly Leu His Asn Ala
            340                 345                 350

Lys Glu Ile Leu Thr Arg Leu Gly Val Glu Pro Ser Asp Asp Asp Cys
        355                 360                 365

Val Ser Val Gln His Val Cys Thr Ile Val Ser Phe Arg Ser Ala Asn
370                 375                 380

Leu Val Ala Ala Thr Leu Gly Ala Ile Leu Asn Arg Leu Arg Asp Asn
385                 390                 395                 400

Lys Gly Thr Pro Arg Leu Arg Thr Thr Val Gly Val Asp Gly Ser Leu
                405                 410                 415

Tyr Lys Thr His Pro Gln Tyr Ser Arg Arg Phe His Lys Thr Leu Arg
            420                 425                 430

Arg Leu Val Pro Asp Ser Asp Val Arg Phe Leu Leu Ser Glu Ser Gly
        435                 440                 445

Ser Gly Lys Gly Ala Ala Met Val Thr Ala Val Ala Tyr Arg Leu Ala
450                 455                 460

Glu Gln His Arg Gln Ile Glu Glu Thr Leu Ala His Phe His Leu Thr
465                 470                 475                 480

Lys Asp Met Leu Leu Glu Val Lys Lys Arg Met Arg Ala Glu Met Glu
                485                 490                 495

Leu Gly Leu Arg Lys Gln Thr His Asn Asn Ala Val Val Lys Met Leu
            500                 505                 510

Pro Ser Phe Val Arg Arg Thr Pro Asp Gly Thr Glu Asn Gly Asp Phe
        515                 520                 525

Leu Ala Leu Asp Leu Gly Gly Thr Asn Phe Arg Val Leu Leu Val Lys
530                 535                 540
```

Ile Arg Ser Gly Lys Lys Arg Thr Val Glu Met His Asn Lys Ile Tyr
545                 550                 555                 560

Ala Ile Pro Ile Glu Ile Met Gln Gly Thr Gly Glu Glu Leu Phe Asp
            565                 570                 575

His Ile Val Ser Cys Ile Ser Asp Phe Leu Asp Tyr Met Gly Ile Lys
        580                 585                 590

Gly Pro Arg Met Pro Leu Gly Phe Thr Phe Ser Phe Pro Cys Gln Gln
    595                 600                 605

Thr Ser Leu Asp Ala Gly Ile Leu Ile Thr Trp Thr Lys Gly Phe Lys
610                 615                 620

Ala Thr Asp Cys Val Gly His Asp Val Val Thr Leu Leu Arg Asp Ala
625                 630                 635                 640

Ile Lys Arg Arg Glu Glu Phe Asp Leu Asp Val Val Ala Val Val Asn
            645                 650                 655

Asp Thr Val Gly Thr Met Met Thr Cys Ala Tyr Glu Glu Pro Thr Cys
            660                 665                 670

Glu Val Gly Leu Ile Val Gly Thr Gly Ser Asn Ala Cys Tyr Met Glu
        675                 680                 685

Glu Met Lys Asn Val Glu Met Val Glu Gly Asp Gln Gly Gln Met Cys
690                 695                 700

Ile Asn Met Glu Trp Gly Ala Phe Gly Asp Asn Gly Cys Leu Asp Asp
705                 710                 715                 720

Ile Arg Thr His Tyr Asp Arg Leu Val Asp Glu Tyr Ser Leu Asn Ala
            725                 730                 735

Gly Lys Gln Arg Tyr Glu Lys Met Ile Ser Gly Met Tyr Leu Gly Glu
            740                 745                 750

Ile Val Arg Asn Ile Leu Ile Asp Phe Thr Lys Lys Gly Phe Leu Phe
        755                 760                 765

Arg Gly Gln Ile Ser Glu Thr Leu Lys Thr Arg Gly Ile Phe Glu Thr
770                 775                 780

Lys Phe Leu Ser Gln Ile Glu Ser Asp Arg Leu Ala Leu Leu Gln Val
785                 790                 795                 800

Arg Ala Ile Leu Gln Gln Leu Gly Leu Asn Ser Thr Cys Asp Asp Ser
            805                 810                 815

Ile Leu Val Lys Thr Val Cys Gly Val Val Ser Arg Arg Ala Ala Gln
            820                 825                 830

Leu Cys Gly Ala Gly Met Ala Ala Val Val Asp Lys Ile Arg Glu Asn
        835                 840                 845

Arg Gly Leu Asp Arg Leu Asn Val Thr Val Gly Val Asp Gly Thr Leu
850                 855                 860

Tyr Lys Leu His Pro His Phe Ser Arg Ile Met His Gln Thr Val Lys
865                 870                 875                 880

Glu Leu Ser Pro Lys Cys Asn Val Ser Phe Leu Leu Ser Glu Asp Gly
            885                 890                 895

Ser Gly Lys Gly Ala Ala Leu Ile Thr Ala Val Gly Val Arg Leu Arg
            900                 905                 910

Thr Glu Ala Ser Ser
        915

<210> SEQ ID NO 2
<211> LENGTH: 568
<212> TYPE: PRT
<213> ORGANISM: Homo sapiens

<400> SEQUENCE: 2

```
Met Gly Gly Ile Met Ala Pro Lys Asp Ile Met Thr Asn Thr His Ala
1               5                   10                  15

Lys Ser Ile Leu Asn Ser Met Asn Ser Leu Arg Lys Ser Asn Thr Leu
            20                  25                  30

Cys Asp Val Thr Leu Arg Val Glu Gln Lys Asp Phe Pro Ala His Arg
            35                  40                  45

Ile Val Leu Ala Ala Cys Ser Asp Tyr Phe Cys Ala Met Phe Thr Ser
        50                  55                  60

Glu Leu Ser Glu Lys Gly Lys Pro Tyr Val Asp Ile Gln Gly Leu Thr
65                  70                  75                  80

Ala Ser Thr Met Glu Ile Leu Leu Asp Phe Val Tyr Thr Glu Thr Val
                85                  90                  95

His Val Thr Val Glu Asn Val Gln Glu Leu Leu Pro Ala Ala Cys Leu
                100                 105                 110

Leu Gln Leu Lys Gly Val Lys Gln Ala Cys Cys Glu Phe Leu Glu Ser
        115                 120                 125

Gln Leu Asp Pro Ser Asn Cys Leu Gly Ile Arg Asp Phe Ala Glu Thr
130                 135                 140

His Asn Cys Val Asp Leu Met Gln Ala Ala Glu Val Phe Ser Gln Lys
145                 150                 155                 160

His Phe Pro Glu Val Val Gln His Glu Glu Phe Ile Leu Leu Ser Gln
                165                 170                 175

Gly Glu Val Glu Lys Leu Ile Lys Cys Asp Glu Ile Gln Val Asp Ser
                180                 185                 190

Glu Glu Pro Val Phe Glu Ala Val Ile Asn Trp Val Lys His Ala Lys
                195                 200                 205

Lys Glu Arg Glu Glu Ser Leu Pro Asn Leu Leu Gln Tyr Val Arg Met
210                 215                 220

Pro Leu Leu Thr Pro Arg Tyr Ile Thr Asp Val Ile Asp Ala Glu Pro
225                 230                 235                 240

Phe Ile Arg Cys Ser Leu Gln Cys Arg Asp Leu Val Asp Glu Ala Lys
                245                 250                 255

Lys Phe His Leu Arg Pro Glu Leu Arg Ser Gln Met Gln Gly Pro Arg
                260                 265                 270

Thr Arg Ala Arg Leu Gly Ala Asn Glu Val Leu Leu Val Val Gly Gly
        275                 280                 285

Phe Gly Ser Gln Gln Ser Pro Ile Asp Val Val Glu Lys Tyr Asp Pro
        290                 295                 300

Lys Thr Gln Glu Trp Ser Phe Leu Pro Ser Ile Thr Arg Lys Arg Arg
305                 310                 315                 320

Tyr Val Ala Ser Val Ser Leu His Asp Arg Ile Tyr Val Ile Gly Gly
                325                 330                 335

Tyr Asp Gly Arg Ser Arg Leu Ser Ser Val Glu Cys Leu Asp Tyr Thr
                340                 345                 350

Ala Asp Glu Asp Gly Val Trp Tyr Ser Val Ala Pro Met Asn Val Arg
                355                 360                 365

Arg Gly Leu Ala Gly Ala Thr Thr Leu Gly Asp Met Ile Tyr Val Ser
        370                 375                 380

Gly Gly Phe Asp Gly Ser Arg Arg His Thr Ser Met Glu Arg Tyr Asp
385                 390                 395                 400

Pro Asn Ile Asp Gln Trp Ser Met Leu Gly Asp Met Gln Thr Ala Arg
                405                 410                 415
```

```
Glu Gly Ala Gly Leu Val Val Ala Ser Gly Val Ile Tyr Cys Leu Gly
                420                 425                 430

Gly Tyr Asp Gly Leu Asn Ile Leu Asn Ser Val Glu Lys Tyr Asp Pro
            435                 440                 445

His Thr Gly His Trp Thr Asn Val Thr Pro Met Ala Thr Lys Arg Ser
        450                 455                 460

Gly Ala Gly Val Ala Leu Leu Asn Asp His Ile Tyr Val Val Gly Gly
465                 470                 475                 480

Phe Asp Gly Thr Ala His Leu Ser Ser Val Glu Ala Tyr Asn Ile Arg
                485                 490                 495

Thr Asp Ser Trp Thr Thr Val Thr Ser Met Thr Thr Pro Arg Cys Tyr
            500                 505                 510

Val Gly Ala Thr Val Leu Arg Gly Arg Leu Tyr Ala Ile Ala Gly Tyr
        515                 520                 525

Asp Gly Asn Ser Leu Leu Ser Ser Ile Glu Cys Tyr Asp Pro Ile Ile
530                 535                 540

Asp Ser Trp Glu Val Val Thr Ser Met Gly Thr Gln Arg Cys Asp Ala
545                 550                 555                 560

Gly Val Cys Val Leu Arg Glu Lys
                565

<210> SEQ ID NO 3
<211> LENGTH: 988
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: The residues in these positions are exogenously
      added N-terminal and C-terminal epitope tags as well as vector-
      derived sequences.
<220> FEATURE:
<221> NAME/KEY: MISC_FEATURE
<222> LOCATION: (932)..(988)
<223> OTHER INFORMATION: The residues in these positions are exogenously
      added N-terminal and C-terminal epitope tags as well as vector-
      derived sequences.

<400> SEQUENCE: 3

Met Ala Ile Tyr Thr Asp Ile Glu Met Asn Arg Leu Gly Lys Met Ile
1               5                   10                  15

Ala Ala Gln Leu Leu Ala Tyr Tyr Phe Thr Glu Leu Lys Asp Asp Gln
                20                  25                  30

Val Lys Lys Ile Asp Lys Tyr Leu Tyr Ala Met Arg Leu Ser Asp Glu
            35                  40                  45

Thr Leu Ile Asp Ile Met Thr Arg Phe Arg Lys Glu Met Lys Asn Gly
50                  55                  60

Leu Ser Arg Asp Phe Asn Pro Thr Ala Thr Val Lys Met Leu Pro Thr
65                  70                  75                  80

Phe Val Arg Ser Ile Pro Asp Gly Ser Glu Lys Gly Asp Phe Ile Ala
                85                  90                  95

Leu Asp Leu Gly Gly Ser Ser Phe Arg Ile Leu Arg Val Gln Val Asn
            100                 105                 110

His Glu Lys Asn Gln Asn Val His Met Glu Ser Glu Val Tyr Asp Thr
        115                 120                 125

Pro Glu Asn Ile Val His Gly Ser Gly Ser Gln Leu Phe Asp His Val
130                 135                 140

Ala Glu Cys Leu Gly Asp Phe Met Glu Lys Arg Lys Ile Lys Asp Lys
145                 150                 155                 160
```

-continued

Lys Leu Pro Val Gly Phe Thr Phe Ser Phe Pro Cys Gln Gln Ser Lys
                165                 170                 175

Ile Asp Glu Ala Ile Leu Ile Thr Trp Thr Lys Arg Phe Lys Ala Ser
            180                 185                 190

Gly Val Glu Gly Ala Asp Val Val Lys Leu Leu Asn Lys Ala Ile Lys
            195                 200                 205

Lys Arg Gly Asp Tyr Asp Ala Asn Ile Val Ala Val Asn Asp Thr
        210                 215                 220

Val Gly Thr Met Met Thr Cys Gly Tyr Asp Asp Gln His Cys Glu Val
225                 230                 235                 240

Gly Leu Ile Ile Gly Thr Gly Thr Asn Ala Cys Tyr Met Glu Glu Leu
                245                 250                 255

Arg His Ile Asp Leu Val Glu Gly Asp Glu Gly Arg Met Cys Ile Asn
            260                 265                 270

Thr Glu Trp Gly Ala Phe Gly Asp Asp Gly Ser Leu Glu Asp Ile Arg
        275                 280                 285

Thr Glu Phe Asp Arg Glu Ile Asp Arg Gly Ser Leu Asn Pro Gly Lys
        290                 295                 300

Gln Leu Phe Glu Lys Met Val Ser Gly Met Tyr Leu Gly Glu Leu Val
305                 310                 315                 320

Arg Leu Ile Leu Val Lys Met Ala Lys Glu Gly Leu Leu Phe Glu Gly
                325                 330                 335

Arg Ile Thr Pro Glu Leu Leu Thr Arg Gly Lys Phe Asn Thr Ser Asp
            340                 345                 350

Val Ser Ala Ile Glu Lys Asn Lys Glu Gly Leu His Asn Ala Lys Glu
        355                 360                 365

Ile Leu Thr Arg Leu Gly Val Glu Pro Ser Asp Asp Cys Val Ser
        370                 375                 380

Val Gln His Val Cys Thr Ile Val Ser Phe Arg Ser Ala Asn Leu Val
385                 390                 395                 400

Ala Ala Thr Leu Gly Ala Ile Leu Asn Arg Leu Arg Asp Asn Lys Gly
                405                 410                 415

Thr Pro Arg Leu Arg Thr Thr Val Gly Val Asp Gly Ser Leu Tyr Lys
            420                 425                 430

Thr His Pro Gln Tyr Ser Arg Arg Phe His Lys Thr Leu Arg Arg Leu
        435                 440                 445

Val Pro Asp Ser Asp Val Arg Phe Leu Leu Ser Glu Ser Gly Ser Gly
450                 455                 460

Lys Gly Ala Ala Met Val Thr Ala Val Ala Tyr Arg Leu Ala Glu Gln
465                 470                 475                 480

His Arg Gln Ile Glu Glu Thr Leu Ala His Phe His Leu Thr Lys Asp
                485                 490                 495

Met Leu Leu Glu Val Lys Lys Arg Met Arg Ala Glu Met Glu Leu Gly
            500                 505                 510

Leu Arg Lys Gln Thr His Asn Asn Ala Val Val Lys Met Leu Pro Ser
        515                 520                 525

Phe Val Arg Arg Thr Pro Asp Gly Thr Glu Asn Gly Asp Phe Leu Ala
        530                 535                 540

Leu Asp Leu Gly Gly Thr Asn Phe Arg Val Leu Leu Val Lys Ile Arg
545                 550                 555                 560

Ser Gly Lys Lys Arg Thr Val Glu Met His Asn Lys Ile Tyr Ala Ile
                565                 570                 575

```
Pro Ile Glu Ile Met Gln Gly Thr Gly Glu Leu Phe Asp His Ile
                580                 585                 590

Val Ser Cys Ile Ser Asp Phe Leu Asp Tyr Met Gly Ile Lys Gly Pro
        595                 600                 605

Arg Met Pro Leu Gly Phe Thr Phe Ser Phe Pro Cys Gln Gln Thr Ser
610                 615                 620

Leu Asp Ala Gly Ile Leu Ile Thr Trp Thr Lys Gly Phe Lys Ala Thr
625                 630                 635                 640

Asp Cys Val Gly His Asp Val Val Thr Leu Leu Arg Asp Ala Ile Lys
                645                 650                 655

Arg Arg Glu Glu Phe Asp Leu Asp Val Ala Val Val Asn Asp Thr
                660                 665                 670

Val Gly Thr Met Met Thr Cys Ala Tyr Glu Glu Pro Thr Cys Glu Val
        675                 680                 685

Gly Leu Ile Val Gly Thr Gly Ser Asn Ala Cys Tyr Met Glu Glu Met
        690                 695                 700

Lys Asn Val Glu Met Val Glu Gly Asp Gln Gly Gln Met Cys Ile Asn
705                 710                 715                 720

Met Glu Trp Gly Ala Phe Gly Asp Asn Gly Cys Leu Asp Asp Ile Arg
                725                 730                 735

Thr His Tyr Asp Arg Leu Val Asp Glu Tyr Ser Leu Asn Ala Gly Lys
                740                 745                 750

Gln Arg Tyr Glu Lys Met Ile Ser Gly Met Tyr Leu Gly Glu Ile Val
                755                 760                 765

Arg Asn Ile Leu Ile Asp Phe Thr Lys Lys Gly Phe Leu Phe Arg Gly
770                 775                 780

Gln Ile Ser Glu Thr Leu Lys Thr Arg Gly Ile Phe Glu Thr Lys Phe
785                 790                 795                 800

Leu Ser Gln Ile Glu Ser Asp Arg Leu Ala Leu Leu Gln Val Arg Ala
                805                 810                 815

Ile Leu Gln Gln Leu Gly Leu Asn Ser Thr Cys Asp Asp Ser Ile Leu
                820                 825                 830

Val Lys Thr Val Cys Gly Val Val Ser Arg Arg Ala Ala Gln Leu Cys
        835                 840                 845

Gly Ala Gly Met Ala Ala Val Val Asp Lys Ile Arg Glu Asn Arg Gly
850                 855                 860

Leu Asp Arg Leu Asn Val Thr Val Gly Val Asp Gly Thr Leu Tyr Lys
865                 870                 875                 880

Leu His Pro His Phe Ser Arg Ile Met His Gln Thr Val Lys Glu Leu
                885                 890                 895

Ser Pro Lys Cys Asn Val Ser Phe Leu Leu Ser Glu Asp Gly Ser Gly
                900                 905                 910

Lys Gly Ala Ala Leu Ile Thr Ala Val Gly Val Arg Leu Arg Thr Glu
        915                 920                 925

Ala Ser Ser Leu Ser Arg Glu Leu Val Asp Pro Asn Ser Val Gln Ala
        930                 935                 940

Arg Leu Gln Asp Val Asp Gly Thr Ile Asp Thr Arg Ser Lys Leu Ala
945                 950                 955                 960

Ala Ala Gln Leu Tyr Thr Arg Ala Ser Gln Pro Glu Leu Ala Pro Glu
                965                 970                 975

Asp Pro Glu Asp Leu Glu His His His His His
                980                 985
```

-continued

```
<210> SEQ ID NO 4
<211> LENGTH: 591
<212> TYPE: PRT
<213> ORGANISM: Homo sapiens

<400> SEQUENCE: 4
```

Met Tyr Thr Asp Ile Glu Met Asn Arg Leu Gly Lys Met Gly Gly Ile
1               5                   10                  15

Met Ala Pro Lys Asp Ile Met Thr Asn Thr His Ala Lys Ser Ile Leu
            20                  25                  30

Asn Ser Met Asn Ser Leu Arg Lys Ser Asn Thr Leu Cys Asp Val Thr
        35                  40                  45

Leu Arg Val Glu Gln Lys Asp Phe Pro Ala His Arg Ile Val Leu Ala
    50                  55                  60

Ala Cys Ser Asp Tyr Phe Cys Ala Met Phe Thr Ser Glu Leu Ser Glu
65                  70                  75                  80

Lys Gly Lys Pro Tyr Val Asp Ile Gln Gly Leu Thr Ala Ser Thr Met
                85                  90                  95

Glu Ile Leu Leu Asp Phe Val Tyr Thr Glu Thr Val His Val Thr Val
            100                 105                 110

Glu Asn Val Gln Glu Leu Leu Pro Ala Ala Cys Leu Leu Gln Leu Lys
        115                 120                 125

Gly Val Lys Gln Ala Cys Cys Glu Phe Leu Glu Ser Gln Leu Asp Pro
    130                 135                 140

Ser Asn Cys Leu Gly Ile Arg Asp Phe Ala Glu Thr His Asn Cys Val
145                 150                 155                 160

Asp Leu Met Gln Ala Ala Glu Val Phe Ser Gln Lys His Phe Pro Glu
                165                 170                 175

Val Val Gln His Glu Glu Phe Ile Leu Leu Ser Gln Gly Glu Val Glu
            180                 185                 190

Lys Leu Ile Lys Cys Asp Glu Ile Gln Val Asp Ser Glu Pro Val
        195                 200                 205

Phe Glu Ala Val Ile Asn Trp Val Lys His Ala Lys Lys Glu Arg Glu
    210                 215                 220

Glu Ser Leu Pro Asn Leu Leu Gln Tyr Val Arg Met Pro Leu Leu Thr
225                 230                 235                 240

Pro Arg Tyr Ile Thr Asp Val Ile Asp Ala Glu Pro Phe Ile Arg Cys
                245                 250                 255

Ser Leu Gln Cys Arg Asp Leu Val Asp Glu Ala Lys Lys Phe His Leu
            260                 265                 270

Arg Pro Glu Leu Arg Ser Gln Met Gln Gly Pro Arg Thr Arg Ala Arg
        275                 280                 285

Leu Gly Ala Asn Glu Val Leu Leu Val Val Gly Gly Phe Gly Ser Gln
    290                 295                 300

Gln Ser Pro Ile Asp Val Val Glu Lys Tyr Asp Pro Lys Thr Gln Glu
305                 310                 315                 320

Trp Ser Phe Leu Pro Ser Ile Thr Arg Lys Arg Tyr Val Ala Ser
                325                 330                 335

Val Ser Leu His Asp Arg Ile Tyr Val Ile Gly Gly Tyr Asp Gly Arg
            340                 345                 350

Ser Arg Leu Ser Ser Val Glu Cys Leu Asp Tyr Thr Ala Asp Glu Asp
        355                 360                 365

Gly Val Trp Tyr Ser Val Ala Pro Met Asn Val Arg Arg Gly Leu Ala
    370                 375                 380

```
Gly Ala Thr Thr Leu Gly Asp Met Ile Tyr Val Ser Gly Gly Phe Asp
385                 390                 395                 400

Gly Ser Arg Arg His Thr Ser Met Glu Arg Tyr Asp Pro Asn Ile Asp
            405                 410                 415

Gln Trp Ser Met Leu Gly Asp Met Gln Thr Ala Arg Glu Gly Ala Gly
        420                 425                 430

Leu Val Val Ala Ser Gly Val Ile Tyr Cys Leu Gly Tyr Asp Gly
        435                 440                 445

Leu Asn Ile Leu Asn Ser Val Glu Lys Tyr Asp Pro His Thr Gly His
    450                 455                 460

Trp Thr Asn Val Thr Pro Met Ala Thr Lys Arg Ser Gly Ala Gly Val
465                 470                 475                 480

Ala Leu Leu Asn Asp His Ile Tyr Val Val Gly Gly Phe Asp Gly
            485                 490                 495

Ala His Leu Ser Ser Val Glu Ala Tyr Asn Ile Arg Thr Asp Ser Trp
            500                 505                 510

Thr Thr Val Thr Ser Met Thr Thr Pro Arg Cys Tyr Val Gly Ala Thr
            515                 520                 525

Val Leu Arg Gly Arg Leu Tyr Ala Ile Ala Gly Tyr Asp Gly Asn Ser
530                 535                 540

Leu Leu Ser Ser Ile Glu Cys Tyr Asp Pro Ile Ile Asp Ser Trp Glu
545                 550                 555                 560

Val Val Thr Ser Met Gly Thr Gln Arg Cys Asp Ala Gly Val Cys Val
                565                 570                 575

Leu Arg Glu Lys Gln Pro Glu Leu Ala Pro Glu Asp Pro Glu Asp
        580                 585                 590

<210> SEQ ID NO 5
<211> LENGTH: 917
<212> TYPE: PRT
<213> ORGANISM: Homo sapiens

<400> SEQUENCE: 5

Met Ile Ala Ala Gln Leu Leu Ala Tyr Tyr Phe Thr Glu Leu Lys Asp
1               5                   10                  15

Asp Gln Val Lys Lys Ile Asp Lys Tyr Leu Tyr Ala Met Arg Leu Ser
            20                  25                  30

Asp Glu Thr Leu Ile Asp Ile Met Thr Arg Phe Arg Lys Glu Met Lys
        35                  40                  45

Asn Gly Leu Ser Arg Asp Phe Asn Pro Thr Ala Thr Val Lys Met Leu
    50                  55                  60

Pro Thr Phe Val Arg Ser Ile Pro Asp Gly Ser Glu Lys Gly Asp Phe
65                  70                  75                  80

Ile Ala Leu Asp Leu Gly Gly Ser Ser Phe Arg Ile Leu Arg Val Gln
                85                  90                  95

Val Asn His Glu Lys Asn Gln Asn Val His Met Glu Ser Glu Val Tyr
            100                 105                 110

Asp Thr Pro Glu Asn Ile Val His Gly Ser Gly Ser Gln Leu Phe Asp
        115                 120                 125

His Val Ala Glu Cys Leu Gly Asp Phe Met Glu Lys Arg Lys Ile Lys
    130                 135                 140

Asp Lys Lys Leu Pro Val Gly Phe Thr Phe Ser Phe Pro Cys Gln Gln
145                 150                 155                 160

Ser Lys Ile Asp Glu Ala Ile Leu Ile Thr Trp Thr Lys Arg Phe Lys
                165                 170                 175
```

```
Ala Ser Gly Val Glu Gly Ala Asp Val Val Lys Leu Leu Asn Lys Ala
            180                 185                 190

Ile Lys Lys Arg Gly Asp Tyr Asp Ala Asn Ile Val Ala Val Val Asn
        195                 200                 205

Asp Thr Val Gly Thr Met Met Thr Cys Gly Tyr Asp Asp Gln His Cys
    210                 215                 220

Glu Val Gly Leu Ile Ile Gly Thr Gly Thr Asn Ala Cys Tyr Met Glu
225                 230                 235                 240

Glu Leu Arg His Ile Asp Leu Val Glu Gly Asp Glu Gly Arg Met Cys
                245                 250                 255

Ile Asn Thr Glu Trp Gly Ala Phe Gly Asp Asp Gly Ser Leu Glu Asp
            260                 265                 270

Ile Arg Thr Glu Phe Asp Arg Glu Ile Asp Arg Gly Ser Leu Asn Pro
        275                 280                 285

Gly Lys Gln Leu Phe Glu Lys Met Val Ser Gly Met Tyr Leu Gly Glu
    290                 295                 300

Leu Val Arg Leu Ile Leu Val Lys Met Ala Lys Glu Gly Leu Leu Phe
305                 310                 315                 320

Glu Gly Arg Ile Thr Pro Glu Leu Leu Thr Arg Gly Lys Phe Asn Thr
                325                 330                 335

Ser Asp Val Ser Ala Ile Glu Lys Asn Lys Glu Gly Leu His Asn Ala
            340                 345                 350

Lys Glu Ile Leu Thr Arg Leu Gly Val Glu Pro Ser Asp Asp Asp Cys
        355                 360                 365

Val Ser Val Gln His Val Cys Thr Ile Val Ser Phe Arg Ser Ala Asn
    370                 375                 380

Leu Val Ala Ala Thr Leu Gly Ala Ile Leu Asn Arg Leu Arg Asp Asn
385                 390                 395                 400

Lys Gly Thr Pro Arg Leu Arg Thr Thr Val Gly Val Asp Gly Ser Leu
                405                 410                 415

Tyr Lys Thr His Pro Gln Tyr Ser Arg Arg Phe His Lys Thr Leu Arg
            420                 425                 430

Arg Leu Val Pro Asp Ser Asp Val Arg Phe Leu Leu Ser Glu Ser Gly
        435                 440                 445

Ser Gly Lys Gly Ala Ala Met Val Thr Ala Val Ala Tyr Arg Leu Ala
    450                 455                 460

Glu Gln His Arg Gln Ile Glu Glu Thr Leu Ala His Phe His Leu Thr
465                 470                 475                 480

Lys Asp Met Leu Leu Glu Val Lys Lys Arg Met Arg Ala Glu Met Glu
                485                 490                 495

Leu Gly Leu Arg Lys Gln Thr His Asn Asn Ala Val Val Lys Met Leu
            500                 505                 510

Pro Ser Phe Val Arg Arg Thr Pro Asp Gly Thr Glu Asn Gly Asp Phe
        515                 520                 525

Leu Ala Leu Asp Leu Gly Gly Thr Asn Phe Arg Val Leu Leu Val Lys
    530                 535                 540

Ile Arg Ser Gly Lys Lys Arg Thr Val Glu Met His Asn Lys Ile Tyr
545                 550                 555                 560

Ala Ile Pro Ile Glu Ile Met Gln Gly Thr Gly Glu Glu Leu Phe Asp
                565                 570                 575

His Ile Val Ser Cys Ile Ser Asp Phe Leu Asp Tyr Met Gly Ile Lys
            580                 585                 590
```

```
Gly Pro Arg Met Pro Leu Gly Phe Thr Phe Ser Phe Pro Cys Gln Gln
            595                 600                 605

Thr Ser Leu Asp Ala Gly Ile Leu Ile Thr Trp Thr Lys Gly Phe Lys
610                 615                 620

Ala Thr Asp Cys Val Gly His Asp Val Val Thr Leu Leu Arg Asp Ala
625                 630                 635                 640

Ile Lys Arg Arg Glu Glu Phe Asp Leu Asp Val Val Ala Val Val Asn
                645                 650                 655

Asp Thr Val Gly Thr Met Met Thr Cys Ala Tyr Glu Glu Pro Thr Cys
                660                 665                 670

Glu Val Gly Leu Ile Val Gly Thr Gly Ser Asn Ala Cys Tyr Met Glu
            675                 680                 685

Glu Met Lys Asn Val Glu Met Val Glu Gly Asp Gln Gly Gln Met Cys
        690                 695                 700

Ile Asn Met Glu Trp Gly Ala Phe Gly Asp Asn Gly Cys Leu Asp Asp
705                 710                 715                 720

Ile Arg Thr His Tyr Asp Arg Leu Val Asp Glu Tyr Ser Leu Asn Ala
                725                 730                 735

Gly Lys Gln Arg Tyr Glu Lys Met Ile Ser Gly Met Tyr Leu Gly Glu
                740                 745                 750

Ile Val Arg Asn Ile Leu Ile Asp Phe Thr Lys Lys Gly Phe Leu Phe
            755                 760                 765

Arg Gly Gln Ile Ser Glu Thr Leu Lys Thr Arg Gly Ile Phe Glu Thr
        770                 775                 780

Lys Phe Leu Ser Gln Ile Glu Ser Asp Arg Leu Ala Leu Leu Gln Val
785                 790                 795                 800

Arg Ala Ile Leu Gln Gln Leu Gly Leu Asn Ser Thr Cys Asp Asp Ser
                805                 810                 815

Ile Leu Val Lys Thr Val Cys Gly Val Val Ser Arg Arg Ala Ala Gln
                820                 825                 830

Leu Cys Gly Ala Gly Met Ala Ala Val Val Asp Lys Ile Arg Glu Asn
            835                 840                 845

Arg Gly Leu Asp Arg Leu Asn Val Thr Val Gly Val Asp Gly Thr Leu
        850                 855                 860

Tyr Lys Leu His Pro His Phe Ser Arg Ile Met His Gln Thr Val Lys
865                 870                 875                 880

Glu Leu Ser Pro Lys Cys Asn Val Ser Phe Leu Leu Ser Glu Asp Gly
                885                 890                 895

Ser Gly Lys Gly Ala Ala Leu Ile Thr Ala Val Gly Val Arg Leu Arg
                900                 905                 910

Thr Glu Ala Ser Ser
            915

<210> SEQ ID NO 6
<211> LENGTH: 568
<212> TYPE: PRT
<213> ORGANISM: Homo sapiens

<400> SEQUENCE: 6

Met Gly Gly Ile Met Ala Pro Lys Asp Ile Met Thr Asn Thr His Ala
1               5                   10                  15

Lys Ser Ile Leu Asn Ser Met Asn Ser Leu Arg Lys Ser Asn Thr Leu
                20                  25                  30

Cys Asp Val Thr Leu Arg Val Glu Gln Lys Asp Phe Pro Ala His Arg
            35                  40                  45
```

```
Ile Val Leu Ala Ala Cys Ser Asp Tyr Phe Cys Ala Met Phe Thr Ser
             50              55              60

Glu Leu Ser Glu Lys Gly Lys Pro Tyr Val Asp Ile Gln Gly Leu Thr
 65              70              75              80

Ala Ser Thr Met Glu Ile Leu Leu Asp Phe Val Tyr Thr Glu Thr Val
                 85              90              95

His Val Thr Val Glu Asn Val Gln Glu Leu Leu Pro Ala Ala Cys Leu
            100             105             110

Leu Gln Leu Lys Gly Val Lys Gln Ala Cys Cys Glu Phe Leu Glu Ser
            115             120             125

Gln Leu Asp Pro Ser Asn Cys Leu Gly Ile Arg Asp Phe Ala Glu Thr
130             135             140

His Asn Cys Val Asp Leu Met Gln Ala Ala Glu Val Phe Ser Gln Lys
145             150             155             160

His Phe Pro Glu Val Val Gln His Glu Phe Ile Leu Leu Ser Gln
                165             170             175

Gly Glu Val Glu Lys Leu Ile Lys Cys Asp Glu Ile Gln Val Asp Ser
            180             185             190

Glu Glu Pro Val Phe Glu Ala Val Ile Asn Trp Val Lys His Ala Lys
            195             200             205

Lys Glu Arg Glu Glu Ser Leu Pro Asn Leu Leu Gln Tyr Val Arg Met
210             215             220

Pro Leu Leu Thr Pro Arg Tyr Ile Thr Asp Val Ile Asp Ala Glu Pro
225             230             235             240

Phe Ile Arg Cys Ser Leu Gln Cys Arg Asp Leu Val Asp Glu Ala Lys
                245             250             255

Lys Phe His Leu Arg Pro Glu Leu Arg Ser Gln Met Gly Pro Arg
            260             265             270

Thr Arg Ala Arg Leu Gly Ala Asn Glu Val Leu Leu Val Gly Gly
            275             280             285

Phe Gly Ser Gln Gln Ser Pro Ile Asp Val Val Glu Lys Tyr Asp Pro
290             295             300

Lys Thr Gln Glu Trp Ser Phe Leu Pro Ser Ile Thr Arg Lys Arg Arg
305             310             315             320

Tyr Val Ala Ser Val Ser Leu His Asp Arg Ile Tyr Val Ile Gly Gly
                325             330             335

Tyr Asp Gly Arg Ser Arg Leu Ser Ser Val Glu Cys Leu Asp Tyr Thr
            340             345             350

Ala Asp Glu Asp Gly Val Trp Tyr Ser Val Ala Pro Met Asn Val Arg
            355             360             365

Arg Gly Leu Ala Gly Ala Thr Thr Leu Gly Asp Met Ile Tyr Val Ser
370             375             380

Gly Gly Phe Asp Gly Ser Arg Arg His Thr Ser Met Glu Arg Tyr Asp
385             390             395             400

Pro Asn Ile Asp Gln Trp Ser Met Leu Gly Asp Met Gln Thr Ala Arg
                405             410             415

Glu Gly Ala Gly Leu Val Val Ala Ser Gly Val Ile Tyr Cys Leu Gly
            420             425             430

Gly Tyr Asp Gly Leu Asn Ile Leu Asn Ser Val Glu Lys Tyr Asp Pro
            435             440             445

His Thr Gly His Trp Thr Asn Val Thr Pro Met Ala Thr Lys Arg Ser
450             455             460
```

```
Gly Ala Gly Val Ala Leu Leu Asn Asp His Ile Tyr Val Val Gly Gly
465                 470                 475                 480

Phe Asp Gly Thr Ala His Leu Ser Ser Val Glu Ala Tyr Asn Ile Arg
            485                 490                 495

Thr Asp Ser Trp Thr Thr Val Thr Ser Met Thr Thr Pro Arg Cys Tyr
                500                 505                 510

Val Gly Ala Thr Val Leu Arg Gly Arg Leu Tyr Ala Ile Ala Gly Tyr
            515                 520                 525

Asp Gly Asn Ser Leu Leu Ser Ser Ile Glu Cys Tyr Asp Pro Ile Ile
        530                 535                 540

Asp Ser Trp Glu Val Val Thr Ser Met Gly Thr Gln Arg Cys Asp Ala
545                 550                 555                 560

Gly Val Cys Val Leu Arg Glu Lys
                565

<210> SEQ ID NO 7
<211> LENGTH: 916
<212> TYPE: PRT
<213> ORGANISM: Homo sapiens

<400> SEQUENCE: 7

Met Asp Cys Glu His Ser Leu Ser Leu Pro Cys Arg Gly Ala Glu Ala
1               5                   10                  15

Trp Glu Ile Gly Ile Asp Lys Tyr Leu Tyr Ala Met Arg Leu Ser Asp
                20                  25                  30

Glu Thr Leu Ile Asp Ile Met Thr Arg Phe Arg Lys Glu Met Lys Asn
            35                  40                  45

Gly Leu Ser Arg Asp Phe Asn Pro Thr Ala Thr Val Lys Met Leu Pro
50                  55                  60

Thr Phe Val Arg Ser Ile Pro Asp Gly Ser Glu Lys Gly Asp Phe Ile
65                  70                  75                  80

Ala Leu Asp Leu Gly Gly Ser Ser Phe Arg Ile Leu Arg Val Gln Val
                85                  90                  95

Asn His Glu Lys Asn Gln Asn Val His Met Glu Ser Glu Val Tyr Asp
            100                 105                 110

Thr Pro Glu Asn Ile Val His Gly Ser Gly Ser Gln Leu Phe Asp His
        115                 120                 125

Val Ala Glu Cys Leu Gly Asp Phe Met Glu Lys Arg Lys Ile Lys Asp
    130                 135                 140

Lys Lys Leu Pro Val Gly Phe Thr Phe Ser Phe Pro Cys Gln Gln Ser
145                 150                 155                 160

Lys Ile Asp Glu Ala Ile Leu Ile Thr Trp Thr Lys Arg Phe Lys Ala
                165                 170                 175

Ser Gly Val Glu Gly Ala Asp Val Val Lys Leu Leu Asn Lys Ala Ile
            180                 185                 190

Lys Lys Arg Gly Asp Tyr Asp Ala Asn Ile Val Ala Val Val Asn Asp
        195                 200                 205

Thr Val Gly Thr Met Met Thr Cys Gly Tyr Asp Asp Gln His Cys Glu
    210                 215                 220

Val Gly Leu Ile Ile Gly Thr Gly Thr Asn Ala Cys Tyr Met Glu Glu
225                 230                 235                 240

Leu Arg His Ile Asp Leu Val Glu Gly Asp Glu Gly Arg Met Cys Ile
                245                 250                 255

Asn Thr Glu Trp Gly Ala Phe Gly Asp Asp Gly Ser Leu Glu Asp Ile
            260                 265                 270
```

```
Arg Thr Glu Phe Asp Arg Glu Ile Asp Arg Gly Ser Leu Asn Pro Gly
            275                 280                 285

Lys Gln Leu Phe Glu Lys Met Val Ser Gly Met Tyr Leu Gly Glu Leu
        290                 295                 300

Val Arg Leu Ile Leu Val Lys Met Ala Lys Glu Gly Leu Leu Phe Glu
305                 310                 315                 320

Gly Arg Ile Thr Pro Glu Leu Leu Thr Arg Gly Lys Phe Asn Thr Ser
                325                 330                 335

Asp Val Ser Ala Ile Glu Lys Asn Lys Glu Gly Leu His Asn Ala Lys
                340                 345                 350

Glu Ile Leu Thr Arg Leu Gly Val Glu Pro Ser Asp Asp Cys Val
            355                 360                 365

Ser Val Gln His Val Cys Thr Ile Val Ser Phe Arg Ser Ala Asn Leu
        370                 375                 380

Val Ala Ala Thr Leu Gly Ala Ile Leu Asn Arg Leu Arg Asp Asn Lys
385                 390                 395                 400

Gly Thr Pro Arg Leu Arg Thr Thr Val Gly Val Asp Gly Ser Leu Tyr
                405                 410                 415

Lys Thr His Pro Gln Tyr Ser Arg Arg Phe His Lys Thr Leu Arg Arg
            420                 425                 430

Leu Val Pro Asp Ser Asp Val Arg Phe Leu Leu Ser Glu Ser Gly Ser
        435                 440                 445

Gly Lys Gly Ala Ala Met Val Thr Ala Val Ala Tyr Arg Leu Ala Glu
    450                 455                 460

Gln His Arg Gln Ile Glu Glu Thr Leu Ala His Phe His Leu Thr Lys
465                 470                 475                 480

Asp Met Leu Leu Glu Val Lys Lys Arg Met Arg Ala Glu Met Glu Leu
                485                 490                 495

Gly Leu Arg Lys Gln Thr His Asn Asn Ala Val Val Lys Met Leu Pro
            500                 505                 510

Ser Phe Val Arg Arg Thr Pro Asp Gly Thr Glu Asn Gly Asp Phe Leu
        515                 520                 525

Ala Leu Asp Leu Gly Gly Thr Asn Phe Arg Val Leu Leu Val Lys Ile
    530                 535                 540

Arg Ser Gly Lys Lys Arg Thr Val Glu Met His Asn Lys Ile Tyr Ala
545                 550                 555                 560

Ile Pro Ile Glu Ile Met Gln Gly Thr Gly Glu Glu Leu Phe Asp His
                565                 570                 575

Ile Val Ser Cys Ile Ser Asp Phe Leu Asp Tyr Met Gly Ile Lys Gly
            580                 585                 590

Pro Arg Met Pro Leu Gly Phe Thr Phe Ser Phe Pro Cys Gln Gln Thr
        595                 600                 605

Ser Leu Asp Ala Gly Ile Leu Ile Thr Trp Thr Lys Gly Phe Lys Ala
    610                 615                 620

Thr Asp Cys Val Gly His Asp Val Val Thr Leu Leu Arg Asp Ala Ile
625                 630                 635                 640

Lys Arg Arg Glu Glu Phe Asp Leu Asp Val Val Ala Val Val Asn Asp
                645                 650                 655

Thr Val Gly Thr Met Met Thr Cys Ala Tyr Glu Glu Pro Thr Cys Glu
            660                 665                 670

Val Gly Leu Ile Val Gly Thr Gly Ser Asn Ala Cys Tyr Met Glu Glu
        675                 680                 685
```

```
Met Lys Asn Val Glu Met Val Glu Gly Asp Gln Gly Gln Met Cys Ile
    690             695                 700
Asn Met Glu Trp Gly Ala Phe Gly Asp Asn Gly Cys Leu Asp Asp Ile
705             710                 715                 720
Arg Thr His Tyr Asp Arg Leu Val Asp Glu Tyr Ser Leu Asn Ala Gly
            725                 730                 735
Lys Gln Arg Tyr Glu Lys Met Ile Ser Gly Met Tyr Leu Gly Glu Ile
        740                 745                 750
Val Arg Asn Ile Leu Ile Asp Phe Thr Lys Lys Gly Phe Leu Phe Arg
    755                 760                 765
Gly Gln Ile Ser Glu Thr Leu Lys Thr Arg Gly Ile Phe Glu Thr Lys
770                 775                 780
Phe Leu Ser Gln Ile Glu Ser Asp Arg Leu Ala Leu Leu Gln Val Arg
785                 790                 795                 800
Ala Ile Leu Gln Gln Leu Gly Leu Asn Ser Thr Cys Asp Asp Ser Ile
                805                 810                 815
Leu Val Lys Thr Val Cys Gly Val Val Ser Arg Arg Ala Ala Gln Leu
            820                 825                 830
Cys Gly Ala Gly Met Ala Ala Val Val Asp Lys Ile Arg Glu Asn Arg
        835                 840                 845
Gly Leu Asp Arg Leu Asn Val Thr Val Gly Val Asp Gly Thr Leu Tyr
    850                 855                 860
Lys Leu His Pro His Phe Ser Arg Ile Met His Gln Thr Val Lys Glu
865                 870                 875                 880
Leu Ser Pro Lys Cys Asn Val Ser Phe Leu Leu Ser Glu Asp Gly Ser
                885                 890                 895
Gly Lys Gly Ala Ala Leu Ile Thr Ala Val Gly Val Arg Leu Arg Thr
            900                 905                 910
Glu Ala Ser Ser
            915

<210> SEQ ID NO 8
<211> LENGTH: 917
<212> TYPE: PRT
<213> ORGANISM: Homo sapiens

<400> SEQUENCE: 8

Met Ile Ala Ser His Leu Leu Ala Tyr Phe Phe Thr Glu Leu Asn His
1               5                   10                  15
Asp Gln Val Gln Lys Val Asp Gln Tyr Leu Tyr His Met Arg Leu Ser
            20                  25                  30
Asp Glu Thr Leu Leu Glu Ile Ser Lys Arg Phe Arg Lys Glu Met Glu
        35                  40                  45
Lys Gly Leu Gly Ala Thr Thr His Pro Thr Ala Ala Val Lys Met Leu
    50                  55                  60
Pro Thr Phe Val Arg Ser Thr Pro Asp Gly Thr Glu His Gly Glu Phe
65              70                  75                  80
Leu Ala Leu Asp Leu Gly Gly Thr Asn Phe Arg Val Leu Trp Val Lys
                85                  90                  95
Val Thr Asp Asn Gly Leu Gln Lys Val Glu Met Glu Asn Gln Ile Tyr
            100                 105                 110
Ala Ile Pro Glu Asp Ile Met Arg Gly Ser Gly Thr Gln Leu Phe Asp
        115                 120                 125
His Ile Ala Glu Cys Leu Ala Asn Phe Met Asp Lys Leu Gln Ile Lys
    130                 135                 140
```

```
Asp Lys Lys Leu Pro Leu Gly Phe Thr Phe Ser Phe Pro Cys His Gln
145                 150                 155                 160

Thr Lys Leu Asp Glu Ser Phe Leu Val Ser Trp Thr Lys Gly Phe Lys
            165                 170                 175

Ser Ser Gly Val Glu Gly Arg Asp Val Val Ala Leu Ile Arg Lys Ala
        180                 185                 190

Ile Gln Arg Arg Gly Asp Phe Asp Ile Asp Ile Val Ala Val Val Asn
    195                 200                 205

Asp Thr Val Gly Thr Met Met Thr Cys Gly Tyr Asp Asp His Asn Cys
210                 215                 220

Glu Ile Gly Leu Ile Val Gly Thr Gly Ser Asn Ala Cys Tyr Met Glu
225                 230                 235                 240

Glu Met Arg His Ile Asp Met Val Glu Gly Asp Glu Gly Arg Met Cys
            245                 250                 255

Ile Asn Met Glu Trp Gly Ala Phe Gly Asp Asp Gly Ser Leu Asn Asp
        260                 265                 270

Ile Arg Thr Glu Phe Asp Gln Glu Ile Asp Met Gly Ser Leu Asn Pro
    275                 280                 285

Gly Lys Gln Leu Phe Glu Lys Met Ile Ser Gly Met Tyr Met Gly Glu
290                 295                 300

Leu Val Arg Leu Ile Leu Val Lys Met Ala Lys Glu Glu Leu Leu Phe
305                 310                 315                 320

Gly Gly Lys Leu Ser Pro Glu Leu Leu Asn Thr Gly Arg Phe Glu Thr
            325                 330                 335

Lys Asp Ile Ser Asp Ile Glu Gly Glu Lys Asp Gly Ile Arg Lys Ala
        340                 345                 350

Arg Glu Val Leu Met Arg Leu Gly Leu Asp Pro Thr Gln Glu Asp Cys
    355                 360                 365

Val Ala Thr His Arg Ile Cys Gln Ile Val Ser Thr Arg Ser Ala Ser
370                 375                 380

Leu Cys Ala Ala Thr Leu Ala Ala Val Leu Gln Arg Ile Lys Glu Asn
385                 390                 395                 400

Lys Gly Glu Glu Arg Leu Arg Ser Thr Ile Gly Val Asp Gly Ser Val
            405                 410                 415

Tyr Lys Lys His Pro His Phe Ala Lys Arg Leu His Lys Thr Val Arg
        420                 425                 430

Arg Leu Val Pro Gly Cys Asp Val Arg Phe Leu Arg Ser Glu Asp Gly
    435                 440                 445

Ser Gly Lys Gly Ala Ala Met Val Thr Ala Val Ala Tyr Arg Leu Ala
450                 455                 460

Asp Gln His Arg Ala Arg Gln Lys Thr Leu Glu His Leu Gln Leu Ser
465                 470                 475                 480

His Asp Gln Leu Leu Glu Val Lys Arg Arg Met Lys Val Glu Met Glu
            485                 490                 495

Arg Gly Leu Ser Lys Glu Thr His Ala Ser Ala Pro Val Lys Met Leu
        500                 505                 510

Pro Thr Tyr Val Cys Ala Thr Pro Asp Gly Thr Glu Lys Gly Asp Phe
    515                 520                 525

Leu Ala Leu Asp Leu Gly Gly Thr Asn Phe Arg Val Leu Leu Val Arg
530                 535                 540

Val Arg Asn Gly Lys Trp Gly Gly Val Glu Met His Asn Lys Ile Tyr
545                 550                 555                 560
```

```
Ala Ile Pro Gln Glu Val Met His Gly Thr Gly Asp Glu Leu Phe Asp
            565                 570                 575

His Ile Val Gln Cys Ile Ala Asp Phe Leu Glu Tyr Met Gly Met Lys
            580                 585                 590

Gly Val Ser Leu Pro Leu Gly Phe Thr Phe Ser Phe Pro Cys Gln Gln
            595                 600                 605

Asn Ser Leu Asp Glu Ser Ile Leu Leu Lys Trp Thr Lys Gly Phe Lys
            610                 615                 620

Ala Ser Gly Cys Glu Gly Glu Asp Val Val Thr Leu Leu Lys Glu Ala
625                 630                 635                 640

Ile His Arg Arg Glu Glu Phe Asp Leu Asp Val Val Ala Val Val Asn
            645                 650                 655

Asp Thr Val Gly Thr Met Met Thr Cys Gly Phe Glu Asp Pro His Cys
            660                 665                 670

Glu Val Gly Leu Ile Val Gly Thr Gly Ser Asn Ala Cys Tyr Met Glu
            675                 680                 685

Glu Met Arg Asn Val Glu Leu Val Glu Gly Glu Gly Arg Met Cys
            690                 695                 700

Val Asn Met Glu Trp Gly Ala Phe Gly Asp Asn Gly Cys Leu Asp Asp
705                 710                 715                 720

Phe Arg Thr Glu Phe Asp Val Ala Val Asp Glu Leu Ser Leu Asn Pro
            725                 730                 735

Gly Lys Gln Arg Phe Glu Lys Met Ile Ser Gly Met Tyr Leu Gly Glu
            740                 745                 750

Ile Val Arg Asn Ile Leu Ile Asp Phe Thr Lys Arg Gly Leu Leu Phe
            755                 760                 765

Arg Gly Arg Ile Ser Glu Arg Leu Lys Thr Arg Gly Ile Phe Glu Thr
770                 775                 780

Lys Phe Leu Ser Gln Ile Glu Ser Asp Cys Leu Ala Leu Leu Gln Val
785                 790                 795                 800

Arg Ala Ile Leu Gln His Leu Gly Leu Glu Ser Thr Cys Asp Asp Ser
            805                 810                 815

Ile Ile Val Lys Glu Val Cys Thr Val Val Ala Arg Arg Ala Ala Gln
            820                 825                 830

Leu Cys Gly Ala Gly Met Ala Ala Val Val Asp Arg Ile Arg Glu Asn
            835                 840                 845

Arg Gly Leu Asp Ala Leu Lys Val Thr Val Gly Val Asp Gly Thr Leu
850                 855                 860

Tyr Lys Leu His Pro His Phe Ala Lys Val Met His Glu Thr Val Lys
865                 870                 875                 880

Asp Leu Ala Pro Lys Cys Asp Val Ser Phe Leu Gln Ser Glu Asp Gly
            885                 890                 895

Ser Gly Lys Gly Ala Ala Leu Ile Thr Ala Val Ala Cys Arg Ile Arg
            900                 905                 910

Glu Ala Gly Gln Arg
            915

<210> SEQ ID NO 9
<211> LENGTH: 923
<212> TYPE: PRT
<213> ORGANISM: Homo sapiens

<400> SEQUENCE: 9

Met Asp Ser Ile Gly Ser Ser Gly Leu Arg Gln Gly Glu Glu Thr Leu
1               5                   10                  15
```

```
Ser Cys Ser Glu Glu Gly Leu Pro Gly Pro Ser Asp Ser Ser Glu Leu
             20                  25                  30

Val Gln Glu Cys Leu Gln Gln Phe Lys Val Thr Arg Ala Gln Leu Gln
         35                  40                  45

Gln Ile Gln Ala Ser Leu Leu Gly Ser Met Glu Gln Ala Leu Arg Gly
     50                  55                  60

Gln Ala Ser Pro Ala Pro Ala Val Arg Met Leu Pro Thr Tyr Val Gly
 65                  70                  75                  80

Ser Thr Pro His Gly Thr Glu Gln Gly Asp Phe Val Val Leu Glu Leu
                 85                  90                  95

Gly Ala Thr Gly Ala Ser Leu Arg Val Leu Trp Val Thr Leu Thr Gly
                100                 105                 110

Ile Glu Gly His Arg Val Glu Pro Arg Ser Gln Glu Phe Val Ile Pro
            115                 120                 125

Gln Glu Val Met Leu Gly Ala Gly Gln Gln Leu Phe Asp Phe Ala Ala
        130                 135                 140

His Cys Leu Ser Glu Phe Leu Asp Ala Gln Pro Val Asn Lys Gln Gly
145                 150                 155                 160

Leu Gln Leu Gly Phe Ser Phe Ser Phe Pro Cys His Gln Thr Gly Leu
                165                 170                 175

Asp Arg Ser Thr Leu Ile Ser Trp Thr Lys Gly Phe Arg Cys Ser Gly
            180                 185                 190

Val Glu Gly Gln Asp Val Val Gln Leu Leu Arg Asp Ala Ile Arg Arg
        195                 200                 205

Gln Gly Ala Tyr Asn Ile Asp Val Val Ala Val Val Asn Asp Thr Val
    210                 215                 220

Gly Thr Met Met Gly Cys Glu Pro Gly Val Arg Pro Cys Glu Val Gly
225                 230                 235                 240

Leu Val Val Asp Thr Gly Thr Asn Ala Cys Tyr Met Glu Glu Ala Arg
                245                 250                 255

His Val Ala Val Leu Asp Glu Asp Arg Gly Arg Val Cys Val Ser Val
            260                 265                 270

Glu Trp Gly Ser Phe Ser Asp Asp Gly Ala Leu Gly Pro Val Leu Thr
        275                 280                 285

Thr Phe Asp His Thr Leu Asp His Glu Ser Leu Asn Pro Gly Ala Gln
    290                 295                 300

Arg Phe Glu Lys Met Ile Gly Gly Leu Tyr Leu Gly Glu Leu Val Arg
305                 310                 315                 320

Leu Val Leu Ala His Leu Ala Arg Cys Gly Val Leu Phe Gly Gly Cys
                325                 330                 335

Thr Ser Pro Ala Leu Leu Ser Gln Gly Ser Ile Leu Leu Glu His Val
            340                 345                 350

Ala Glu Met Glu Asp Pro Ser Thr Gly Ala Ala Arg Val His Ala Ile
        355                 360                 365

Leu Gln Asp Leu Gly Leu Ser Pro Gly Ala Ser Asp Val Glu Leu Val
    370                 375                 380

Gln His Val Cys Ala Ala Val Cys Thr Arg Ala Ala Gln Leu Cys Ala
385                 390                 395                 400

Ala Ala Leu Ala Ala Val Leu Ser Cys Leu Gln His Ser Arg Glu Gln
                405                 410                 415

Gln Thr Leu Gln Val Ala Val Ala Thr Gly Gly Arg Val Cys Glu Arg
            420                 425                 430
```

```
His Pro Arg Phe Cys Ser Val Leu Gln Gly Thr Val Met Leu Leu Ala
            435                 440                 445

Pro Glu Cys Asp Val Ser Leu Ile Pro Ser Val Asp Gly Gly Gly Arg
450                 455                 460

Gly Val Ala Met Val Thr Ala Val Ala Arg Leu Ala Ala His Arg
465                 470                 475                 480

Arg Leu Leu Glu Glu Thr Leu Ala Pro Phe Arg Leu Asn His Asp Gln
                485                 490                 495

Leu Ala Ala Val Gln Ala Gln Met Arg Lys Ala Met Ala Lys Gly Leu
                500                 505                 510

Arg Gly Glu Ala Ser Ser Leu Arg Met Leu Pro Thr Phe Val Arg Ala
            515                 520                 525

Thr Pro Asp Gly Ser Glu Arg Gly Asp Phe Leu Ala Leu Asp Leu Gly
530                 535                 540

Gly Thr Asn Phe Arg Val Leu Leu Val Arg Val Thr Thr Gly Val Gln
545                 550                 555                 560

Ile Thr Ser Glu Ile Tyr Ser Ile Pro Glu Thr Val Ala Gln Gly Ser
                565                 570                 575

Gly Gln Gln Leu Phe Asp His Ile Val Asp Cys Ile Val Asp Phe Gln
            580                 585                 590

Gln Lys Gln Gly Leu Ser Gly Gln Ser Leu Pro Leu Gly Phe Thr Phe
            595                 600                 605

Ser Phe Pro Cys Arg Gln Leu Gly Leu Asp Gln Gly Ile Leu Leu Asn
    610                 615                 620

Trp Thr Lys Gly Phe Lys Ala Ser Asp Cys Glu Gly Gln Asp Val Val
625                 630                 635                 640

Ser Leu Leu Arg Glu Ala Ile Thr Arg Arg Gln Ala Val Glu Leu Asn
                645                 650                 655

Val Val Ala Ile Val Asn Asp Thr Val Gly Thr Met Met Ser Cys Gly
                660                 665                 670

Tyr Glu Asp Pro Arg Cys Glu Ile Gly Leu Ile Val Gly Thr Gly Thr
            675                 680                 685

Asn Ala Cys Tyr Met Glu Glu Leu Arg Asn Val Ala Gly Val Pro Gly
690                 695                 700

Asp Ser Gly Arg Met Cys Ile Asn Met Glu Trp Gly Ala Phe Gly Asp
705                 710                 715                 720

Asp Gly Ser Leu Ala Met Leu Ser Thr Arg Phe Asp Ala Ser Val Asp
                725                 730                 735

Gln Ala Ser Ile Asn Pro Gly Lys Gln Arg Phe Glu Lys Met Ile Ser
            740                 745                 750

Gly Met Tyr Leu Gly Glu Ile Val Arg His Ile Leu Leu His Leu Thr
            755                 760                 765

Ser Leu Gly Val Leu Phe Arg Gly Gln Gln Ile Gln Arg Leu Gln Thr
770                 775                 780

Arg Asp Ile Phe Lys Thr Lys Phe Leu Ser Glu Ile Glu Ser Asp Ser
785                 790                 795                 800

Leu Ala Leu Arg Gln Val Arg Ala Ile Leu Glu Asp Leu Gly Leu Pro
                805                 810                 815

Leu Thr Ser Asp Asp Ala Leu Met Val Leu Glu Val Cys Gln Ala Val
            820                 825                 830

Ser Gln Arg Ala Ala Gln Leu Cys Gly Ala Gly Val Ala Ala Val Val
            835                 840                 845

Glu Lys Ile Arg Glu Asn Arg Gly Leu Glu Glu Leu Ala Val Ser Val
```

```
                    850                 855                 860
Gly Val Asp Gly Thr Leu Tyr Lys Leu His Pro Arg Phe Ser Ser Leu
865                 870                 875                 880

Val Ala Ala Thr Val Arg Glu Leu Ala Pro Arg Cys Val Val Thr Phe
                    885                 890                 895

Leu Gln Ser Glu Asp Gly Ser Gly Lys Gly Ala Ala Leu Val Thr Ala
                900                 905                 910

Val Ala Cys Arg Leu Ala Gln Leu Thr Arg Val
                915                 920

<210> SEQ ID NO 10
<211> LENGTH: 466
<212> TYPE: PRT
<213> ORGANISM: Homo sapiens

<400> SEQUENCE: 10

Met Ala Met Asp Val Thr Arg Ser Gln Ala Gln Thr Ala Leu Thr Leu
1               5                   10                  15

Val Glu Gln Ile Leu Ala Glu Phe Gln Leu Gln Glu Glu Asp Leu Lys
                20                  25                  30

Lys Val Met Arg Met Gln Lys Glu Met Asp Arg Gly Leu Arg Leu
            35                  40                  45

Glu Thr His Glu Glu Ala Ser Val Lys Met Leu Pro Thr Tyr Val Arg
50                  55                  60

Ser Thr Pro Glu Gly Ser Glu Val Gly Asp Phe Leu Ser Leu Asp Leu
65                  70                  75                  80

Gly Gly Thr Asn Phe Arg Val Met Leu Val Lys Val Gly Glu Gly Glu
                85                  90                  95

Glu Gly Gln Trp Ser Val Lys Thr Lys His Gln Met Tyr Ser Ile Pro
            100                 105                 110

Glu Asp Ala Met Thr Gly Thr Ala Glu Met Leu Phe Asp Tyr Ile Ser
        115                 120                 125

Glu Cys Ile Ser Asp Phe Leu Asp Lys His Gln Met Lys His Lys Lys
130                 135                 140

Leu Pro Leu Gly Phe Thr Phe Ser Phe Pro Val Arg His Glu Asp Ile
145                 150                 155                 160

Asp Lys Gly Ile Leu Leu Asn Trp Thr Lys Gly Phe Lys Ala Ser Gly
                165                 170                 175

Ala Glu Gly Asn Asn Val Val Gly Leu Leu Arg Asp Ala Ile Lys Arg
            180                 185                 190

Arg Gly Asp Phe Glu Met Asp Val Val Ala Met Val Asn Asp Thr Val
        195                 200                 205

Ala Thr Met Ile Ser Cys Tyr Tyr Glu Asp His Gln Cys Glu Val Gly
210                 215                 220

Met Ile Val Gly Thr Gly Cys Asn Ala Cys Tyr Met Glu Glu Met Gln
225                 230                 235                 240

Asn Val Glu Leu Val Glu Gly Asp Glu Gly Arg Met Cys Val Asn Thr
                245                 250                 255

Glu Trp Gly Ala Phe Gly Asp Ser Gly Glu Leu Asp Glu Phe Leu Leu
            260                 265                 270

Glu Tyr Asp Arg Leu Val Asp Glu Ser Ser Ala Asn Pro Gly Gln Gln
        275                 280                 285

Leu Tyr Glu Lys Leu Ile Gly Gly Lys Tyr Met Gly Glu Leu Val Arg
290                 295                 300
```

```
Leu Val Leu Leu Arg Leu Val Asp Glu Asn Leu Phe His Gly Glu
305                 310                 315                 320

Ala Ser Glu Gln Leu Arg Thr Arg Gly Ala Phe Glu Thr Arg Phe Val
            325                 330                 335

Ser Gln Val Glu Ser Asp Thr Gly Asp Arg Lys Gln Ile Tyr Asn Ile
        340                 345                 350

Leu Ser Thr Leu Gly Leu Arg Pro Ser Thr Thr Asp Cys Asp Ile Val
    355                 360                 365

Arg Arg Ala Cys Glu Ser Val Ser Thr Arg Ala Ala His Met Cys Ser
370                 375                 380

Ala Gly Leu Ala Gly Val Ile Asn Arg Met Arg Glu Ser Arg Ser Glu
385                 390                 395                 400

Asp Val Met Arg Ile Thr Val Gly Val Asp Gly Ser Val Tyr Lys Leu
            405                 410                 415

His Pro Ser Phe Lys Glu Arg Phe His Ala Ser Val Arg Arg Leu Thr
        420                 425                 430

Pro Ser Cys Glu Ile Thr Phe Ile Glu Ser Glu Gly Ser Gly Arg
    435                 440                 445

Gly Ala Ala Leu Val Ser Ala Val Ala Cys Lys Lys Ala Cys Met Leu
450                 455                 460

Gly Gln
465

<210> SEQ ID NO 11
<211> LENGTH: 917
<212> TYPE: PRT
<213> ORGANISM: Homo sapiens

<400> SEQUENCE: 11

Met Phe Ala Val His Leu Met Ala Phe Tyr Phe Ser Lys Leu Lys Glu
1               5                   10                  15

Asp Gln Ile Lys Lys Val Asp Arg Phe Leu Tyr His Met Arg Leu Ser
            20                  25                  30

Asp Asp Thr Leu Leu Asp Ile Met Arg Arg Phe Arg Ala Glu Met Glu
        35                  40                  45

Lys Gly Leu Ala Lys Asp Thr Asn Pro Thr Ala Ala Val Lys Met Leu
    50                  55                  60

Pro Thr Phe Val Arg Ala Ile Pro Asp Gly Ser Glu Asn Gly Glu Phe
65                  70                  75                  80

Leu Ser Leu Asp Leu Gly Gly Ser Lys Phe Arg Val Leu Lys Val Gln
                85                  90                  95

Val Ala Glu Glu Gly Lys Arg His Val Gln Met Glu Ser Gln Phe Tyr
            100                 105                 110

Pro Thr Pro Asn Glu Ile Ile Arg Gly Asn Gly Thr Glu Leu Phe Glu
        115                 120                 125

Tyr Val Ala Asp Cys Leu Ala Asp Phe Met Lys Thr Lys Asp Leu Lys
    130                 135                 140

His Lys Lys Leu Pro Leu Gly Leu Thr Phe Ser Phe Pro Cys Arg Gln
145                 150                 155                 160

Thr Lys Leu Glu Glu Gly Val Leu Leu Ser Trp Thr Lys Phe Lys
                165                 170                 175

Ala Arg Gly Val Gln Asp Thr Asp Val Val Ser Arg Leu Thr Lys Ala
            180                 185                 190

Met Arg Arg His Lys Asp Met Asp Val Asp Ile Leu Ala Leu Val Asn
        195                 200                 205
```

```
Asp Thr Val Gly Thr Met Met Thr Cys Ala Tyr Asp Asp Pro Tyr Cys
    210                 215                 220

Glu Val Gly Val Ile Ile Gly Thr Gly Thr Asn Ala Cys Tyr Met Glu
225                 230                 235                 240

Asp Met Ser Asn Ile Asp Leu Val Glu Gly Asp Glu Gly Arg Met Cys
                245                 250                 255

Ile Asn Thr Glu Trp Gly Ala Phe Gly Asp Asp Gly Ala Leu Glu Asp
            260                 265                 270

Ile Arg Thr Glu Phe Asp Arg Glu Leu Asp Leu Gly Ser Leu Asn Pro
        275                 280                 285

Gly Lys Gln Leu Phe Glu Lys Met Ile Ser Gly Leu Tyr Leu Gly Glu
    290                 295                 300

Leu Val Arg Leu Ile Leu Leu Lys Met Ala Lys Ala Gly Leu Leu Phe
305                 310                 315                 320

Gly Gly Glu Lys Ser Ser Ala Leu His Thr Lys Gly Lys Ile Glu Thr
                325                 330                 335

Arg His Val Ala Ala Met Glu Lys Tyr Lys Glu Gly Leu Ala Asn Thr
            340                 345                 350

Arg Glu Ile Leu Val Asp Leu Gly Leu Glu Pro Ser Glu Ala Asp Cys
        355                 360                 365

Ile Ala Val Gln His Val Cys Thr Ile Val Ser Phe Arg Ser Ala Asn
    370                 375                 380

Leu Cys Ala Ala Ala Leu Ala Ala Ile Leu Thr Arg Leu Arg Glu Asn
385                 390                 395                 400

Lys Lys Val Glu Arg Leu Arg Thr Thr Val Gly Met Asp Gly Thr Leu
                405                 410                 415

Tyr Lys Ile His Pro Gln Tyr Pro Lys Arg Leu His Lys Val Val Arg
            420                 425                 430

Lys Leu Val Pro Ser Cys Asp Val Arg Phe Leu Leu Ser Glu Ser Gly
        435                 440                 445

Ser Thr Lys Gly Ala Ala Met Val Thr Ala Val Ala Ser Arg Val Gln
    450                 455                 460

Ala Gln Arg Lys Gln Ile Asp Arg Val Leu Ala Leu Phe Gln Leu Thr
465                 470                 475                 480

Arg Glu Gln Leu Val Asp Val Gln Ala Lys Met Arg Ala Glu Leu Glu
                485                 490                 495

Tyr Gly Leu Lys Lys Lys Ser His Gly Leu Ala Thr Val Arg Met Leu
            500                 505                 510

Pro Thr Tyr Val Cys Gly Leu Pro Asp Gly Thr Glu Lys Gly Lys Phe
        515                 520                 525

Leu Ala Leu Asp Leu Gly Gly Thr Asn Phe Arg Val Leu Leu Val Lys
    530                 535                 540

Ile Arg Ser Gly Arg Arg Ser Val Arg Met Tyr Asn Lys Ile Phe Ala
545                 550                 555                 560

Ile Pro Leu Glu Ile Met Gln Gly Thr Gly Glu Glu Leu Phe Asp His
                565                 570                 575

Ile Val Gln Cys Ile Ala Asp Phe Leu Asp Tyr Met Gly Leu Lys Gly
            580                 585                 590

Ala Ser Leu Pro Leu Gly Phe Thr Phe Ser Phe Pro Cys Arg Gln Met
        595                 600                 605

Ser Ile Asp Lys Gly Thr Leu Ile Gly Trp Thr Lys Gly Phe Lys Ala
    610                 615                 620
```

Thr Asp Cys Glu Gly Glu Asp Val Val Asp Met Leu Arg Glu Ala Ile
625                 630                 635                 640

Lys Arg Arg Asn Glu Phe Asp Leu Asp Ile Val Ala Val Val Asn Asp
            645                 650                 655

Thr Val Gly Thr Met Met Thr Cys Gly Tyr Glu Asp Pro Asn Cys Glu
        660                 665                 670

Ile Gly Leu Ile Ala Gly Thr Gly Ser Asn Met Cys Tyr Met Glu Asp
    675                 680                 685

Met Arg Asn Ile Glu Met Val Glu Gly Glu Gly Lys Met Cys Ile
690                 695                 700

Asn Thr Glu Trp Gly Gly Phe Gly Asp Asn Gly Cys Ile Asp Asp Ile
705                 710                 715                 720

Arg Thr Arg Tyr Asp Thr Glu Val Asp Glu Gly Ser Leu Asn Pro Gly
            725                 730                 735

Lys Gln Arg Tyr Glu Lys Met Thr Ser Gly Met Tyr Leu Gly Glu Ile
            740                 745                 750

Val Arg Gln Ile Leu Ile Asp Leu Thr Lys Gln Gly Leu Leu Phe Arg
        755                 760                 765

Gly Gln Ile Ser Glu Arg Leu Arg Thr Arg Gly Ile Phe Glu Thr Lys
770                 775                 780

Phe Leu Ser Gln Ile Glu Ser Asp Arg Leu Ala Leu Leu Gln Val Arg
785                 790                 795                 800

Arg Ile Leu Gln Gln Leu Gly Leu Asp Ser Thr Cys Glu Asp Ser Ile
            805                 810                 815

Val Val Lys Glu Val Cys Gly Ala Val Ser Arg Arg Ala Ala Gln Leu
        820                 825                 830

Cys Gly Ala Gly Leu Ala Ala Ile Val Glu Lys Arg Arg Glu Asp Gln
    835                 840                 845

Gly Leu Glu His Leu Arg Ile Thr Val Gly Val Asp Gly Thr Leu Tyr
850                 855                 860

Lys Leu His Pro His Phe Ser Arg Ile Leu Gln Glu Thr Val Lys Glu
865                 870                 875                 880

Leu Ala Pro Arg Cys Asp Val Thr Phe Met Leu Ser Glu Asp Gly Ser
            885                 890                 895

Gly Lys Gly Ala Ala Leu Ile Thr Ala Val Ala Lys Arg Leu Gln Gln
        900                 905                 910

Ala Gln Lys Glu Asn
        915

<210> SEQ ID NO 12
<211> LENGTH: 568
<212> TYPE: PRT
<213> ORGANISM: Homo sapiens

<400> SEQUENCE: 12

Met Gly Gly Ile Met Ala Pro Lys Asp Ile Met Thr Asn Thr His Ala
1               5                   10                  15

Lys Ser Ile Leu Asn Ser Met Asn Ser Leu Arg Lys Ser Asn Thr Leu
            20                  25                  30

Cys Asp Val Thr Leu Arg Val Glu Gln Lys Asp Phe Pro Ala His Arg
        35                  40                  45

Ile Val Leu Ala Ala Cys Ser Asp Tyr Phe Cys Ala Met Phe Thr Ser
    50                  55                  60

Glu Leu Ser Glu Lys Gly Lys Pro Tyr Val Asp Ile Gln Gly Leu Thr
65                  70                  75                  80

```
Ala Ser Thr Met Glu Ile Leu Leu Asp Phe Val Tyr Thr Glu Thr Val
                85                  90                  95
His Val Thr Val Glu Asn Val Gln Glu Leu Leu Pro Ala Ala Cys Leu
            100                 105                 110
Leu Gln Leu Lys Gly Val Lys Gln Ala Cys Cys Glu Phe Leu Glu Ser
        115                 120                 125
Gln Leu Asp Pro Ser Asn Cys Leu Gly Ile Arg Asp Phe Ala Glu Thr
    130                 135                 140
His Asn Cys Val Asp Leu Met Gln Ala Ala Glu Val Phe Ser Gln Lys
145                 150                 155                 160
His Phe Pro Glu Val Val Gln His Glu Glu Phe Ile Leu Leu Ser Gln
                165                 170                 175
Gly Glu Val Glu Lys Leu Ile Lys Cys Asp Glu Ile Gln Val Asp Ser
            180                 185                 190
Glu Glu Pro Val Phe Glu Ala Val Ile Asn Trp Val Lys His Ala Lys
        195                 200                 205
Lys Glu Arg Glu Glu Ser Leu Pro Asn Leu Leu Gln Tyr Val Arg Met
    210                 215                 220
Pro Leu Leu Thr Pro Arg Tyr Ile Thr Asp Val Ile Asp Ala Glu Pro
225                 230                 235                 240
Phe Ile Arg Cys Ser Leu Gln Cys Arg Asp Leu Val Asp Glu Ala Lys
                245                 250                 255
Lys Phe His Leu Arg Pro Glu Leu Arg Ser Gln Met Gln Gly Pro Arg
            260                 265                 270
Thr Arg Ala Arg Leu Gly Ala Asn Glu Val Leu Leu Val Val Gly Gly
        275                 280                 285
Phe Gly Ser Gln Gln Ser Pro Ile Asp Val Val Glu Lys Tyr Asp Pro
    290                 295                 300
Lys Thr Gln Glu Trp Ser Phe Leu Pro Ser Ile Thr Arg Lys Arg Arg
305                 310                 315                 320
Tyr Val Ala Ser Val Ser Leu His Asp Arg Ile Tyr Val Ile Gly Gly
                325                 330                 335
Tyr Asp Gly Arg Ser Arg Leu Ser Ser Val Glu Cys Leu Asp Tyr Thr
            340                 345                 350
Ala Asp Glu Asp Gly Val Trp Tyr Ser Val Ala Pro Met Asn Val Arg
        355                 360                 365
Arg Gly Leu Ala Gly Ala Thr Thr Leu Gly Asp Met Ile Tyr Val Ser
    370                 375                 380
Gly Gly Phe Asp Gly Ser Arg Arg His Thr Ser Met Glu Arg Tyr Asp
385                 390                 395                 400
Pro Asn Ile Asp Gln Trp Ser Met Leu Gly Asp Met Gln Thr Ala Arg
                405                 410                 415
Glu Gly Ala Gly Leu Val Val Ala Ser Gly Val Ile Tyr Cys Leu Gly
            420                 425                 430
Gly Tyr Asp Gly Leu Asn Ile Leu Asn Ser Val Glu Lys Tyr Asp Pro
        435                 440                 445
His Thr Gly His Trp Thr Asn Val Thr Pro Met Ala Thr Lys Arg Ser
    450                 455                 460
Gly Ala Gly Val Ala Leu Leu Asn Asp His Ile Tyr Val Val Gly Gly
465                 470                 475                 480
Phe Asp Gly Thr Ala His Leu Ser Ser Val Glu Ala Tyr Asn Ile Arg
                485                 490                 495
```

```
Thr Asp Ser Trp Thr Thr Val Thr Ser Met Thr Thr Pro Arg Cys Tyr
                500                 505                 510

Val Gly Ala Thr Val Leu Arg Gly Arg Leu Tyr Ala Ile Ala Gly Tyr
                515                 520                 525

Asp Gly Asn Ser Leu Leu Ser Ser Ile Glu Cys Tyr Asp Pro Ile Ile
                530                 535                 540

Asp Ser Trp Glu Val Val Thr Ser Met Gly Thr Gln Arg Cys Asp Ala
545                 550                 555                 560

Gly Val Cys Val Leu Arg Glu Lys
                565

<210> SEQ ID NO 13
<211> LENGTH: 609
<212> TYPE: PRT
<213> ORGANISM: Homo sapiens

<400> SEQUENCE: 13

Met Glu Gly Lys Pro Met Arg Arg Cys Thr Asn Ile Arg Pro Gly Glu
1               5                   10                  15

Thr Gly Met Asp Val Thr Ser Arg Cys Thr Leu Gly Asp Pro Asn Lys
                20                  25                  30

Leu Pro Glu Gly Val Pro Gln Pro Ala Arg Met Pro Tyr Ile Ser Asp
                35                  40                  45

Lys His Pro Arg Gln Thr Leu Glu Val Ile Asn Leu Leu Arg Lys His
        50                  55                  60

Arg Glu Leu Cys Asp Val Val Leu Val Val Gly Ala Lys Lys Ile Tyr
65                  70                  75                  80

Ala His Arg Val Ile Leu Ser Ala Cys Ser Pro Tyr Phe Arg Ala Met
                85                  90                  95

Phe Thr Gly Glu Leu Ala Glu Ser Arg Gln Thr Glu Val Val Ile Arg
                100                 105                 110

Asp Ile Asp Glu Arg Ala Met Glu Leu Leu Ile Asp Phe Ala Tyr Thr
            115                 120                 125

Ser Gln Ile Thr Val Glu Glu Gly Asn Val Gln Thr Leu Leu Pro Ala
        130                 135                 140

Ala Cys Leu Leu Gln Leu Ala Glu Ile Gln Glu Ala Cys Cys Glu Phe
145                 150                 155                 160

Leu Lys Arg Gln Leu Asp Pro Ser Asn Cys Leu Gly Ile Arg Ala Phe
                165                 170                 175

Ala Asp Thr His Ser Cys Arg Glu Leu Leu Arg Ile Ala Asp Lys Phe
            180                 185                 190

Thr Gln His Asn Phe Gln Glu Val Met Glu Ser Glu Glu Phe Met Leu
        195                 200                 205

Leu Pro Ala Asn Gln Leu Ile Asp Ile Ile Ser Ser Asp Glu Leu Asn
    210                 215                 220

Val Arg Ser Glu Glu Gln Val Phe Asn Ala Val Met Ala Trp Val Lys
225                 230                 235                 240

Tyr Ser Ile Gln Glu Arg Arg Pro Gln Leu Pro Gln Val Leu Gln His
                245                 250                 255

Val Arg Leu Pro Leu Leu Ser Pro Lys Phe Leu Val Gly Thr Val Gly
            260                 265                 270

Ser Asp Pro Leu Ile Lys Ser Asp Glu Glu Cys Arg Asp Leu Val Asp
        275                 280                 285

Glu Ala Lys Asn Tyr Leu Leu Leu Pro Gln Glu Arg Pro Leu Met Gln
    290                 295                 300
```

-continued

Gly Pro Arg Thr Arg Pro Arg Lys Pro Ile Arg Cys Gly Glu Val Leu
305                 310                 315                 320

Phe Ala Val Gly Gly Trp Cys Ser Gly Asp Ala Ile Ser Ser Val Glu
            325                 330                 335

Arg Tyr Asp Pro Gln Thr Asn Glu Trp Arg Met Val Ala Ser Met Ser
        340                 345                 350

Lys Arg Arg Cys Gly Val Gly Val Ser Val Leu Asp Asp Leu Leu Tyr
    355                 360                 365

Ala Val Gly Gly His Asp Gly Ser Ser Tyr Leu Asn Ser Val Glu Arg
370                 375                 380

Tyr Asp Pro Lys Thr Asn Gln Trp Ser Ser Asp Val Ala Pro Thr Ser
385                 390                 395                 400

Thr Cys Arg Thr Ser Val Gly Val Ala Val Leu Gly Gly Phe Leu Tyr
            405                 410                 415

Ala Val Gly Gly Gln Asp Gly Val Ser Cys Leu Asn Ile Val Glu Arg
        420                 425                 430

Tyr Asp Pro Lys Glu Asn Lys Trp Thr Arg Val Ala Ser Met Ser Thr
    435                 440                 445

Arg Arg Leu Gly Val Ala Val Ala Val Leu Gly Gly Phe Leu Tyr Ala
450                 455                 460

Val Gly Gly Ser Asp Gly Thr Ser Pro Leu Asn Thr Val Glu Arg Tyr
465                 470                 475                 480

Asn Pro Gln Glu Asn Arg Trp His Thr Ile Ala Pro Met Gly Thr Arg
            485                 490                 495

Arg Lys His Leu Gly Cys Ala Val Tyr Gln Asp Met Ile Tyr Ala Val
        500                 505                 510

Gly Gly Arg Asp Asp Thr Thr Glu Leu Ser Ser Ala Glu Arg Tyr Asn
    515                 520                 525

Pro Arg Thr Asn Gln Trp Ser Pro Val Val Ala Met Thr Ser Arg Arg
530                 535                 540

Ser Gly Val Gly Leu Ala Val Val Asn Gly Gln Leu Met Ala Val Gly
545                 550                 555                 560

Gly Phe Asp Gly Thr Thr Tyr Leu Lys Thr Ile Glu Val Phe Asp Pro
            565                 570                 575

Asp Ala Asn Thr Trp Arg Leu Tyr Gly Gly Met Asn Tyr Arg Arg Leu
        580                 585                 590

Gly Gly Gly Val Gly Val Ile Lys Met Thr His Cys Glu Ser His Ile
    595                 600                 605

Trp

<210> SEQ ID NO 14
<211> LENGTH: 587
<212> TYPE: PRT
<213> ORGANISM: Homo sapiens

<400> SEQUENCE: 14

Met Glu Gly Glu Ser Val Lys Leu Ser Ser Gln Thr Leu Ile Gln Ala
1               5                   10                  15

Gly Asp Asp Glu Lys Asn Gln Arg Thr Ile Thr Val Asn Pro Ala His
            20                  25                  30

Met Gly Lys Ala Phe Lys Val Met Asn Glu Leu Arg Ser Lys Gln Leu
        35                  40                  45

Leu Cys Asp Val Met Ile Val Ala Glu Asp Val Glu Ile Glu Ala His
    50                  55                  60

```
Arg Val Val Leu Ala Ala Cys Ser Pro Tyr Phe Cys Ala Met Phe Thr
65                  70                  75                  80

Gly Asp Met Ser Glu Ser Lys Ala Lys Lys Ile Glu Ile Lys Asp Val
                85                  90                  95

Asp Gly Gln Thr Leu Ser Lys Leu Ile Asp Tyr Ile Tyr Thr Ala Glu
            100                 105                 110

Ile Glu Val Thr Glu Glu Asn Val Gln Val Leu Leu Pro Ala Ala Ser
        115                 120                 125

Leu Leu Gln Leu Met Asp Val Arg Gln Asn Cys Cys Asp Phe Leu Gln
130                 135                 140

Ser Gln Leu His Pro Thr Asn Cys Leu Gly Ile Arg Ala Phe Ala Asp
145                 150                 155                 160

Val His Thr Cys Thr Asp Leu Leu Gln Gln Ala Asn Ala Tyr Ala Glu
                165                 170                 175

Gln His Phe Pro Glu Val Met Leu Gly Glu Glu Phe Leu Ser Leu Ser
            180                 185                 190

Leu Asp Gln Val Cys Ser Leu Ile Ser Ser Asp Lys Leu Thr Val Ser
        195                 200                 205

Ser Glu Glu Lys Val Phe Glu Ala Val Ile Ser Trp Ile Asn Tyr Glu
210                 215                 220

Lys Glu Thr Arg Leu Glu His Met Ala Lys Leu Met Glu His Val Arg
225                 230                 235                 240

Leu Pro Leu Leu Pro Arg Asp Tyr Leu Val Gln Thr Val Glu Glu Glu
                245                 250                 255

Ala Leu Ile Lys Asn Asn Asn Thr Cys Lys Asp Phe Leu Ile Glu Ala
            260                 265                 270

Met Lys Tyr His Leu Leu Pro Leu Asp Gln Arg Leu Leu Ile Lys Asn
        275                 280                 285

Pro Arg Thr Lys Pro Arg Thr Pro Val Ser Leu Pro Lys Val Met Ile
290                 295                 300

Val Val Gly Gly Gln Ala Pro Lys Ala Ile Arg Ser Val Glu Cys Tyr
305                 310                 315                 320

Asp Phe Glu Glu Asp Arg Trp Asp Gln Ile Ala Glu Leu Pro Ser Arg
                325                 330                 335

Arg Cys Arg Ala Gly Val Val Phe Met Ala Gly His Val Tyr Ala Val
            340                 345                 350

Gly Gly Phe Asn Gly Ser Leu Arg Val Arg Thr Val Asp Val Tyr Asp
        355                 360                 365

Gly Val Lys Asp Gln Trp Thr Ser Ile Ala Ser Met Gln Glu Arg Arg
370                 375                 380

Ser Thr Leu Gly Ala Ala Val Leu Asn Asp Leu Leu Tyr Ala Val Gly
385                 390                 395                 400

Gly Phe Asp Gly Ser Thr Gly Leu Ala Ser Val Glu Ala Tyr Ser Tyr
                405                 410                 415

Lys Thr Asn Glu Trp Phe Phe Val Ala Pro Met Asn Thr Arg Arg Ser
            420                 425                 430

Ser Val Gly Val Gly Val Val Glu Gly Lys Leu Tyr Ala Val Gly Gly
        435                 440                 445

Tyr Asp Gly Ala Ser Arg Gln Cys Leu Ser Thr Val Glu Gln Tyr Asn
450                 455                 460

Pro Ala Thr Asn Glu Trp Ile Tyr Val Ala Asp Met Ser Thr Arg Arg
465                 470                 475                 480
```

```
Ser Gly Ala Gly Val Gly Val Leu Ser Gly Gln Leu Tyr Ala Thr Gly
                485                 490                 495

Gly His Asp Gly Pro Leu Val Arg Lys Ser Val Glu Val Tyr Asp Pro
            500                 505                 510

Gly Thr Asn Thr Trp Lys Gln Val Ala Asp Met Asn Met Cys Arg Arg
            515                 520                 525

Asn Ala Gly Val Cys Ala Val Asn Gly Leu Leu Tyr Val Val Gly Gly
            530                 535                 540

Asp Asp Gly Ser Cys Asn Leu Ala Ser Val Glu Tyr Tyr Asn Pro Val
545                 550                 555                 560

Thr Asp Lys Trp Thr Leu Leu Pro Thr Asn Met Ser Thr Gly Arg Ser
                565                 570                 575

Tyr Ala Gly Val Ala Val Ile His Lys Ser Leu
            580                 585

<210> SEQ ID NO 15
<211> LENGTH: 642
<212> TYPE: PRT
<213> ORGANISM: Homo sapiens

<400> SEQUENCE: 15

Met Gln Pro Arg Ser Glu Arg Pro Ala Gly Arg Thr Gln Ser Pro Glu
1               5                   10                  15

His Gly Ser Pro Gly Pro Gly Pro Glu Ala Pro Pro Pro Pro Pro Pro
            20                  25                  30

Gln Pro Pro Ala Pro Glu Ala Glu Arg Thr Arg Pro Arg Gln Ala Arg
            35                  40                  45

Pro Ala Ala Pro Met Glu Gly Ala Val Gln Leu Leu Ser Arg Glu Gly
50                  55                  60

His Ser Val Ala His Asn Ser Lys Arg His Tyr His Asp Ala Phe Val
65                  70                  75                  80

Ala Met Ser Arg Met Arg Gln Arg Gly Leu Leu Cys Asp Ile Val Leu
                85                  90                  95

His Val Ala Ala Lys Glu Ile Arg Ala His Lys Val Val Leu Ala Ser
            100                 105                 110

Cys Ser Pro Tyr Phe His Ala Met Phe Thr Asn Glu Met Ser Glu Ser
            115                 120                 125

Arg Gln Thr His Val Thr Leu His Asp Ile Asp Pro Gln Ala Leu Asp
            130                 135                 140

Gln Leu Val Gln Phe Ala Tyr Thr Ala Glu Ile Val Val Gly Glu Gly
145                 150                 155                 160

Asn Val Gln Thr Leu Leu Pro Ala Ala Ser Leu Leu Gln Leu Asn Gly
                165                 170                 175

Val Arg Asp Ala Cys Cys Lys Phe Leu Leu Ser Gln Leu Asp Pro Ser
            180                 185                 190

Asn Cys Leu Gly Ile Arg Gly Phe Ala Asp Ala His Ser Cys Ser Asp
            195                 200                 205

Leu Leu Lys Ala Ala His Arg Tyr Val Leu Gln His Phe Val Asp Val
            210                 215                 220

Ala Lys Thr Glu Glu Phe Met Leu Leu Pro Leu Lys Gln Val Leu Glu
225                 230                 235                 240

Leu Val Ser Ser Asp Ser Leu Asn Val Pro Ser Glu Glu Val Tyr
                245                 250                 255

Arg Ala Val Leu Ser Trp Val Lys His Asp Val Asp Ala Arg Arg Gln
            260                 265                 270
```

```
His Val Pro Arg Leu Met Lys Cys Val Arg Leu Pro Leu Leu Ser Arg
            275                 280                 285

Asp Phe Leu Leu Gly His Val Asp Ala Glu Ser Leu Val Arg His His
            290                 295                 300

Pro Asp Cys Lys Asp Leu Leu Ile Glu Ala Leu Lys Phe His Leu Leu
305                 310                 315                 320

Pro Glu Gln Arg Gly Val Leu Gly Thr Ser Arg Thr Arg Pro Arg Arg
                    325                 330                 335

Cys Glu Gly Ala Gly Pro Val Leu Phe Ala Val Gly Gly Ser Leu
                    340                 345                 350

Phe Ala Ile His Gly Asp Cys Glu Ala Tyr Asp Thr Thr Asp Arg
            355                 360                 365

Trp His Val Ala Ser Met Ser Thr Arg Arg Ala Arg Val Gly Val
            370                 375                 380

Ala Ala Val Gly Asn Arg Leu Tyr Ala Val Gly Gly Tyr Asp Gly Thr
385                 390                 395                 400

Ser Asp Leu Ala Thr Val Glu Ser Tyr Asp Pro Val Thr Asn Thr Trp
                    405                 410                 415

Gln Pro Glu Val Ser Met Gly Thr Arg Arg Ser Cys Leu Gly Val Ala
                    420                 425                 430

Ala Leu His Gly Leu Leu Tyr Ser Ala Gly Gly Tyr Asp Gly Ala Ser
            435                 440                 445

Cys Leu Asn Ser Ala Glu Arg Tyr Asp Pro Leu Thr Gly Thr Trp Thr
            450                 455                 460

Ser Val Ala Ala Met Ser Thr Arg Arg Tyr Val Arg Val Ala Thr
465                 470                 475                 480

Leu Asp Gly Asn Leu Tyr Ala Val Gly Gly Tyr Asp Ser Ser Ser His
                    485                 490                 495

Leu Ala Thr Val Glu Lys Tyr Glu Pro Gln Val Asn Val Trp Ser Pro
            500                 505                 510

Val Ala Ser Met Leu Ser Arg Arg Ser Ser Ala Gly Val Ala Val Leu
            515                 520                 525

Glu Gly Ala Leu Tyr Val Ala Gly Gly Asn Asp Gly Thr Ser Cys Leu
            530                 535                 540

Asn Ser Val Glu Arg Tyr Ser Pro Lys Ala Gly Ala Trp Glu Ser Val
545                 550                 555                 560

Ala Pro Met Asn Ile Arg Arg Ser Thr His Asp Leu Val Ala Met Asp
                565                 570                 575

Gly Trp Leu Tyr Ala Val Gly Gly Asn Asp Gly Ser Ser Ser Leu Asn
            580                 585                 590

Ser Ile Glu Lys Tyr Asn Pro Arg Thr Asn Lys Trp Val Ala Ala Ser
            595                 600                 605

Cys Met Phe Thr Arg Arg Ser Ser Val Gly Val Ala Val Leu Glu Leu
            610                 615                 620

Leu Asn Phe Pro Pro Ser Ser Pro Thr Leu Ser Val Ser Ser Thr
625                 630                 635                 640

Ser Leu

<210> SEQ ID NO 16
<211> LENGTH: 597
<212> TYPE: PRT
<213> ORGANISM: Homo sapiens

<400> SEQUENCE: 16
```

```
Met Val Trp Leu Glu Ala Arg Pro Gln Ile Leu Phe Val Cys Thr Lys
1               5                   10                  15

Gln Gly His Gln Lys Pro Leu Asp Ser Lys Asp Asn Thr Glu Lys
            20                  25                  30

His Cys Pro Val Thr Val Asn Pro Trp His Met Lys Lys Ala Phe Lys
            35                  40                  45

Val Met Asn Glu Leu Arg Ser Gln Asn Leu Leu Cys Asp Val Thr Ile
50                  55                  60

Val Ala Glu Asp Met Glu Ile Ser Ala His Arg Val Val Leu Ala Ala
65                  70                  75                  80

Cys Ser Pro Tyr Phe His Ala Met Phe Thr Gly Glu Met Ser Glu Ser
                85                  90                  95

Arg Ala Lys Arg Val Arg Ile Lys Glu Val Asp Gly Trp Thr Leu Arg
            100                 105                 110

Met Leu Ile Asp Tyr Val Tyr Thr Ala Glu Ile Gln Val Thr Glu Glu
            115                 120                 125

Asn Val Gln Val Leu Leu Pro Ala Ala Gly Leu Leu Gln Leu Gln Asp
130                 135                 140

Val Lys Lys Thr Cys Cys Glu Phe Leu Glu Ser Gln Leu His Pro Val
145                 150                 155                 160

Asn Cys Leu Gly Ile Arg Ala Phe Ala Asp Met His Ala Cys Thr Asp
            165                 170                 175

Leu Leu Asn Lys Ala Asn Thr Tyr Ala Glu Gln His Phe Ala Asp Val
            180                 185                 190

Val Leu Ser Glu Glu Phe Leu Asn Leu Gly Ile Glu Gln Val Cys Ser
            195                 200                 205

Leu Ile Ser Ser Asp Lys Leu Thr Ile Ser Ser Glu Glu Lys Val Phe
            210                 215                 220

Glu Ala Val Ile Ala Trp Val Asn His Asp Lys Asp Val Arg Gln Glu
225                 230                 235                 240

Phe Met Ala Arg Leu Met Glu His Val Arg Leu Pro Leu Leu Pro Arg
            245                 250                 255

Glu Tyr Leu Val Gln Arg Val Glu Glu Glu Ala Leu Val Lys Asn Ser
            260                 265                 270

Ser Ala Cys Lys Asp Tyr Leu Ile Glu Ala Met Lys Tyr His Leu Leu
            275                 280                 285

Pro Thr Glu Gln Arg Ile Leu Met Lys Ser Val Arg Thr Arg Leu Arg
            290                 295                 300

Thr Pro Met Asn Leu Pro Lys Leu Met Val Val Gly Gly Gln Ala
305                 310                 315                 320

Pro Lys Ala Ile Arg Ser Val Glu Cys Tyr Asp Phe Lys Glu Glu Arg
            325                 330                 335

Trp His Gln Val Ala Glu Leu Pro Ser Arg Arg Cys Arg Ala Gly Met
            340                 345                 350

Val Tyr Met Ala Gly Leu Val Phe Ala Val Gly Gly Phe Asn Gly Ser
            355                 360                 365

Leu Arg Val Arg Thr Val Asp Ser Tyr Asp Pro Val Lys Asp Gln Trp
            370                 375                 380

Thr Ser Val Ala Asn Met Arg Asp Arg Arg Ser Thr Leu Gly Ala Ala
385                 390                 395                 400

Val Leu Asn Gly Leu Leu Tyr Ala Val Gly Gly Phe Asp Gly Ser Thr
            405                 410                 415
```

```
Gly Leu Ser Ser Val Glu Ala Tyr Asn Ile Lys Ser Asn Glu Trp Phe
            420                 425                 430

His Val Ala Pro Met Asn Thr Arg Arg Ser Ser Val Gly Val Gly Val
            435                 440                 445

Val Gly Gly Leu Leu Tyr Ala Val Gly Tyr Asp Gly Ala Ser Arg
450                 455                 460

Gln Cys Leu Ser Thr Val Glu Cys Tyr Asn Ala Thr Thr Asn Glu Trp
465                 470                 475                 480

Thr Tyr Ile Ala Glu Met Ser Thr Arg Arg Ser Gly Ala Gly Val Gly
            485                 490                 495

Val Leu Asn Asn Leu Leu Tyr Ala Val Gly Gly His Asp Gly Pro Leu
            500                 505                 510

Val Arg Lys Ser Val Glu Val Tyr Asp Pro Thr Thr Asn Ala Trp Arg
            515                 520                 525

Gln Val Ala Asp Met Asn Met Cys Arg Arg Asn Ala Gly Val Cys Ala
            530                 535                 540

Val Asn Gly Leu Leu Tyr Val Val Gly Gly Asp Asp Gly Ser Cys Asn
545                 550                 555                 560

Leu Ala Ser Val Glu Tyr Tyr Asn Pro Thr Thr Asp Lys Trp Thr Val
            565                 570                 575

Val Ser Ser Cys Met Ser Thr Gly Arg Ser Tyr Ala Gly Val Thr Val
            580                 585                 590

Ile Asp Lys Pro Leu
            595

<210> SEQ ID NO 17
<211> LENGTH: 593
<212> TYPE: PRT
<213> ORGANISM: Homo sapiens

<400> SEQUENCE: 17

Met Glu Thr Pro Pro Leu Pro Pro Ala Cys Thr Lys Gln Gly His Gln
1               5                   10                  15

Lys Pro Leu Asp Ser Lys Asp Asp Asn Thr Glu Lys His Cys Pro Val
            20                  25                  30

Thr Val Asn Pro Trp His Met Lys Lys Ala Phe Lys Val Met Asn Glu
        35                  40                  45

Leu Arg Ser Gln Asn Leu Leu Cys Asp Val Thr Ile Val Ala Glu Asp
    50                  55                  60

Met Glu Ile Ser Ala His Arg Val Val Leu Ala Ala Cys Ser Pro Tyr
65                  70                  75                  80

Phe His Ala Met Phe Thr Gly Glu Met Ser Glu Ser Arg Ala Lys Arg
                85                  90                  95

Val Arg Ile Lys Glu Val Asp Gly Trp Thr Leu Arg Met Leu Ile Asp
            100                 105                 110

Tyr Val Tyr Thr Ala Glu Ile Gln Val Thr Glu Glu Asn Val Gln Val
        115                 120                 125

Leu Leu Pro Ala Ala Gly Leu Leu Gln Leu Gln Asp Val Lys Lys Thr
    130                 135                 140

Cys Cys Glu Phe Leu Glu Ser Gln Leu His Pro Val Asn Cys Leu Gly
145                 150                 155                 160

Ile Arg Ala Phe Ala Asp Met His Ala Cys Thr Asp Leu Leu Asn Lys
                165                 170                 175

Ala Asn Thr Tyr Ala Glu Gln His Phe Ala Asp Val Val Leu Ser Glu
            180                 185                 190
```

-continued

```
Glu Phe Leu Asn Leu Gly Ile Glu Gln Val Cys Ser Leu Ile Ser Ser
                195                 200                 205

Asp Lys Leu Thr Ile Ser Ser Glu Glu Lys Val Phe Glu Ala Val Ile
210                 215                 220

Ala Trp Val Asn His Asp Lys Asp Val Arg Gln Glu Phe Met Ala Arg
225                 230                 235                 240

Leu Met Glu His Val Arg Leu Pro Leu Pro Arg Glu Tyr Leu Val
                245                 250                 255

Gln Arg Val Glu Glu Ala Leu Val Lys Asn Ser Ser Ala Cys Lys
                260                 265                 270

Asp Tyr Leu Ile Glu Ala Met Lys Tyr His Leu Leu Pro Thr Glu Gln
                275                 280                 285

Arg Ile Leu Met Lys Ser Val Arg Thr Arg Leu Arg Thr Pro Met Asn
290                 295                 300

Leu Pro Lys Leu Met Val Val Gly Gln Ala Pro Lys Ala Ile
305                 310                 315                 320

Arg Ser Val Glu Cys Tyr Asp Phe Lys Glu Glu Arg Trp His Gln Val
                325                 330                 335

Ala Glu Leu Pro Ser Arg Arg Cys Arg Ala Gly Met Val Tyr Met Ala
                340                 345                 350

Gly Leu Val Phe Ala Val Gly Gly Phe Asn Gly Ser Leu Arg Val Arg
                355                 360                 365

Thr Val Asp Ser Tyr Asp Pro Val Lys Asp Gln Trp Thr Ser Val Ala
                370                 375                 380

Asn Met Arg Asp Arg Arg Ser Thr Leu Gly Ala Ala Val Leu Asn Gly
385                 390                 395                 400

Leu Leu Tyr Ala Val Gly Gly Phe Asp Gly Ser Thr Gly Leu Ser Ser
                405                 410                 415

Val Glu Ala Tyr Asn Ile Lys Ser Asn Glu Trp Phe His Val Ala Pro
                420                 425                 430

Met Asn Thr Arg Arg Ser Ser Val Gly Val Gly Val Val Gly Gly Leu
                435                 440                 445

Leu Tyr Ala Val Gly Gly Tyr Asp Gly Ala Ser Arg Gln Cys Leu Ser
450                 455                 460

Thr Val Glu Cys Tyr Asn Ala Thr Thr Asn Glu Trp Thr Tyr Ile Ala
465                 470                 475                 480

Glu Met Ser Thr Arg Arg Ser Gly Ala Gly Val Gly Val Leu Asn Asn
                485                 490                 495

Leu Leu Tyr Ala Val Gly Gly His Asp Gly Pro Leu Val Arg Lys Ser
                500                 505                 510

Val Glu Val Tyr Asp Pro Thr Thr Asn Ala Trp Arg Gln Val Ala Asp
                515                 520                 525

Met Asn Met Cys Arg Arg Asn Ala Gly Val Cys Ala Val Asn Gly Leu
530                 535                 540

Leu Tyr Val Val Gly Gly Asp Asp Gly Ser Cys Asn Leu Ala Ser Val
545                 550                 555                 560

Glu Tyr Tyr Asn Pro Thr Thr Asp Lys Trp Thr Val Val Ser Ser Cys
                565                 570                 575

Met Ser Thr Gly Arg Ser Tyr Ala Gly Val Thr Val Ile Asp Lys Pro
                580                 585                 590

Leu
```

```
<210> SEQ ID NO 18
<211> LENGTH: 574
<212> TYPE: PRT
<213> ORGANISM: Homo sapiens

<400> SEQUENCE: 18

Met Val Glu Asp Gly Ala Glu Leu Glu Asp Leu Val His Phe Ser
1               5                   10                  15

Val Ser Glu Leu Pro Ser Arg Gly Tyr Gly Val Met Glu Glu Ile Arg
            20                  25                  30

Arg Gln Gly Lys Leu Cys Asp Val Thr Leu Lys Ile Gly Asp His Lys
            35                  40                  45

Phe Ser Ala His Arg Ile Val Leu Ala Ala Ser Ile Pro Tyr Phe His
        50                  55                  60

Ala Met Phe Thr Asn Asp Met Met Glu Cys Lys Gln Asp Glu Ile Val
65                  70                  75                  80

Met Gln Gly Met Asp Pro Ser Ala Leu Glu Ala Leu Ile Asn Phe Ala
                85                  90                  95

Tyr Asn Gly Asn Leu Ala Ile Asp Gln Gln Asn Val Gln Ser Leu Leu
            100                 105                 110

Met Gly Ala Ser Phe Leu Gln Leu Gln Ser Ile Lys Asp Ala Cys Cys
        115                 120                 125

Thr Phe Leu Arg Glu Arg Leu His Pro Lys Asn Cys Leu Gly Val Arg
130                 135                 140

Gln Phe Ala Glu Thr Met Met Cys Ala Val Leu Tyr Asp Ala Ala Asn
145                 150                 155                 160

Ser Phe Ile His Gln His Phe Val Glu Val Ser Met Ser Glu Glu Phe
                165                 170                 175

Leu Ala Leu Pro Leu Glu Asp Val Leu Glu Leu Val Ser Arg Asp Glu
            180                 185                 190

Leu Asn Val Lys Ser Glu Glu Gln Val Phe Glu Ala Ala Leu Ala Trp
        195                 200                 205

Val Arg Tyr Asp Arg Glu Gln Arg Gly Pro Tyr Leu Pro Glu Leu Leu
210                 215                 220

Ser Asn Ile Arg Leu Pro Leu Cys Arg Pro Gln Phe Leu Ser Asp Arg
225                 230                 235                 240

Val Gln Gln Asp Asp Leu Val Arg Cys Cys His Lys Cys Arg Asp Leu
                245                 250                 255

Val Asp Glu Ala Lys Asp Tyr His Leu Met Pro Glu Arg Arg Pro His
            260                 265                 270

Leu Pro Ala Phe Arg Thr Arg Pro Arg Cys Cys Thr Ser Ile Ala Gly
        275                 280                 285

Leu Ile Tyr Ala Val Gly Gly Leu Asn Ser Ala Gly Asp Ser Leu Asn
290                 295                 300

Val Val Glu Val Phe Asp Pro Ile Ala Asn Cys Trp Glu Arg Cys Arg
305                 310                 315                 320

Pro Met Thr Thr Ala Arg Ser Arg Val Gly Val Ala Val Asn Gly
                325                 330                 335

Leu Leu Tyr Ala Ile Gly Gly Tyr Asp Gly Gln Leu Arg Leu Ser Thr
            340                 345                 350

Val Glu Ala Tyr Asn Pro Glu Thr Asp Thr Trp Thr Arg Val Gly Ser
        355                 360                 365

Met Asn Ser Lys Arg Ser Ala Met Gly Thr Val Val Leu Asp Gly Gln
370                 375                 380
```

-continued

```
Ile Tyr Val Cys Gly Gly Tyr Asp Gly Asn Ser Ser Leu Ser Ser Val
385                 390                 395                 400

Glu Thr Tyr Ser Pro Glu Thr Asp Lys Trp Thr Val Val Thr Ser Met
                405                 410                 415

Ser Ser Asn Arg Ser Ala Ala Gly Val Thr Val Phe Glu Gly Arg Ile
            420                 425                 430

Tyr Val Ser Gly Gly His Asp Gly Leu Gln Ile Phe Ser Ser Val Glu
        435                 440                 445

His Tyr Asn His His Thr Ala Thr Trp His Pro Ala Ala Gly Met Leu
    450                 455                 460

Asn Lys Arg Cys Arg His Gly Ala Ala Ser Leu Gly Ser Lys Met Phe
465                 470                 475                 480

Val Cys Gly Gly Tyr Asp Gly Ser Gly Phe Leu Ser Ile Ala Glu Met
                485                 490                 495

Tyr Ser Ser Val Ala Asp Gln Trp Cys Leu Ile Val Pro Met His Thr
            500                 505                 510

Arg Arg Ser Arg Val Ser Leu Val Ala Ser Cys Gly Arg Leu Tyr Ala
            515                 520                 525

Val Gly Gly Tyr Asp Gly Gln Ser Asn Leu Ser Ser Val Glu Met Tyr
        530                 535                 540

Asp Pro Glu Thr Asp Cys Trp Thr Phe Met Ala Pro Met Ala Cys His
545                 550                 555                 560

Glu Gly Gly Val Gly Val Gly Cys Ile Pro Leu Leu Thr Ile
                565                 570

<210> SEQ ID NO 19
<211> LENGTH: 11
<212> TYPE: PRT
<213> ORGANISM: Artificial Sequence
<220> FEATURE:
<223> OTHER INFORMATION: Synthetic

<400> SEQUENCE: 19

Tyr Thr Asp Ile Glu Met Asn Arg Leu Gly Lys
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Synthetic

<400> SEQUENCE: 20

Gln Pro Glu Leu Ala Pro Glu Asp Pro Glu Asp
1               5                   10
```

METHOD FOR DIAGNOSING PRIMARY BILIARY CIRRHOSIS (PBC) USING NOVEL AUTOANTIGENS

GOVERNMENT LICENSE RIGHTS

This invention was made with government support under R44 AI052525 awarded by the National Institutes of Health. The government has certain rights in this invention.

FIELD OF THE INVENTION

This invention relates to molecular biology, biochemistry, cell biology, medicine and medical diagnostics. Specifically, the invention relates to novel nucleic acid molecules, proteins and polypeptide fragments encoded thereby, polyclonal and monoclonal antibodies thereto, and methods of using the nucleic acid molecules, proteins/polypeptides and antibodies in diagnostic, prognostic, staging and therapeutic regimens for the control of autoimmune disorders, viral diseases and cancers.

BACKGROUND OF THE INVENTION

More than 80 illnesses have been described that are associated with activation of auto-reactive lymphocytes and the production of autoantibodies directed against normal tissue or cellular components (autoantigens) [von Muhlen and Tan (1995) Semin Arthritis Rheum 24: 323-58; Mellors (2002) 2005]. Collectively referred to as autoimmune diseases, they are estimated to afflict 14.7-23.5 million people, up to 8% of the total U.S. population and constitute a major economic and health burden [Jacobson, Gange, Rose and Graham (1997) Clin Immunol Immunopathol 84: 223-43]. For unknown reasons, the number of people afflicted by autoimmune diseases is on the rise. An autoimmune diagnosis means a lifetime of illness and treatment, possible organ damage, debilitation and an increased chance of mortality. The chronic and often debilitating nature of autoimmune diseases results in poor patient health, increased medical costs, and decreased productivity. The root causes of the immune dysfunction underpinning autoimmune disease are still not well understood. Consequently, autoimmune diseases generally remain difficult to diagnose, due to the wide variability of clinical presentation, which typically involves a constellation of symptoms.

Autoimmune diseases are disorders in which an individual's immune system targets and destroys apparently normal tissue. Examples of autoimmune diseases include rheumatoid arthritis (RA), systemic lupus erythematosus (SLE), scleroderma (SCL), Sjogren's syndrome (SjS), polymyositis (PM), dermatomyositis (DM), mixed connective tissue disease (MCTD), pemphigus vulgaris (PV) and primary biliary cirrhosis (PBC). Autoantibodies are commonly directed against cellular proteins and nucleic acids. In certain diseases, such as PV, the target of autoantibodies is known and the autoantibody is thought to play a role in the pathogenesis of the disease. In other diseases, such as SLE, the targets of many different autoantibodies have been identified but the role of autoantibodies in the pathogenesis of SLE is as yet uncertain.

Detection of autoantibodies in the serum of patients assists in the diagnosis of autoimmune diseases. Rheumatoid factor (IgM antibodies directed against human IgG) is detected in the majority of patients with RA and supports that diagnosis in a given individual [Kelly, W. N., et al. 1985. Textbook of Rheumatology. 2nd ed. Saunders. pp. 667]. Antinuclear antibodies (ANA) are present in approximately 98% of individuals with active SLE. Although ANA are not specific for the diagnosis of SLE, the absence of these antibodies argues against the diagnosis of SLE in a given patient [Kelly et al., 1985 supra pp. 691].

Liver and biliary diseases collectively rank in the top ten causes of mortality in the U.S. Chronic liver diseases affect between 5 and 10 percent of Americans and cause 1 to 2 percent of deaths in the United States. Chronic liver disease and cirrhosis cost an estimated $1.6 billion per year [(2004)]. General causes of liver and biliary diseases include infectious agents, inherited defects, metabolic disturbances, alcohol, toxins and environmental toxicants. The most common liver diseases are chronic hepatitis C, alcohol liver disease, nonalcoholic fatty liver disease, chronic hepatitis B, autoimmune liver diseases and drug-induced liver diseases. Many of these conditions can be prevented or treated, but if not, they can lead to progressive liver injury, liver fibrosis and ultimately cirrhosis, portal hypertension, end-stage liver disease and, in some instances, liver cancer. Currently, the only therapy for end-stage liver disease is liver transplantation. More than 5,000 liver transplants are done in the U.S. each year. At least 17,000 persons are on a waiting list for liver transplantation and as many as 1,500 die yearly while waiting [(2004)]. Liver disease research presents many challenging needs. Autoimmune liver diseases include primary biliary cirrhosis (PBC), autoimmune hepatitis and primary sclerosing cholangitis. These chronic liver diseases can all lead to end-stage liver disease. Collectively, autoimmune liver diseases are responsible for 13% of adult liver transplants per year in the U.S. [(2004)].

PBC is a progressive cholestatic liver disease, with an estimated prevalence in the U.S. of approximately 40 adults per 100,000 population (incidence 2.7 per 100,000 U.S. population) [Kim, Lindor et al. (2000) Gastroenterology 119: 1631-6; Feld and Heathcote (2003) J Gastroenterol Hepatol 18: 1118-28; 2004)]. Women between the ages of 40 and 65 are predominantly affected by PBC, with a female to male ratio of 9:1 [Kaplan and Gershwin (2005) N Engl J Med 353: 1261-73], as is typical for autoimmune disease. PBC is characterized by the gradual progressive destruction of intrahepatic biliary ductules leading to hepatic fibrosis and liver failure (reviewed in [Kaplan (1996) N Engl J Med 335: 1570-80; Heathcote (2000) Hepatology 31: 1005-13; Kaplan (2002) Gastroenterology 123: 1392-4; Talwalkar and Lindor (2003) Lancet 362: 53-61]). PBC is a significant indication for liver transplantation, and PBC patients constitute 11% of all patients undergoing liver transplantation for cirrhosis [Milkiewicz (2008) Clin Liver Dis 12: 461-72; xi].

Treatment of PBC is accomplished with ursodeoxycholic acid (ursodiol), a natural bile acid that is not toxic to the liver, to replace the bile acids which are reduced by PBC. While the mechanisms are not fully understood, this treatment ultimately reduces intracellular build up of other liver-toxic bile acids (which was caused by bile duct destruction). Although ursodiol slows progression to cirrhosis, ursodiol treatment functions best when implemented early in the course of PBC, highlighting the importance of a rapid, reliable PBC diagnostic test. In fact, a study showed that ursodiol treatment at stages III and IV did not result in significant slowing of liver progression while patients treated early at histological stages I and II did show significant slowing of liver destruction with ursodiol treatment. This highlights the need for an early PBC diagnostic, to allow prompt medical treatment [Heathcote (2000) Hepatology 31: 1005-13; Poupon, Lindor, Pares, Chazouilleres, Poupon and Heathcote (2003) J Hepatol 39: 12-6].

Roughly half of PBC patients first present with an abnormal blood test which triggers the eventual PBC diagnosis. Generally, diagnostic testing is initially activated by abnormal liver function tests and signs of bile disease, followed by testing for serum anti-mitochondrial autoantibodies (AMA), for which an estimated 87-95% of PBC patients test positive [Heathcote (2000) Hepatology 31: 1005-13; Yang, Yu, Nakajima, Neuberg, Lindor and Bloch (2004) Clin Gastroenterol Hepatol 2: 1116-22; Kaplan and Gershwin (2005) N Engl J Med 353: 1261-73; Liu, Shi, Zhang, Zhang and Gao (2008) Liver Int 28: 233-9]. Bile duct imaging tests are used to rule out other causes of biliary tract disease, and liver biopsies confirm diagnosis and provide a gauge of disease stage (based upon the degree of fibrosis).

However, the other roughly half of PBC patients will present only with a variety of relatively non-specific physical symptoms, highlighting the difficulties facing the general practitioner or specialist responsible for diagnosis. The most common of such symptoms are pruritis, fatigue and musculoskeletal pain [Prince, Chetwynd, Newman, Metcalf and James (2002) Gastroenterology 123: 1044-51]. Furthermore, numerous autoimmune disorders may be found in association with PBC, including autoimmune hepatitis (AIH) [Czaja (2006) J Hepatol 44: 251-2], thyroid dysfunction, sicca symptoms, Raynaud's syndrome, systemic lupus erythematosus (SLE) and rheumatoid arthritis [Heathcote (2000) Hepatology 31: 1005-13; Gershwin, Selmi, Worman, Gold, Watnik, Utts, Lindor, Kaplan and Vierling (2005) Hepatology 42: 1194-202]. In one study, 19% of PBC patients were found to have features of another disease [Czaja (1998) Hepatology 28: 360-5], thereby clouding diagnosis. Of concern, the proper testing may not be ordered in many patients due to unrecognized etiology, especially when patients present with vague symptoms of pruritis or joint discomfort.

Autoantibodies have the potential to serve not only as diagnostic tools, but also as harbingers of the future development of PBC. In fact, anti-mitochondrial autoantibodies (AMA) have been shown to pre-date clinical manifestations and diagnosis of PBC [Metcalf, Mitchison, Palmer, Jones, Bassendine and James (1996) Lancet 348: 1399-402]. This demonstrates that it may be possible to diagnose PBC at an earlier stage using autoantibody biomarkers. The serological hallmark of PBC are AMA, which can be detected in 87-95% of patients [Kaplan (1996) N Engl J Med 335: 1570-80; Nishio, Keeffe and Gershwin (2002) Semin Liver Dis 22: 291-3021. The major autoantigens targeted by these AMA include the E2 subunits of the pyruvate dehydrogenase complex (PDC-E2), the branched/chain 2-oxo-acid dehydrogenase complex (BCOADC-E2) and the 2-oxo-glutarate dehydrogenase complex (OGDC-E2) [Fussey, Guest, James, Bassendine and Yeaman (1988) Proc Natl Acad Sci USA 85: 8654-8; Nishio, Keeffe et al. (2002) Semin Liver Dis 22: 291-302].

Anti-nuclear autoantibodies (ANA) are present in ~50% of PBC patients. Autoantibodies recognizing proteins of the nuclear core complex and multiple nuclear dots (MND) are useful PBC markers in AMA-negative patients, with a prevalence of 13-44% [Manuel Lucena, Montes Cano, Luis Caro, Respaldiza, Alvarez, Sanchez-Roman, Nunez-Roldan and Wichmann (2007) Ann N Y Acad Sci 1109: 203-11]. Additionally, ANA can serve as prognostic indicators, with anti-centromere and/or anti-nuclear pore glycoprotein 210 (gp210) autoantibodies being associated with liver failure in PBC [Yang, Yu et al. (2004) Clin Gastroenterol Hepatol 2: 1116-22; Nakamura, Kondo et al. (2007) Hepatology 45: 118-27].

The nuclear body (NB, also known as nuclear domain 10, PML oncogenic domain, and Kr body) is a nuclear organelle whose function is unknown [Ascoli, C. A., and Maul, G. G., J. Cell. Biol. 112:785-795 (1991); Brasch, K., and Ochs, R. L., Exp. Cell Res. 202:211-223 (1992); Dyck, J. A. et al., Cell 76:333-343 (1994)]. Using immunohistochemical staining, NBs appear as 5 to 30 discrete, punctate, dot-like regions within the nucleus. The NB is distinct from other nuclear domains including those involved in DNA replication and mRNA processing. In addition, components of the NB do not co-localize with kinetochores or centromeres [Brasch, K., and Ochs, R. L., Exp. Cell Res. 202:211-223 (1992)]. The number of NBs in the cell, and the intensity of antibody staining of these structures, increase in response to stimuli including interferons (IFNs), heat shock and viral infection [Ascoli, C. A., and Maul, G. G., J. Cell. Biol. 112:785-795 (1991)].

The NB is a target of autoantibodies in the serum of patients with the autoimmune disease primary biliary cirrhosis (PBC). Approximately 40% of patients with PBC have antibodies directed against this structure [Evans, J., et al., Arthr. Rheum. 347:31-736 (1991); Szostecki, C. et al., Scand. J. Immunol. 36:555-564 (1992)]. Serum from patients with PBC was used to identify and characterize a 100-kDa component of the NB which was designated Sp100 (Speckled, 100 kDa) [Szostecki, C. et al., J. Immunol. 145:4338-4347 (1990)]. The fusion of Sp100 to the LexA DNA binding domain has been shown to activate gene transcription in *Saccharomyces cerevisiae*, and it has been suggested that Sp100 may participate in activation of transcription of specific regions in the genome [Xie, K. et al., Mol. Cell. Biol. 13:6170-6179 (1993)].

A second component of the NB, designated NDP52, was characterized using a murine monoclonal antibody that reacted with the NB [Korioth, F., et al., J. Cell. Biol. 130:1-13 (1995)]. A cDNA encoding NDP52 was identified and the predicted amino acid sequence contained coiled coil, leucine zipper and zinc finger motifs. One or more of these domains may be involved in interactions between NDP52 and other components of the NB [Korioth, F., et al., J. Cell. Biol. 130: 1-13 (1995)].

A third component of the NB, PML, was identified by several investigators studying the t(15;17) translocation associated with human acute promyelocytic leukemia (APL) [de The, H. et al., Nature (London) 347:558-561 (1990); Borrow, J. et al., Science 249:1577-1580 (1990); Longo, L. et al., J. Exp. Med. 172:1571-1575 (1990); Kakizuka, A. et al., Cell 66:663-674 (1991)]. In this translocation, the amino terminal portion of PML is fused to retinoic acid receptor alpha. PML was found to co-localize with Sp100 in the NB [Weis, K. et al., Cell 76:345-356 (1994); Koken, M. H. M. et al., EMBO 13:1073-1083 (1994)]. Expression of the PML-alpha fusion protein in APL cells appears to disrupt the NB; in these cells, the NB antigens are detected in numerous smaller regions in the nucleus described as "microspeckles." Treatment of APL cells with retinoic acid (RA) results in differentiation of myeloid precursor cells and reformation of NBs [Dyck, J. A. et al., Cell 76:333-343 (1994); Weis, K. et al., Cell 76:345-356 (1994); Koken, M. H. M. et al., EMBO 13:1073-1083 (1994)]. In patients with APL, treatment with RA results in differentiation of leukemic cells and temporary disease remission [Warrell, R. P. et al., N. Eng. J. Med. 329:177-189 (1993)].

It is important to note however, that ANA are also found in a variety of other prevalent autoimmune disorders and a wide range of cancers [Bei, Masuelli, Palumbo, Modesti and Modesti (2008) Cancer Lett].

Indirect immunofluorescence (IIF) and solid-phase immunoassay are the two formats used to establish the presence or absence of autoantibodies in patients. Both methods have their pros and cons as discussed below:

For the past several decades, indirect immunofluorescence (IIF) has been the method of choice by physicians for the detection of autoantibodies present in the serum of autoimmune patients. Importantly, it remains the gold standard for AMA and ANA testing, including for PBC. Typically, patient serum is serial diluted in two-fold increments and allowed to bind to a cell substrate on a microscope slide (e.g. HEp-2 liver cells), which is then fluorescently stained to detect bound autoantibodies and examined under the microscope by a trained technician to identify the cellular/tissue staining patterns. IIF does have the advantage that as a cell/tissue based substrate, it can in theory "universally" cover all cellular autoantigens (pending their expression and preservation in the substrate). This, in part, is evidenced by the high diagnostic sensitivity of the IIF test, e.g. 93% (ANA) for systemic lupus erythematosus (SLE) [Solomon, Kavanaugh and Schur (2002) Arthritis Rheum 47: 434-44] and 90% (AMA) for PBC [Tanaka, Miyakawa, Luketic, Kaplan, Storch and Gershwin (2002) Cell Mol Biol (Noisy-le-grand) 48: 295-9].

Although IIF based AMA is a sensitive marker for PBC, the tradeoff may be specificity. Asymptomatic patients have been deemed AMA positive, and while a large portion only develop symptoms years later, some never develop symptoms at all [Metcalf, Mitchison et al. (1996) Lancet 348: 1399-402]. Moreover, one study found that 34% of AIH patients tested positive for AMA [Nezu, Tanaka, Yasui, Imamura, Nakajima, Ishida and Takahashi (2006) J Gastroenterol Hepatol 21: 1448-54].

Furthermore, the IIF assay is problematic overall when used as a routine diagnostic screening tool, as it is difficult to standardize owing to variations in the substrate and fixation process variations in the microscopy apparatus and due to the highly subjective interpretation of results [Jaskowski, Schroder, Martins, Mouritsen, Litwin and Hill (1996) Am J Clin Pathol 105: 468-73]. The consensus statement in 2004 from the Committee for Autoimmune Serology of the International Autoimmune Hepatitis Group (IAIHG) recommended that IIF be performed on three different organs from rodents [Vergani, Alvarez, Bianchi, Cancado, Mackay, Maims, Nishioka and Penner (2004) J Hepatol 41: 677-83]. Both AMA and anti-liver kidney microsomal-1 (LKM1) antibodies stain the renal tubules of the kidney, with differences only apparent to the trained eye, and this confusion can lead to a diagnosis of autoimmune hepatitis (AIR) instead of PBC [Bogdanos, Invernizzi, Mackay and Vergani (2008) World J Gastroenterol 14: 3374-87]. Moreover, some autoantigens are lost (unrecognizable) by diffusion or denaturation during the fixation process of IIF. Another confounding factor is that multiple autoimmune diseases can often occur together in the same patient, and the overlapping IIF patterns can lead to confusion in the correct diagnosis of each [Assassi, Fritzler et al. (2009) J Rheumatol; Norman, Bialek, Encabo, Butkiewicz, Wiechowska-Kozlowska, Brzosko, Shums and Milkiewicz (2009) Dig Liver Dis 41: 762-4]. Finally, IIF is slow, laborious and not amenable to high-throughput automation [Ulvestad, Kanestrom, Madland, Thomassen, Haga and Vollset (2000) Scand J Immunol 52: 309-15].

Although IIF remains the gold standard in AMA testing, solid-phase immunoassays, such as ELISA (Enzyme Linked Immunosorbent Assay), are gaining popularity, especially in high-throughput laboratories [Fritzler and Fritzler (2006) Curr Med Chem 13: 2503-12]. These methods have the advantage of high throughput automation, high analytical sensitivity, purely objective scoring, reliability, and the ability to test for specific autoantigen species, including in a multiplexed fashion [Fritzler and Fritzler (2006) Curr Med Chem 13: 2503-12]. With a resolution at the individual antigen level, these methods have the potential for greater disease specificity, if the correct marker panel is chosen. The drawback, however, is that a sufficient number of autoantigens needs to be both discovered and clinically validated to match the diagnostic sensitivity of the cellular substrate based IIF assay.

In one example of a commercial solid-phase immunoassay for PBC, INOVA Diagnostics Inc. (San Diego, Calif.) markets the MIT3 assay, an FDA-approved ELISA-based immunoassay for PBC based on the detection of AMAs. The MIT3 is utilizes a recombinant protein containing the immunodominant epitopes of all three E2 subunits of the pyruvate dehydrogenase complex [Moteki, Leung, Coppel, Dickson, Kaplan, Munoz and Gershwin (1996) Hepatology 24: 97-103]. The overall goal of these tests is to mimic the cellular IIF-based AMA test for PBC, but with all the aforementioned benefits of solid-phase immunoassays of individual antigens. Still, this test is only meant to be diagnostic aid, together with clinicopathological findings for PBC. In one study, the AMA-based MIT3 ELISA assay had a reported a diagnostic sensitivity of 81.6%, however, it is important to note that serum samples with AMA-negative PBC disease were excluded [Gabeta, Norman, Liaskos, Papamichalis, Zografos, Garagounis, Rigopoulou and Dalekos (2007) J Clin Immunol 27: 378-87]. In another study, it was shown that the MIT3 assay, for instance, lacks all the necessary mitochondrial autoantigens for maximum diagnostic sensitivity of PBC [Dahnrich, Pares et al. (2009) Clin Chem 55: 978-85].

This highlights the need for the discovery and validation of additional autoantigen biomarkers to be used in solid-phase immunoassays for the optimal diagnosis of autoimmune diseases such as PBC. The most effective methods for the discovery of autoantigens are proteomics based. Proteomics can be defined as the global (e.g. parallel or simultaneous) analysis of the entire expressed protein compliment of the genome [Wasinger, Cordwell et al. (1995) Electrophoresis 16: 1090-4]. Proteomics methods allow for the discovery of novel autoantigens in an unbiased fashion. Common proteomics methods for discovery of novel autoantigens include SEREX (serological identification of antigens by recombinant expression cloning) [Krebs, Kurrer, Sahin, Tureci and Ludewig (2003) Autoimmun Rev 2: 339-45] and human proteome microarrays ("chips", commonly the dimensions of standard microscope slides, containing thousands of purified recombinant human proteins printed to their surface in an ordered array of microscopic spots, e.g. spots of 100 micron in diameter) [Robinson, DiGennaro et al. (2002) Nat Med 8: 295-301; Robinson, Steinman and Utz (2002) Arthritis Rheum 46: 885-93].

SUMMARY OF THE INVENTION

The present invention relates to methods of using the novel autoantigens (Tables I and V) human hexokinase 1 (HK1) and/or kelch-like 12 (KLHL12), or fragments thereof comprising an epitope, in the diagnostic, prognostic, staging and therapeutic regimens of the autoimmune liver disease Primary Biliary Cirrhosis (PBC). The present invention also relates to methods of using homologs, family members, transcript variants and isoforms (e.g. Table VI), preferably at least 70% identical, more preferably at least 90% identical and most preferably at least 95% identical, of human hexokinase 1 (HK1) and/or kelch-like 12 (KLHL12), or fragments thereof comprising an epitope, in the diagnostic, prognostic, staging and therapeutic regimens of the autoimmune liver disease Primary Biliary Cirrhosis (PBC).

The present invention further provides isolated antibodies that bind specifically to the above-described polypeptides, or fragments thereof comprising an epitope. Antibodies provided herein may be polyclonal or monoclonal, may be affinity purified, may be immobilized onto a solid support, and may be detectably labeled. The invention also provides methods for detecting the presence of an autoimmune disease in an animal, preferably a human, comprising the steps of isolating a body fluid sample, preferably blood, serum or plasma, from the animal, incubating the serum with an isolated HK1 and/or KLHL12 polypeptide described above, and detecting the binding of autoantibodies in the serum sample to the isolated polypeptide. The invention also provides alternative methods for detecting the presence of an autoimmune disease in an animal comprising the steps of isolating a body fluid sample from the animal, preferably blood, serum or plasma, and immobilizing components of the serum on a solid support, contacting the immobilized serum components with an isolated polypeptide described above under conditions favoring the formation of a complex between the serum components and isolated polypeptide, contacting the formed complex with an antibody that binds specifically to HK1 and/or KLHL12, and detecting the binding of the antibody to the complex. Autoimmune diseases that may be diagnosed by the methods of the present invention include primary biliary cirrhosis (PBC) and systemic lupus erythematosis (SLE). Cancers that may be diagnosed by the methods of the present invention include colorectal cancer (CRC). The present invention also provides methods of determining prognosis, disease stage and treatment regimens using the aforementioned methods of detecting autoantibodies against HK1 and/or KLHL12.

In a preferred embodiment, heterogeneous or homogenous immunoassays, single-plex or multiplex, are used to detect autoantibodies present in body fluids directed against said autoantigens. Other preferred embodiments of the present invention will be apparent to one of ordinary skill in light of the following drawings (Figures) and description of the invention, and of the claims.

EXPERIMENTAL

Example 1

Proteome Microarray Based Discovery of Novel Primary Biliary Cirrhosis (PBC) Autoantigens Serum Screening on Microarrays Patient sera were screened against commercial human proteome microarrays comprised of about 8,000 unique human recombinant (eukaryotically expressed) proteins printed in duplicate at high density to a "chip" the size of a standard microscope slide (Human ProtoArray® protein microarray v4.0, Invitrogen, Carlsbad, Calif.) [Sheridan (2005) Nat Biotechnol 23: 3-4 ]Microarrays were performed according to the manufacturer's instructions. Microarrays were imaged on an ArrayWoRx®$^e$ BioChip fluorescence reader (Applied Precision, LLC, Issaquah, Wash.) using the appropriate standard built-in filter sets. Image analysis and data acquisition was performed using the GenePix® Pro v6.1 software package (Molecular Devices, Sunnyvale, Calif) according to the instructions of the microarray manufacturer (Human ProtoArray® v4.0, Invitrogen, Carlsbad, Calif.).

92 different serum samples from normal individuals and patients with various diseases were individually screened against the proteome microarrays in order to detect the presence of autoantibodies against the arrayed proteins (potential autoantigens). For this, 2 different lots of microarrays were used in 2 sequential studies. The composition of the entire patient population was as follows: Microarray Lot #1 (80 unique samples)-18 Primary Biliary Cirrhosis (PBC) patients versus 62 non-PBC control samples [13 normal, 25 colorectal cancer (CRC), 22 systemic lupus erythematosus (SLE), 2 Sjögrens syndrome (SjS)]. Microarray Lot #2 (12 unique samples)-3 more PBC and 9 more non-PBC controls [4 normal and 5 autoimmune hepatitis (AIH)]. The normal sera were approximately age and gender matched to the PBC cohort. The AIH sera were used because it is an autoimmune liver disease different from PBC yet known to be associated with autoantibodies. The CRC sera were used because cancer patients are also known to have various autoantibodies against so-called tumor associated autoantigens (TAA), including a common repertoire of nuclear autoantibodies observed in both cancers and autoimmune disease [Bei, Masuelli, Palumbo, Modesti and Modesti (2008) Cancer Lett]. Archived sera were obtained from the repositories of the following sources: Our collaborator, Dr. Donald Bloch, M.D., Center for Immunology and Inflammatory Diseases, Massachusetts General Hospital, Assistant Professor of Medicine, Harvard Medical School provided 12 of the SLE sera as well as the SjS and PBC sera. Remaining SLE sera and all the AIH sera were from Bioreclamation Inc. (Hicksville, N.Y.), normal sera were from ProMedDx, LLC (Norton, Mass.) and CRC sera were from Asterand Inc. (Detroit, Mich.).

Biostatistical Analysis of Microarray Data

In order to identify the autoantigen biomarkers from the microarray data, the biostatistical methods used were the standard approaches provided by the microarray manufacturer in the form of the ProtoArray® Prospector v4.0 software package (Invitrogen, Carlsbad, Calif.) using the Immune Response Profiling (IRP) add-on [Hudson, Pozdnyakova, Haines, Mor and Snyder (2007) Proc Natl Acad Sci USA 104: 17494-9]. Two of the biostatistical methods from this software package were used to create two corresponding PBC autoantigen lists as follows:

"Hit Calling" Autoantigen List: To convert the data to binary format, proteins (i.e. potential autoantigens) on each microarray (1 serum/microarray) were scored as a "hit" (i.e. positive) or not a hit (i.e. negative). Autoantigen hits were called on a per microarray basis using the Z-score with a cutoff threshold of 3 standard deviations above the microarray mean. The number of hits in the PBC and control groups for each autoantigen were used to determine the percent prevalence of each autoantigen. Autoantigens ultimately placed on this list had to have greater percent prevalence in the PBC cohort than the control cohort (i.e. all non-PBC samples).

M-Statistics Autoantigen List: This approach uses quantile normalized microarray data and performs a pairwise t-test for each protein between the two patient groups (i.e. PBC group and the control group corresponding to all non-PBC patients). This algorithm also estimates the autoantigen prevalence based on cutoffs set by the quantile normalized data, Autoantigens ultimately placed on this list had to have greater percent prevalence in the PBC cohort than the control cohort (i.e. all non-PBC samples) and had to have M-Statistics p-values of <0.1.

Microarray Lots #1 and 2 were analyzed separately. To comprise a single final list of microarray-derived PBC autoantigens, those observed as overlapping on both aforementioned biostatistical lists for Microarray Lot #1 (only)

were taken. Next, any markers on this compiled list that were positive in any of the AIH patients (Microarray Lot #2), as determined by the "Hit Calling" method, were eliminated. Finally, the list was then prioritized based on the M-Statistics p-value as well as diagnostic sensitivity and specificity.

Results:

Two of the PBC autoantigen markers, human Hexokinase 1 (HK1) and human Kelch-Like 12 (KLHL12), identified from the proteome microarrays and claimed in this patent, are listed in Table I, along with their M-Statistics p-values as well as their diagnostic sensitivities and specificities (calculated from Microarray Lot #1). Quantile normalized microarray data (normalized autoantibody signal intensity) for all 92 samples (i.e. all 92 microarrays) are shown in FIG. 16 and FIG. 17 for HK1 and KLHL12 respectively. In summary (Table I), the presence of serum autoantibodies against either autoantigen is strongly correlated with the PBC cohort, showing highly significant p-values ($1\times10^{-10}$ and $8\times10^{-5}$ for HK1 and KLHL12 respectively) as well as sensitivities of 85-89% and 33-40% for HK1 and KLHL12 respectively, and, specificities 84-90% and 97-98% for HK1 and KLHL12 respectively (see Table I for details). By definition (see "Biostatistical Analysis of Microarray Data" above in this Example), none of the 5 Autoimmune Hepatitis (AIH) sera were positive for HK1 or KLHL12 (see also FIG. 16 and FIG. 17; Microarray Lot #2). The HK1 and KLHL12 autoantigen biomarkers were also the subject of further validation as detailed in other experimental Examples.

It should also be noted that HK1 autoantibodies are also observed with low prevalence in systemic lupus erythematosis (SLE) and colorectal cancer (CRC) (FIG. 16). N-03 is the only "normal" serum sample to be positive for HK1 (FIG. 16; red bar). N-03 is also the only "normal" serum sample to be positive for KLHL12 (FIG. 17; red bar). Thus, in fact, it is believed that N-03 may in fact have yet undiagnosed or unreported/undocumented PBC (note that autoantibodies have been shown to pre-date clinical symptoms/manifestations of autoimmune disease, including in PBC).

Example 2

Pre-Validation of Novel Primary Biliary Cirrhosis (PBC) Autoantigens HK1 and KLHL12 Using an ELISA It should be noted that the ELISA assay described here in this Example and used in many subsequent Examples is termed $T^2$-ELISA, and is based on the use of dual-epitope tagged cell-free expressed protein antigens. In this Example, those antigens are HK1 and KLHL12 and the $T^2$-ELISA used as a tool for clinical pre-validation (and eventually validation in later Examples) of these microarray-derived novel autoantigens.

Autoantigen Expression

The entire Open Reading Frames (ORFs) of human HK1 and KLHL12 were cloned, using standard and accepted molecular biology practices, into a plasmid vector compatible with cell-free protein expression, containing the T7 RNA polymerase promoter, a Kozak (ribosome binding) sequence, a start codon, an N-terminal VSV-G epitope tag (YTDIEMNRLGK (SEQ ID NO: 19)), and a C-terminal HSV epitope tag (QPELAPEDPED (SEQ ID NO: 20)) in addition to the ORF insert. As source DNA for cloning into the expression vector, full-length sequence-verified clones were purchased from OpenBiosystems (Huntsville, Ala.) [catalog OHS1770-9381021 (UniGene Hs.370365) for HK1 and MHS1011-61211(UniGene Hs.706793) for KLHL12]. Expression vectors were verified for the correct ORF insert using standard EcoRI digestion methods and/or DNA sequencing.

Autoantigens were produced from the aforementioned plasmid clones by cell-free protein expression. Cell-free protein expression reactions were performed using a transcription/translation coupled rabbit reticulocyte lysate system (TNT® T7 Quick for PCR DNA system; Promega, Madison, Wis.) according to the manufacturer's instructions. Autoantigen expression reactions contained the cognate plasmid DNA while blank expression reactions lacked only the plasmid DNA. Expression reactions were stopped by diluting 1/20 in TDB [1% BSA (w/v) and 0.1% (v/v) Triton X-100 in TBS-T (50 mM Tris, pH 7.5, 200 mM NaCl, 0.05% (v/v) Tween-20)].

Dual-Tag Enzyme-Linked Immunosorbent Assay ($T^2$-ELISA) of Autoantigens

Nunc-Immuno™ Microwell™ Polysorp® 96 well polystyrene microtiter plates, (untreated, white opaque, flat bottom), (Nunc Brand from Thermo-Fisher Scientific, Rochester, N.Y.) were used for a sandwich type Enzyme-Linked Immunosorbent Assay (ELISA). Plates were coated with 0.5μg/mL of a mouse monoclonal anti-HSV Tag® capture antibody (EMD Biosciences, Inc., San Diego, Calif.) in sodium carbonate/bicarbonate pH 9.3 for 30 min with shaking (50μL/well). Plates were then washed 6× in TBS-T (wells filled to maximum) on an ELx405 Select Robotic Plate Washer (BioTek, Winooski, Vt.). All plate washes were performed in this manner unless noted otherwise. Plates were then blocked for 30 min at 300 μL/well in 1% BSA (w/v) in TBS-T. The solution was removed from the plates and the aforementioned stopped (i.e. diluted) cell-free expression reactions (autoantigen and blank reactions) were then added at 100 μL/well and shaken for 30 min. Plates were washed and serum samples (diluted at 1/1,000 in 1% BSA (w/v) in TBS-T) were added at 100 μL/well and shaken for 30 min. Each serum sample was run against triplicate wells of autoantigen and triplicate wells of the cell-free expression blank. Additionally, one set of triplicate wells of autoantigen and one set of triplicate wells of the cell-free expression blank were designated for VSV-G epitope tag detection, and therefore received plain 1% BSA (w/v) in TBS-T instead of diluted serum. To avoid contamination of the robotic plate washer with human serum, plates were subsequently washed 4× by manual addition of TBS-T (wells filled to maximum) followed by vacuum aspiration and then washed 6× in the robotic plate washer as described earlier in this Example. Wells designated for detection of the VSV-G epitope tag then received an anti-VSV-G horseradish peroxidase (HRP) labeled monoclonal antibody (Clone P5 D4, Roche Applied Science, Indianapolis, Ind.) diluted 1/20,000 in 1% BSA/ TBS-T. Wells designated for detection of serum autoantibody received a mouse anti-[human IgG] HRP labeled monoclonal secondary antibody (minimum cross-reactivity with mouse immunoglobulin; Jackson ImmunoResearch Laboratories, Inc, West Grove, Pa.) diluted 1/20,000 in 1% BSA/TBS-T. Plates were shaken for 30 min. The solutions were then manually dumped from the plates by inversion followed by vigorous patting of the plates inverted on a dry paper towel to remove residual fluid. Plates were then washed in the robotic plate washer as described earlier in this Example. Chemiluminescence signal was generated by the addition of 50 μL/well of SuperSignal ELISA Pico Chemiluminesence Substrate (Pierce Brand from Thermo Fisher Scientific, Rockford, Ill.). Plates were developed by shaking for 15 min and then read on a LumiCount luminescence plate reader (1 s exposure, PMT of 650V, gain 1) (Packard/PerkinElmer Life and Analytical Sciences, Inc., Boston, Mass.).

Results:

For this pre-validation of the new PBC autoantigen markers listed in Table I, randomly selected sera that were detected as positive or negative for a given autoantigen in the microarray analyses (see Example 1) were also analyzed here by T²-ELISA.

Calculation of Autoantibody Units from the T²-ELISA, in short, was achieved by background subtracting the data and normalizing to the detection of the common VSV-G epitope tag for each antigen on each assay (i.e. each plate). More specifically, for each serum-autoantigen pair, for each of the triplicate wells from the T²-ELISA data, Autoantibody Units were calculated as follows: [autoantibody signal from one well (i.e. serum versus autoantigen)] minus (average background from triplicates (i.e. same serum versus average of all three blank expression wells)] to yield triplicate Background Subtracted Values (BSV) for each serum-autoantigen pair. Note that one assay is defined as one 96-well microtiter ELISA plate. To normalize for inter-assay variances (day-to-day and assay-to-assay) for each autoantigen, wells on each assay, for each autoantigen on that assay, were dedicated solely for detection of the common VSV-G epitope tag. The VSV-G Normalization Factor (VNF) was calculated as follows: [average VSV-G signal for triplicate wells (i.e. autoantigen wells probed with VSV-G antibody)] minus [average VSV-G background for triplicate wells (i.e. blank expression wells probed with VSV-G antibody]. On a per assay basis, the triplicate BSV for all serum-autoantigen pairs were then divided by the VNF for that assay and multiplied by 100, yielding triplicate Autoantibody Unit values for each serum-autoantigen pair (i.e. expressed as a percent of the VNF). Note that a floor of zero was set for the Autoantibody Units. The average and standard deviation (errors bars) were calculated and plotted in FIGS. 1 and 2 for the new PBC autoantigens HK1 and KLHL12 respectively.

Sera were scored "analytically", as positive or negative in the T²-ELISA in order to check concordance with the microarrays. For this, both of the following criteria must have been met for each serum-autoantigen pair to have been scored as analytically positive in the T²-ELISA: i) a p-value ≤0.05 in a 1-tailed homoscedastic unpaired t-test on the raw T²-ELISA values from the triplicate wells of the autoantibody signal (i.e. serum versus autoantigen) compared to background (i.e. same serum versus blank expression wells); ii) autoantibody signal-to-background ratio ≥2. In FIGS. 1 and 2, T²-ELISA scores and microarray ("Array") scores are denoted as positive (+) or negative (−). For HK1 (FIG. 1), of 12 randomly selected sera that were positive by the microarray analyses, 10 were positive by ELISA for 83% concordance. Additionally for HK1 (FIG. 1), 5 sera were randomly selected that were negative on the microarrays, all of which were also negative by T²-ELISA for a 100% concordance. For KLHL12, of the 7 negative and 4 positive sera randomly chosen from the microarray analyses (see Example 1), there was full 100% concordance with the T²-ELISA results as shown in FIG. 2.

Example 3

Validation of Novel Primary Biliary Cirrhosis (PBC) Autoantigens HK1 and KLHL12 Using an ELISA on a New AMA-Positive PBC Patient Cohort not Previously Screened by Microarrays Autoantigen Expression
As in Example 2.
Dual-Tag Enzyme-Linked Immunosorbent Assay (T²-ELISA) of Autoantigens
As in Example 2.
Results:
A critical validation of the newly discovered markers is to perform studies on a new patient cohort (22 PBC samples), never before screened on the proteome microarrays. In this Example, this has been done with both of the new PBC autoantigens, HK1 and KLHL12 (previously listed in Table I).

The new PBC sera were obtained from our collaborator, Dr. Donald Bloch, M.D., Center for Immunology and Inflammatory Diseases, Massachusetts General Hospital, Assistant Professor of Medicine, Harvard Medical School and the normal sera were from ProMedDx, LLC (Norton, Mass.).

Calculation of Autoantibody Units from the T²-ELISA, in short, was achieved by background subtracting the data and normalizing to the positive control on each assay (i.e. each plate), whereby the positive control is set to 1,000 Autoantibody Units. More specifically, for each serum-autoantigen pair, for each of the triplicate wells from the T²-ELISA data, Autoantibody Units were calculated as follows: [autoantibody signal from one well (i.e. serum versus autoantigen)] minus [average background from triplicates (i.e. same serum versus average of all three blank expression wells)]. This yields triplicate Background Subtracted Values (BSV) for each serum-autoantigen pair. Note that one assay is defined as one 96-well microtiter ELISA plate. To normalize for inter-assay variances (day-to-day and assay-to-assay) for each autoantigen, a common positive control PBC serum for HK1 and KLHL12 was run on every assay (selected from the microarray PBC cohort in Example 1). The positive control T²-ELISA data were processed in the aforementioned manner on a per assay basis and the triplicate BSV averaged to yield the Positive Control Normalization Factor (PCNF) for each assay. On a per assay basis, the triplicate BSV for all serum-autoantigen pairs were then divided by the PCNF for that assay and multiplied by 1,000, yielding triplicate Autoantibody Unit values for each serum-autoantigen pair. Importantly, the VSV-G common epitope tag detection (Example 2) was still used to verify successful and consistent autoantigen expression, but was not used here in the calculation of Autoantibody Units.

In order to set diagnostic scoring thresholds for a given auto antigen, the T²-ELISA assay was run on a group of 22 normal patient sera and the cutoffs then set at 2 standard deviations above the mean for this normal cohort, for ~95% statistical confidence. The use of this method at 2-3 standard deviations is common practice (e.g. [Liu, Wang, Li, Xu, Dai, Wang and Zhang (2009) Scand J Immunol 69: 57-63]). However, a critical requirement of this standard deviation based cutoff calculation method is that the data follows a Gaussian distribution, yet a Shapiro-Wilk test for normality determined this was not the case. As a solution, we $\log_2$ transformed the Autoantibody Units and set the floor to 0 (i.e. non-transformed values of ≤0 were left as 0 without transformation) yielding a Gaussian distribution (of the >0 values) and allowing cutoffs to be set based on the aforementioned standard deviation methodology. Autoantibody Unit values of ≤0 were excluded from the cutoff calculations because background subtraction is used in the calculation of Autoantibody Units, meaning patient samples yielding ≤0 values would by definition have to be scored as autoantibody negative regardless (i.e. a cutoff is not needed nor relevant to ≤0 values).

As seen by the data in FIG. 3 for HK1, using a cutoff of 2.0, an 82% diagnostic sensitivity (100% specificity) on this new sample cohort is in good agreement with the microarray analyses performed on the original sample cohort (see Table I). As seen by the data in FIG. 4 for KLHL12, using a cutoff of 2.5, a 36% diagnostic sensitivity (100% specificity) on this new sample cohort is in good agreement with the microarray analyses performed on the original sample cohort (see Table I).

Example 4

Validation of Novel Primary Biliary Cirrhosis (PBC) Autoantigens HK1 and KLHL12 Using an ELISA on a New Anti-Mitochondrial Antibody (AMA)-Negative PBC Patient Cohort not Previously Screened by Microarrays

Patients with suspected PBC but an antimitochondrial antibody (AMA)-negative status make up approximately 5-20% of all PBC patients [Oertelt, Rieger et al. Hepatology 2007; 45:659-665], and AMA-negative PBC patients are particularly difficult to confirm diagnostically based on serotesting. Employing the known and validated autoantigens Sp100 and gp210 only results in the detection of a fraction of the AMA-negative PBC patients (e.g. 17-33% in one recent study [Liu, Shi, Zhang, Zhang and Gao (2008) Liver Int 28: 233-9]), showing a need for specific autoantigens which can detect AMA-negative PBC patients.

To test the ability of our novel autoantigens, HK1 and KLHL12, to detect AMA-negative PBC patients, we utilized 17 patient sera which were AMA-negative by indirect immunofluorescence (IIF) but with confirmed PBC by conventional methods [Heathcote (2000) Hepatology 31: 1005-13], and by liver biopsy. The new AMA-negative PBC sera were obtained from our collaborator, Dr. Donald Bloch, M.D., Center for Immunology and Inflammatory Diseases, Massachusetts General Hospital, Assistant Professor of Medicine, Harvard Medical School. We compared the ability of our novel autoantigens, HK1 and KLHL12, with the available commercial tests to detect these patients with confirmed PBC but a known AMA-negative status.

Autoantigen Expression
As in Example 2.

Dual-Tag Enzyme-Linked Immunosorbent Assay ($T^2$-ELISA) of Autoantigens
As in Example 2.

FDA-Approved Commercial PBC ELISAs
FDA-approved commercial ELISAs for PBC diagnostics were also run and were the QUANTALite® ELISA assay for M2 EP (MIT3), QUANTALite® ELISA assay for sp100, QUANTALite® ELISA assay for gp210 and QUANTALite® ELISA assay for PBC Screen IgG/IgA from INOVA Diagnostics (San Diego, Calif.); and were performed according to the manufacturer's instructions.

Results:
For scoring purposes, Autoantibody Unit calculations and diagnostic thresholds established in Example 3 were once again employed here for each autoantigen (HK1 and KLHL12).

As illustrated by the data in FIG. 5 for HK1, 4 out of 17 AMA-negative PBC sera tested positive for this autoantigen (24% sensitivity). As seen by the data in FIG. 6 for KLHL12, 6 of the 17 AMA-negative PBC sera tested diagnostically positive (35% sensitivity).

We also tested the aforementioned 17 AMA negative PBC sera on all four of INOVA Diagnostics' commercially available FDA-approved PBC tests, namely, QUANTALite® ELISA assay for M2 EP (MIT3), QUANTALite® ELISA assay for sp100, QUANTALite® ELISA assay for gp210 and QUANTALite® ELISA assay for PBC Screen IgG/IgA. The results of these tests, as well as our $T^2$-ELISA results with HK1 and KLHL12, are summarized in Table II. INOVA's tests were unable to detect 3 of the 17 patients (18%). Strikingly however, HK1 and KLHL12 were each able to detect one of the previously undetectable AMA-negative PBC sera (PB-AMN-044 and PB-AMN-263 respectively). The third patient (PB-AMN-084) remained undetected by the aforementioned autoantigens but was detected by Sp140(see Example 6 for details). These results are summarized in FIG. 7 as a Venn Diagram, illustrating overlap (or lack thereof) between the various biomarkers. Note that the results of the QUANTALite® ELISA assay for PBC Screen IgG/IgA ELISA are not shown in the Venn Diagram (FIG. 7), however, as seen in Table II, this assay did not increase detection as compared to the other INOVA assays. Together, these findings indicate that our two novel autoantigens, HK1 and KLHL12, are diagnostically very significant. It suggests that adding our novel biomarkers to the existing panel of PBC biomarkers could result in the improved detection, and therefore earlier treatment and improved outcome of PBC patients, in particular for AMA-negative PBC patients.

Example 5

Assessing HK1 and KLHL12 in Patients with Atypical Indirect Immunofluorescent (IIF) Staining

We propose that the number of PBC patients may be higher than previously suspected, due to the extreme difficulty in drawing a conclusive diagnosis of PBC in the absence of definitive AMA staining or the proper anti-nuclear autoantibody (ANA) staining pattern as determined by indirect immunofluorescence (IIF). To test this theory, we examined sera from undiagnosed patients with diffuse cytoplasmic or nuclear membrane IIF staining patterns. These new patient sera were obtained from our collaborator, Dr. Donald Bloch, M.D., Center for Immunology and Inflammatory Diseases, Massachusetts General Hospital, Assistant Professor of Medicine, Harvard Medical School.

Autoantigen Expression
As in Example 2.

Dual-Tag Enzyme-Linked Immunosorbent Assay ($T^2$-ELISA) of Autoantigens
As in Example 2.

QUANTALite® ELISA Assay for M2 EP (MIT3)
Assay was performed according to manufacturer's instructions (INOVA Diagnostics, San Diego, Calif.).

Results:
We ran HK1, KLHL12 and the M2 EP (MIT3) QUANTALite® Assay (INOVA Diagnostics, San Diego, Calif.) on 20 patients, the results of which are shown in FIG. 8. Serum samples prefixed with "Cyto" or "NM" are from patients with diffuse cytoplasmic or nuclear membrane IIF staining, respectively. Calculation of Autoantibody Units for the $T^2$-ELISA as run on HK1 and KLHL12 was done as in Example 2. Scoring for the $T^2$-ELISA assay was done according to the "analytical" method described in Example 2(note that any serum sample with a graphed bar in FIG. 8 is positive). To avoid scale effects, graphed data for each antigen in FIG. 8 is normalized as a percent of the patient having the maximum autoantibody units for that antigen (that patient is marked with a blue arrow for each antigen). We set the Y-axis to INOVA's MIT3 cut-off of 25 units (based on the low positive control; cutoff determined per manufacturer's instructions), which corresponded to 17%, so all bars shown represent positive results.

One patient is detected by all three markers. Novel autoantigen KLHL12 detects two nuclear membrane patients that no other markers detect. Finally, MIT3 detects one nuclear membrane and several cytoplasmic patients that no other marker detects. These results strongly suggest that detection of the HK1, KLHL12 and MIT3 antigens may be useful in revealing

Example 6

Improved Diagnostic Sensitivity by ELISA for Primary Biliary Cirrhosis (PBC) by Detection of Sp140

Antinuclear antibodies reacting with 5-20 nuclear dots are detected in 20-30% of patients with primary biliary cirrhosis (PBC). The "multiple nuclear dot" (MND) staining pattern produce by these antibodies is directed against promyelocytic leukemia protein nuclear body (PML NB) components, one of which was recently identified as Sp140. Sp140 has been reported to be present in 13% of PBC patients, with a larger proportion of AMA-negative compared with AMA positive PBC patients (53% versus 8%) [Granito, A, Yang, W. et. al, 2009, Am J Gastroenterol, In Press]. We therefore tested Sp140 in our $T^2$-ELISA.

The PBC patient sera were obtained from our collaborator, Dr. Donald Bloch, M.D., Center for Immunology and Inflammatory Diseases, Massachusetts General Hospital, Assistant Professor of Medicine, Harvard Medical School. Sp140 status was initially determined by IIF on Sp140 expressing cells versus negative cells.

Autoantigen Expression

As in Example 2.

Dual-Tag Enzyme-Linked Immunosorbent Assay ($T^2$-ELISA) of Autoantigens

As in Example 2.

QUANTALite® ELISA Assay for Sp100

Assay was performed according to manufacturer's instructions (INOVA Diagnostics, San Diego, Calif.).

Results:

$T^2$-ELISA Autoantibody Unit calculations and "analytical" scoring were performed as in Example 2. Scoring for the INOVA Diagnostics Sp100 ELISA were performed according to the manufacturer's instructions. Results are in Table III. Notably, although Sp100 was unable to be detected in PBC patients PB-AMP-020 or PB-AMN-084 (orange shading) by either our $T^2$-ELISA or INOVA's assay, the $T^2$-ELISA platform was able to detect these PBC patients using the Sp140 autoantigen. The detection of PB-AMN-084 is most notable, since this patient was not detected by any of the following: the Sp 140 indirect immunofluorescence (IIF) methods (not shown), any of INOVA's available PBC ELISA tests, or either of the novel autoantigens HK1 and KLHL12 as determined by $T^2$-ELISA (see earlier in Example 4 and Table II for these ELISA results).

Together then, HK1, KLHL12 and Sp140 may serve as a powerful diagnostic panel of autoantigens which enable the rapid and accurate diagnosis of previously missed PBC patients.

This Example also demonstrates another important result, that is, with respect to Sp100, our $T^2$-ELISA platform is essentially 100% concordant with INOVA's FDA-approved Sp100 ELISA. The only discordant results were 2 cases where the $T^2$-ELISA gave a negative result and the INOVA assay an equivocal result, that is, too close to INOVA's designated cutoff to be conclusive (per the manufacturer's scoring methods).

Example 7

Calorimetric Versus Chemiluminescent ELISA Detection of Autoantibodies Against the Novel Primary Biliary Cirrhosis (PBC) Autoantigens HK1 and KLHL12 Using PBC Patient Serum ELISA experiments exploring the binding between autoantigens and autoantibodies usually employ one of two detection strategies. Chemiluminescence is generally accepted to be more sensitive and has a broader dynamic range, while colorimetric is generally accepted to be more stable and consistent. The purpose of these experiments was to perform the exact same experiment twice and then to develop it in parallel, once by colorimetric detection, and once by chemiluminescent detection.

Autoantigen Expression and $T^2$-ELISA

Performed as in Example 2 except that for the calorimetric ELISA detection, the following reagents from the INOVA Diagnostics QUANTALite® ELISA platform (San Diego, Calif.) were utilized: HRP Sample Diluent, HRP Wash Concentrate, HRP IgG Conjugate, TMS Chromogen, HRP Stop Solution. Instructions were followed per the manufacturer. The diagnostic scoring for the chemiluminescent ELISA were those as already determined in Example 4 for the same sera.

Results:

ELISA results of HK1 on sera from PBC patients are shown in FIG. 9A and KLHL12 in FIG. 9B, demonstrating both colorimetric and chemiluminescent detection. Colorimetric assay results are plotted as signal minus background, with the background being the same serum run against an expression blank (no autoantigen expressed). The chemiluminescence ELISA score is listed under the X-Axis as "+" (positive) or "−" (negative). Note that the scores for the chemiluminescent ELISA were those as already determined in Example 4 for the same sera (with sera PB-AMN-044 and PB-AMN-263, green outline in FIGS. 9A and B, being the ones that scored previously negative for all available PBC ELISA assays from INOVA Diagnostics but positive for HK1 and KLHL12 respectively). These results clearly demonstrate concordance between the chemiluminescent and colorimetric ELISA readout methods.

Example 8

Feasibility of Point-of-Care Diagnostics—Colorimetric Dot Blot Detection of Autoantibodies Against the Novel Primary Biliary Cirrhosis (PBC) Autoantigen HK1 Using PBC Patient Serum The purpose of this example is to show proof-of-principle for use of autoantigens in a point-of-care (POC) autoantibody based diagnostic assay for autoimmune disease (i.e. an assay that is rapidly and readily performed in the doctor's office, e.g. by an internist, general practitioner or rheumatologist).

One common format of a solid-phase immunoassay for point-of-care (POC) diagnostics is the lateral flow based immuno-chromatographic method, performed on a porous solid membrane matrix, such as nitrocellulose. For example, a blood sample as well as a colorimetrically labeled detector reagent (commonly a colloidal gold label) are allowed to flow by capillary action across the length of a nitrocellulose strip, subsequently contacting the test area where, for example, an antigen, capture antibody or other capture agent had been previously immobilized (i.e. striped). A positive result is visualized as a colored stripe in the test area.

The most ubiquitously recognized form of such an assay is the "home" pregnancy test, however, various formats for rapidly detecting antibodies in human blood, e.g. for detection of pathogen infection, are possible [Biagini, Sammons, Smith, MacKenzie, Striley, Snawder, Robertson and Quinn (2006) Clin Vaccine Immunol 13: 541-6; Laderman, Whitworth, Dumaual, Jones, Hudak, Hogrefe, Carney and Groen (2008) Clin Vaccine Immunol 15: 159-63].

To mimic this type of device and show feasibility with the new PBC autoantigen HK1 reported in this patent, a dot blot assay was performed. In this assay, autoantigen is immobilized on a nitrocellulose membrane which is then probed with patient serum. Detection of bound autoantibody is achieved with a colloidal-gold labeled anti-human IgG detector antibody. Details of the procedure and results are as follows:

Colorimetric Dot Blot of Autoantigen

Recombinant purified human Hexokinase 1 protein (HK-1, Alpha Diagnostic, International, San Antonio, Tex.) was diluted to 200 ng/µL in TBS (50 mM Tris, pH 7.5, 200 mM NaCl). Human IgG was diluted to 250 ng/µL in PBS (50 mM sodium phosphate, pH 7.5, 100 mM NaCl).

Nitrocellulose (HiFlow Plus, Millipore Corporation, Bedford, Mass.) was cut to form 0.5 cm×3 cm strips. 1 µl each of TBS, HK1 and human IgG were individually spotted onto the nitrocellulose and allowed to dry thoroughly by incubation for 1 h at 37° C. Strips were then treated in Block buffer [1% BSA (w/v) in TBS-T (TBS with 0.05% v/v Tween-20)] for 30 min at room temperature (RT). Block was vacuum aspirated. Patient serum was diluted 1:100 in Block and then incubated with nitrocellulose strips for 30 min at RT. Serum was aspirated and the strips were washed with 1.5 mL TBS-T: 4×5 min each. Strips were probed with colloidal gold conjugated secondary antibody [Anti-Human IgG (H+L) antibody, Gold labeled (40 nm), KPL, Gaithersburg, Md.] diluted 1:10 in Block shaking at RT for 3 hours.

Results:

Lateral flow immunoassays offer a simple, accurate, fast result-reporting and ease-of-use format and thus are a popular point-of-care (POC) diagnostic platform. Lateral flow-based devices use immunochromatographic principles to assay biofluids such as blood for various analytes in a matter of minutes, under "field" conditions with no special instrumentation or expertise. To test the feasibility of a colorimetric lateral flow POC assay of PBC autoantigens, we performed a model dot blot experiment.

Recombinant purified human HK1 was spotted onto nitrocellulose, as well as carrier buffer (negative control) and human IgG (positive control). Diluted sera (1:100) from a PBC patient and normal patient was allowed to bind and washed before adding colloidal gold labeled anti-human IgG. Results are shown in FIG. 10. After 1 h 20 min, all IgG spots (positive controls) had turned pink. The HK1 spot turned pink with 1:100 dilution of PBC patient serum but was negative (no color) with normal serum. Negative control spots (carrier buffer only) remained colorless.

Example 9

A Dual-Epitope Tag Based Solid-Phase Heterogeneous Assay ($T^2$-ELISA) as a Tool for Detecting Protein Interactions We have developed a novel, high throughput and internally normalized solid-phase heterogeneous assay which is based on dual-epitope tagged cell-free (in vitro) expressed target proteins captured on a surface. The assay can detect the binding of "probes" (e.g. drugs, oligonucleotides or antibodies) to the surface-immobilized cell-free expressed target proteins while being able to normalize for the amount of target protein on the same surface. Although the Example shown here relates to detection of autoantibody binding from human serum to cell-free expressed autoantigens as the target proteins, the methodology is broadly applicable. Furthermore, although the assay format used in this Example is a microwell (microtiter) plate based ELISA format, various assay formats are possible.

One embodiment of our novel assay, which we shall call the $T^2$-ELISA method, comprises the capture of an autoantigen (target protein) onto the microtiter plate well with one epitope tag (capture tag) followed by reading the autoantibody (probe) signal in the same well, while using the other tag (detection tag) to normalize for the amount of protein expressed in separate Wells. In order to compare our $T^2$-ELISA assay with an FDA-approved, commercially available, semi-quantitative ELISA assay for the detection of anti-sp100 IgG antibodies in human serum (QUANTALite® ELISA assay for sp100; INOVA Diagnostics, San Diego, Calif.) we set up the following experiment: Briefly, autoantigens are cell-free expressed, purified in-line with the microtiter plate based assay (i.e. captured on well surface) and screened against patient sera for autoantibody binding using a traditional sandwich ELISA format. Enzyme-tagged detector antibodies (each having a different chemiluminescent substrate) are added in series, after which two different chemiluminescent substrates are added to the appropriate wells one at a time in order to read both autoantibody binding as well as the detection tag (normalization signal).

Autoantigen Expression

The entire Open Reading Frame (ORF) of the putative autoantigen (in this case human Sp100) was cloned, using standard and accepted molecular biology practices, into a plasmid vector compatible with cell-free protein expression, containing the T7 RNA polymerase promoter, a Kozak (ribosome binding) sequence, a start codon, an N-terminal VSV-G epitope tag (YTDIEMNRLGK (SEQ ID NO: 19)), and a C-terminal HSV epitope tag (QPELAPEDPED (SEQ ID NO: 20)) in addition to the ORF insert. As source DNA for cloning into the expression vector, full-length sequence-verified clones were purchased from OpenBiosystems (Huntsville, Ala.). Expression vectors were verified for the correct ORF insert using standard EcoRI digestion methods.

Autoantigens were produced from the aforementioned plasmid clones by cell-free protein expression. Cell-free protein expression reactions were performed using a transcription/translation coupled rabbit reticulocyte lysate system (TNT® T7 Quick for PCR DNA system; Promega, Madison, Wis.) according to the manufacturer's instructions. Autoantigen expression reactions contained the cognate plasmid DNA while blank expression reactions lacked only the plasmid DNA. Expression reactions were stopped by diluting 1/20 in TDB [1% BSA (w/v) and 0.1% (v/v) Triton X-100 in TBS-T (50 mM Tris, pH 7.5, 200 mM NaCl, 0.05% (v/v) Tween-20)].

Enzyme-Linked Immunosorbent Assay (ELISA) of Autoantigens

Nunc-Immuno™ Microwell™ Polysorp® 96 well polystyrene microtiter plates, (untreated, white opaque, flat bottom), (Nunc Brand from Thermo-Fisher Scientific; Rochester, N.Y.) were used for a sandwich type Enzyme-Linked Immunosorbent Assay (ELISA). Plates were coated with 0.5 µg/mL of a mouse monoclonal anti-HSV Tag® capture antibody (EMD Biosciences, Inc., San Diego, Calif.) in sodium carbonate/bicarbonate pH 9.3 for 30 min with shaking (50 µL/well). All plate washing consisted of manual addition of TBS-T (wells filled to maximum, i.e. 300 µ) followed by vacuum aspiration, repeated 4x. All plate washes were performed in this manner unless noted otherwise. Plates were then blocked for 30 min at 300 µL/well in 1% BSA (w/v) in TBS-T. The solution was removed from the plates and the aforementioned stopped (i.e. diluted) cell-free expression reactions (autoantigen and blank reactions) were then added at 100 µl/well and shaken for 30 min. Plates were washed and serum samples (diluted at 1/1,000 in 1% BSA (w/v) in TBS-T) were added at 100 µL/well and shaken for 30 min. Plates were washed and serum samples (diluted at 1/1,000 in 1% BSA (w/v) in TBS-T) were added at 100 µL/well and shaken for 30 min. Each serum sample was run against duplicate wells of autoantigen and duplicate wells of the cell-free expression blank with an additional set of duplicate wells of the cell-free expression blank designated for VSV-G epitope tag detection [thus received plain 1% BSA (w/v) in TBS-T instead of diluted serum]. Wells designated for detection of the VSV-G epitope tag then received an anti-VSV-G horseradish peroxidase (HRP) labeled monoclonal antibody, while wells designated for detection of serum autoantibody received a mouse anti-[human IgG] HRP labeled monoclonal secondary antibody. Plates were subsequently washed 4x by manual addition of TBS-T (wells filled to maximum) followed by vacuum aspiration as described earlier in this Example. Wells designated for detection of the VSV-G epitope tag then received an anti-VSV-G horseradish peroxidase (HRP) labeled monoclonal antibody (Clone P5D4, Roche Applied Science, Indianapolis, Ind.) diluted 1/20,000 in 1% BSA/TBS-T. Wells designated for detection of serum autoantibody received a mouse anti-[human IgG] HRP labeled monoclonal secondary antibody (minimum cross-reactivity with mouse immunogobulin; Jackson ImmunoResearch Laboratories, Inc, West Grove, Pa.) diluted 1/20,000 in 1% BSA/TBS-T. Plates were shaken for 30 min. The solutions were then manually dumped from the plates by inversion followed by vigorous patting of the plates inverted on a dry paper towel to remove residual fluid. Plates were then washed as described earlier in this Example. Chemiluminescence signal was generated by the addition of 50 µL/well of SuperSignal ELISA Pico Chemiluminesence Substrate (Pierce Brand from Thermo Fisher Scientific, Rockford, Ill.). Plates were developed by shaking for 15 min and then read on a LumiCount luminescence plate reader (1 s exposure, PMT of 650V, gain 1) (Packard/PerkinElmer Life and Analytical Sciences, Inc., Boston, Mass.).

QUANTALite® ELISA Assay for sp100

Assay was performed according to manufacturer's instructions (INOVA Diagnostics, San Diego, Calif.).

Results:

We compared our $T^2$-ELISA to a commercial ELISA to test concordance (FIG. 11). This was done by testing 35 primary biliary cirrhosis (PBC) sera for autoantibodies against the known autoantigen Sp100. The commercial ELISA (INOVA Diagnostics, San Diego, Calif.) is an FDA-approved colorimetric ELISA comprised of autoantigen immobilized on the plate surface and was performed according to the manufacturer's instructions. Data are shown in FIG. 11 using a subset of the PBC cohort. The INOVA standard positive control serum used to calculate "Units" was run on both assays to convert the signals of each assay to the same scale (Units/µL of Neat Serum). Both assays were scored using the INOVA methodology, i.e. positive when units >25; which is what the "Low Positive" standard positive control serum is set to. As FIG. 11 indicates, in terms of scoring sera positive or negative, there is perfect concordance. However, the INOVA assay saturates very quickly, while the $T^2$-ELISA displays at least a 5-fold wider dynamic range.

Example 10

Comparison of $T^2$-ELISA with a Conventional Commercial ELISA for p53 Tumor Associated Autoantibody Detection from Cancer Sera in Order to Assess Concordance Autoantigen Expression for $T^2$-ELISA The entire Open Reading Frame (ORF) of human p53 was cloned, using standard and accepted molecular biology practices, into a plasmid vector compatible with cell-free protein expression, containing the T7 RNA polyrnerase promoter, a Kozak (ribosome binding) sequence, and C-terminal HSV (QPELAPEDPED (SEQ ID NO: 20)) and 6X His epitope tags, in addition to the ORF insert. Expression vectors were verified for the correct ORF insert using DNA sequencing.

The p53 autoantigen was produced from the aforementioned plasmid clone by cell-free protein expression. Cell-free protein expression reactions were performed using a transcription/translation coupled rabbit reticulocyte lysate system (TNT® T7 Quick for PCR DNA system; Promega, Madison, Wis.) according to the manufacturer's instructions. Autoantigen expression reactions contained the cognate plasmid DNA while blank expression reactions lacked only the plasmid DNA. Expression reactions were stopped by diluting 1/20 in TDB [1% BSA (w/v) and 0.1% (v/v) Triton X-100 in TBS-T (50 mM Tris, pH 7.5, 200 mM NaCl, 0.05 % (v/v) Tween-20)].

Enzyme-Linked Immunosorbent Assay ($T^2$-ELISA) of Autoantigens

Sera (ProMedDx, Norton, Mass.) from 34 patients diagnosed with colorectal cancer (CRC) of varying stages (ranging from AJCC/UICC Stage I to Stage IV) and from 7 disease-free individuals were screened in duplicate for autoantibodies against the p53 tumor autoantigen using a commercial ELISA (EMD Biosciences, Inc., San Diego, Calif.) comprised of recombinant human cellular expressed p53 and the $T^2$-ELISA. For the commercial ELISA, sera, pre-cleared with a 5 minute spin at 16,000×g in a microcentrifuge at 4° C., were diluted 1:100 and run in duplicate following instructions provided by the manufacturer and described in the literature [Oshikawa and Sugiyama (2000) Respir Med 94: 1085-91]. A validated negative control sera (provided by the manufacturer) was also run in duplicate and used to determine assay background. Absorbance readings at 450 nm for each well were collected on a SpectraMax Plus384 microplate spectrophotometer (Molecular Devices, Sunnyvale, Calif.).

For screening sera with the $T^2$-ELISA, the following protocol was used. Nunc-mmuno™ Microwell™ Polysorp® 96 well polystyrene microtiter plates, (untreated, white opaque, flat bottom), (Nunc Brand from Thermo-Fisher Scientific, Rochester, N.Y.) were used for a sandwich type Enzyme-Linked immunosorbent Assay (ELISA). Plates were coated with 0.5 µg/mL of a mouse monoclonal anti-HSV Tag® capture antibody (EMD Biosciences, Inc., San Diego, Calif.) in sodium carbonate/bicarbonate pH 9.3 for 30 min with shaking (50 µL/well). Plates were then manually washed 4x in 300.mu.1 TBS-T using a multichannel pipette to add the wash buffer and inversion of the plates followed by vigorous patting of the inverted plates on a dry paper towel to remove the wash buffer and residual fluid. Blocking was performed for 30 min with 300.mu.L/well in 1 % BSA (w/v) in TBS-T. The solution was removed from the plates as just described and the aforementioned stopped (i.e. diluted) cell-free expression reactions (autoantigen and blank reactions) were then added at 100.mu.L/well and shaken for 30 min. Plates were washed as above and serum samples (pre-cleared with a 5 minute spin at 16,000×g in a microcentrifuge at 4° C.) were diluted at 1/2,000 in 1% BSA (w/v) in TBS-T. A volume of 100 µL serum/well was added and plates were shaken for 30 minutes at room temperature. Each serum sample was run against duplicate wells on each of two separate plates, one containing cell-free expressed autoantigen and the other containing cell-free expression blank (expression reaction minus DNA template). Following serum incubation, serum was removed by vacuum aspiration and plates were washed 4× with TBS-T. For serum autoantibody detection, 100 µl of a mouse anti-[human IgG] HRP labeled monoclonal secondary antibody (minimum cross-reactivity with mouse immunoglobulin; Jackson ImmunoResearch Laboratories, Inc, West Grove, Pa.) diluted 1/20,000 in 1% BSA/TBS-T was added to each well. Plates were shaken for 30 min at room temperature followed by washing 4× in 300 .mu.1 TBS-T as described above. Chemiluminescence signal was generated by the addition of 50 µL/well of SuperSignal ELISA FEMTO Chemiluminesence Substrate (Pierce Brand from Thermo Fisher Scientific, Rockford, Ill.). Plates were developed by shaking for 15 seconds at room temperature and then read on a Lumi-Count luminescence plate reader (1 s exposure, PMT of 693V, gain 1) (Packard/PerkinElmer Life and Analytical Sciences, Inc., Boston, Mass.).

Results:

To test concordance of our $T^2$-ELISA with the commercial ELISA in detecting autoantibodies against p53, a known tumor autoantigen, 34 sera from CRC patients (FIG. 12, 1-34) and 7 sera from disease-free, "normal" individuals [FIG. 12, N1-N7 (outlined by green box)] were tested in duplicate on each of the two assays. After running each ELISA, signal minus background values were first calculated for each sera. For the commercial ELISA, background was calculated as the average of the raw values from each of the two wells probed with a validated negative sera provided by the manufacturer. This background value was then subtracted from the raw values of each of the test wells probed with either CRC or "normal" sera, yielding duplicate signal minus background values for each sera. Note that a floor of zero was set for these signal-minus-background values (i.e. any negative values were set to zero). The duplicate signal-minus-background values for each sera were then averaged yielding a single, average, signal-minus-background value. For the $T^2$-ELISA, background was determined as the average of the duplicate wells for each serum run against the cell-free expression blank (minus DNA template reaction). This background value was then independently subtracted from each of the duplicate raw values for the same serum run against cell-free expressed autoantigen (p53) yielding two signal-minus-background values for each sera. As with the analysis of the commercial ELISA data, a floor of zero was once again set for the signal-minus-background values. The duplicate signal-minus-background values for each sera were then averaged yielding a single, average, signal-minus-background value for each sera. Next, for both the commercial ELISA and $T^2$-ELISA, sera were simply scored as analytically positive or negative (FIG. 12 shows only those sera scored as analytically positive) in order to check concordance between the two assays. For this, both of the following criteria must have been met for each serum-autoantigen pair in order for that pair to have been scored as analytically positive in the ELISA: i) a p-value ≤0.05 in a 1-tailed homoscedastic unpaired t-test on the raw ELISA values from the duplicate wells of the autoantibody signal (serum versus autoantigen) compared to values from the duplicate wells of the background signal (same serum versus blank expression wells); ii) autoantibody signal-to-background ratio ≥2. Serum-autoantigen pairs not passing these criteria are set to 0. Finally, for each assay independently, the average signal-minus-background values of those sera scored as analytically positive were normalized to the serum with the highest value in that same assay (CRC 12 for the commercial ELISA and CRC19 for the $T^2$-ELISA), which was set to 100%. These normalized values were then plotted with error bars representing standard deviations (FIG. 12). As can be noted in FIG. 12, all sera that scored positive for p53 autoantibodies in the commercial ELISA also scored positive (with an approximately equal relative strength of signal, also) in the $T^2$-ELISA. Additionally, one additional CRC serum (serum 18), but no additional normal serum, was scored slightly positive by the $T^2$-ELISA and negative by the commercial ELISA. Together, the data suggest that the $T^2$-ELISA is at least as sensitive as the commercial ELISA, and perhaps may even be slightly more sensitive as indicated by the ability to identify one additional CRC sample. Neither assay detected an autoantibody signal in any of the normal sera, suggesting a very good concordance with respect to specificity, also.

Example 11

A Dual-Epitope Tag and Dual-Reporter Based Solid-Phase Heterogeneous Assay as a Tool for Detecting Interactions with Proteins The dual-tagged $T^2$-ELISA described in Example 2 utilizes a single-reporter system for autoantibody detection and target protein normalization. Whereas Example 2 demonstrates using separate wells for probe readout (autoantibody in that case) and epitope tag readout, this Example illustrates the ability of the assay to detect the binding of "probes" (e.g. drugs, oligonucleotides or antibodies) to the surface-immobilized cell-free expressed target proteins while being able to normalize for the amount of target protein on the same surface (i.e. same well), using a dual-reporter system. Although the Example shown here relates to detection of autoantibody binding from human serum to cell-free expressed autoantigens as the target proteins, the methodology is broadly applicable. Furthermore, although the assay format used in this Example is a micro-well (microtiter) plate-based ELISA format, various assay formats are possible.

In order to show that it is possible to capture an autoantigen (target protein) onto the microtiter plate well with one epitope tag (capture tag) and normalize with the other (detection tag), while still reading the autoantibody (probe) signal in the same well, we performed the $T^2$-ELISA assay as described in Example 2, with the following exceptions: following cell-free expression and antigen capture, and the sequential addition of enzyme-tagged antibodies, two different chemiluminescent substrates were also added sequentially, thereby enabling both autoantibody binding signals and detection tag (normalization) signals to be read sequentially within the same well.

In addition to showing that dual detection within the same well is possible, we directly compare dual-well detection to single-well detection on a variety of autoantigens with various patient sera, in order to demonstrate the potential advantages of per-well-normalization, namely, by normalizing for possible protein expression or capture variations.

Autoantigen Expression

Performed as in Example 2, with the exception of Rap55, which was expressed from column-purified PCR product.

Rap55 was PCR-amplified from cDNA using standard and accepted molecular biology practices. Primers were designed to yield a PCR product compatible with cell-free protein expression, containing the T7 RNA polymerase promoter, a Kozak (ribosome binding) sequence, a start codon, an N-terminal VSV-G epitope tag (YTDIEMNRLGK (SEQ ID NO: 19)), and a C-terminal HSV epitope tag (QPELAPEDPED (SEQ ID NO: 20)) in addition to the Rap55 insert.

Enzyme-Linked Immunosorbent Assay ($T^2$-ELISA) of Autoantigens

Performed as in Example 2, with the following exceptions. For the dual-reporter assay (different from the single-reporter assay as described in Example 2) there were no additional wells set aside for VSV-G epitope tag detection, since the tag and the probe (autoantibody) were detected sequentially in the same well. The enzyme-tagged antibodies were added sequentially to all the wells, followed each time by washing, as described here: First a mouse anti-[human IgG] alkaline phosphatase (AP) labeled monoclonal secondary antibody (minimum cross-reactivity with mouse immunoglobulin; Jackson ImmunoResearch Laboratories, Inc, West Grove, Pa.) diluted 1/20,000 in 1% BSA/TBS-T was added. Plates were then shaken for 30 min. The solutions were then manually dumped from the plates by inversion followed by vigorous patting of the plates inverted on a dry paper towel to remove residual fluid. Plates were then washed manually as described earlier in Example 8. This process was repeated for an anti-VSV-G horseradish peroxidase (HRP) labeled monoclonal antibody (Clone P5D4, Roche Applied Science, Indianapolis, Ind.) diluted 1/20,000 in 1% BSA/TBS-T. An AP chemiluminescence signal was generated by the addition of 50 µL/well of BM Chemiluminescence ELISA Substrate (Alkaline Phosphatase Detection; Roche Diagnostics, GmbH, Mannheim, Germany) following the manufacturer's instructions. After allowing the signal to develop, plates were read as described in Example 8, followed by a second reading where PMT was set relative to the highest signal on the plate. After reading the plate, the plate was washed manually followed by the addition of 50 µL/well of SuperSignal ELISA Pico Chemiluminescence Substrate (Pierce Brand from Thermo Fisher Scientific, Rockford, Ill.). Plates were developed by shaking for 15 min and then read as described in Example 1, followed by a second reading where PMT was set relative to the highest signal on the plate.

Different from the data in Table IV, the dual-reporter and single-reporter ELISAs performed for FIG. 13 were washed with the aid of a robotic plate washer. Specifically, Plates were washed 6× in TBS-T (wells filled to maximum) on an ELx405 Select Robotic Plate Washer (BioTek, Winooski, Vt.). Following the addition of serum, in order to avoid contamination of the robotic plate washer with human serum, plates were subsequently washed 4× by manual addition of TBS-T (wells filled to maximum) followed by vacuum aspiration and then washed 6× in the robotic plate washer as described earlier in this Example.

Results:

First, in order to establish that the dual-detection process of the $T^2$-ELISA is as efficient as single detection, we directly compared this using Rap55, a known PBC autoantigen, and a PBC patient serum sample. As seen in Table IV-A, the autoantibody (AP) signal [calculated as AP signal–noise (i.e. same serum versus blank expression wells)] from the dual-reporter assay was calculated as a percent of the corresponding autoantibody signal from the single-reporter (AP) assay. Both methods yielded almost identical results (dual reporter AP signal was 97% of corresponding single reporter, dual reporter HRP signal was 96% of corresponding single reporter), clearly demonstrating that detection of the VSV-G epitope tag (HRP) does not inhibit the subsequent detection of the autoantibody signal (AP) in the same well. Likewise, autoantibody (AP) detection does not significantly interfere with VSV-G epitope tag (HRP) detection in the same well. We also calculated signal-to-noise ratios for the autoantibody (AP) signal: [calculated as AP signal/noise (i.e. same serum versus blank expression wells)] from the dual-reporter assay as compared to the single-reporter assay (Table IV-B) and demonstrated that dual detection within the same well does not decrease the signal-to-noise ratios in the slightest.

Second, dual-reporter and single-reporter $T^2$-ELISA assays were compared for several serum-antigen pairs. FIG. 13 shows example data from $T^2$-ELISA for systemic lupus erythematosus (SLE), PBC and normal patient sera versus a variety of known autoantigens (CENPB, Ro-60, Smith B, and Sp140). As a reference, samples were already known to be positive for the various autoantigens as reported by clinical annotation of samples. Autoantibody. Unit ELISA values were determined for each serum-autoantigen pair, for which the average and standard deviation (errors bars) was calculated and plotted in FIG. 13 individually for the aforementioned autoantigens. Note that a floor of zero was set for the Autoantibody Units. Normal sera tested with CENPB are indeed negative as expected. Signal-to-noise ratios of positive results ranged from 3:1 (Smith B vs. SLE-H) to 300:1 (SP140 vs. PBC-1-21). This experiment also compares the dual-reporter assay to a single-reporter assay whereby separate wells were used solely for the detection of the VSV-G normalization epitope tag. The potential advantage of dual-reporter detection is that each autoantibody signal is normalized per well for possible protein expression (e.g. day-to-day) or capture variations (intra- or inter-assay). The data shows no significant detriment to using the dual-reporter assay. Furthermore, as expected, standard deviations of the dual-reporter assay, which is a per-well normalization, are significantly less than the single-reporter assay, which normalizes only on a per assay (per plate) basis.

Example 12

Detection of Autoantibodies Against the Novel Primary Biliary Cirrhosis (PBC) Autoantigens HK1 and KLHL12 Recombinantly Expressed in a Wheat Germ Based System and Assayed Using a Direct Autoantigen Coating to the Surface of the ELISA Plate Autoantigens and ELISA Assay In this Example, a key feature is that the ELISA assay was performed on polystyrene microtiter plates directly coated with pre-purified recombinantly expressed autoantigens (instead of antibody mediated in situ capture/purification to ELISA plate surface as in $T^2$-ELISA). Another notable feature is that HK1 and KLHL12 were expressed in a different system as compared to previous Examples. Human HK1 and KLHL12 full-length recombinant proteins expressed in a cell-free wheat germ based system and purified by their N-terminal GST fusion tag were purchased from Abnova (Taiwan). The plates were coated overnight with 100 µL per well of 0.5 µg/mL recombinant protein diluted in PBS. As detailed in Example 2, plates were then washed 6× in TBS-T (wells filled to maximum) and then were blocked for 30 min at 300 µL/well in 1% BSA (w/v) in TBS-T. The block solution was removed from the plates and serum samples (diluted at 1/100) (diluent from INOVA Diagnostics' QUANTALite® ELISA system; San Diego, Calif.) were added at 50 µL/well and shaken for 30 min at room temperature. Plate washing and addition of the secondary antibody is described in Example 2. The ELISA was developed using the colorimetric substrate and stop solution from INOVA Diagnostics' QUANTALite® ELISA system (San Diego, Calif.) according to the manufacturer's instructions.

Results:

FIG. 14 shows that the colorimetric assay works well for HK1 versus several PBC and normal sera and results are 100% concordant with the expected results (based on the microarray and $T^2$-ELISA results; see Examples 1 and 2). Note these expected scores are indicated by "+" and "−" in the graph. Note that the red line is the cutoff for this assay (set at 2 standard deviations above the mean for the 4 expected negative samples). Also note that this is direct plate coating with a recombinant antigen and there is no background subtraction here (it is not needed with no capture antibody present). Finally, note that N-03 is in fact supposed to be positive (and PBC-04 and PBC-05 negative) based on previous results from Examples 1 and 2.

Similarly, FIG. 15 for KLHL12 shows colorimetric assay results that are 100% concordant with the expected results (based on the microarray and $T^2$-ELISA results; see Examples 1 and 2). Note these expected scores are indicated by "+" and "−" in the graph. The cutoff is indicated as the red line and was set 2 standard deviations above the mean for the 4 expected negative samples. N-03 is expected to be positive and PBC-02 and PBC-07 negative based on previous results from Examples 1 and 2.

Example 13

Detection of Autoantibodies in Primary Biliary Cirrhosis (PBC) Using Homologs of HK1 and KLHL12

Information in the following paragraphs was obtained from the publically available UniProt database [The-UniProt-Consortium (2009) Nucleic Acids Res 37: D169-74] as well as the various publically available NCBI databases [National (United States) Center for Biotechnology Information].

Hexokinase 1 (HK1) is a protein which localizes to the outer membrane of mitochondria. Alternative splicing the gene encoding HK1 results in five transcript variants which encode different isoforms. Each isoform has a distinct N terminus but the remainder of the protein is identical among all isoforms [NCBI RefSeq]. Therefore, it is reasonable to assume that any of the aforementioned isoforms would be sufficient for detection of autoantibodies to hexokinase 1 in Primary Biliary Cirrhosis (PBC).

Furthermore, Hexokinase 1 is one member of a family of proteins, which includes Hexokinase 2, Hexokinase 3, Glucokinase (Hexokinase 4), and Hexokinase Domain Containing 1. The aforementioned proteins demonstrate significant sequence homology, (e.g. using the NCBI BLAST engine, human HK1 and HK2 have 73% identities and 86% positives; NCBI Accessions BC008730.2 coding sequence and NP_0001.80.2, respectively) as well as share common conserved domains, including hexokinase domains_1 and _2 (pfam00349 and pfam03727, respectively), as well as the conserved multi-domain COG5026 Hexokinase [carbohydrate transport and metabolism].

Kelch-like 12 (KLHL12) is a protein involved in the ubiquitin ligase conjugation and wnt cell-signaling pathway. It contains 6 kelch repeat domains and a BIB (POZ) domain. Several Kelch-like and other proteins exist containing the aforementioned domains (e.g. see Table VI).

Due to both protein sequence similarity and the phenomena of intra- and inter-molecular epitope spreading [Vanderlugt and Miller (2002) Nat Rev Immunol 2: 85-95], we fully expect that the aforementioned HK1 and KLHL12 homologs (see also Examples in Table VI) would show a similar performance with respect to the detection of disease-specific autoantibodies in Primary Biliary Cirrhosis (PBC). Furthermore, the use of homologs may increase diagnostic sensitivity and/or specificity. In this Example, this will be evaluated.

Autoantigen Expression

Will be performed as in Example 3 except that homologs of HK1 and KLHL12 will be expressed and used as autoantigens for detection of autoantibodies, such as those mentioned above in this Example and the examples of homologs listed in Table VI.

Dual-Tag Enzyme-Linked Immunosorbent Assay ($T^2$-ELISA) of Autoantigens

Will be performed as in Example 3.

Results:

As in Example 3, in order to set diagnostic scoring thresholds for a given autoantigen species, the $T^2$-ELISA assay will be run on a group of 22 normal patient sera and the cutoffs will then be set at 2 standard deviations above the mean for this normal cohort, for ~95% statistical confidence. The use of this method at 2-3 standard deviations is common practice (e.g. [Liu, Wang, Li, Xu, Dai, Wang and Zhang (2009) Scand J Immunol 69: 57-63]). The $T^2$-ELISA will then be run on 22 PBC patient sera (e.g. 22 AMA-negative and/or 22 AMA-positive). The autoantigen-specific cutoffs will then be used to score both the normal and PBC patients as autoantibody negative or positive. Autoantibody Unit calculations and data processing will be performed as in Example 3. Calculations of diagnostic sensitivity and specificity for each autoantigen species will then be performed as in Example 3.

Due to both protein sequence similarity and the phenomena of intra- and inter-molecular epitope spreading [Vanderlugt and Miller (2002) Nat Rev immunol 2: 85-95], the expectation is that at least some of the HK1 and KLHL12 homologs will show similar diagnostic performance as in Example 3 for AMA-positive and Example 4 for AMA-negative PBC where human HK1 and KLHL12 themselves were used. It is also expected that some may perform better, either in diagnostic sensitivity or specificity, or both.

DESCRIPTION OF THE FIGURES

FIG. 1: ELISA Based Pre-Validation of the PBC Autoantigen Hexokinase 1 (HK1) on Positive and Negative Serum Samples Randomly Selected from the Microarray Analyses. The graphed data are from the ELISA. The "+" and "−" denote if a given serum was positive or negative for HK1 autoantibodies based on either the "ELISA" assay or microarray ("Array") analyses. Serum samples prefixed with "N" are from healthy individuals, "PBC" from primary biliary cirrhosis patients, and "SLE" from systemic lupus erythematosus patients. Calculation of Autoantibody Units from the ELISA assay is detailed in Example 2.

FIG. 2: ELISA Based Pre-Validation of the PBC Autoantigen Kelch-Like 12 (KLHL12) on Positive and Negative Serum Samples Randomly Selected from the Microarray Analyses. The graphed data are from the ELISA. The "+" and "−" denote if a given serum was positive or negative for KLHL12 autoantibodies based on either the "ELISA" assay or microarray ("Array") analyses. Serum samples prefixed with "N" are from healthy individuals and "PBC" from primary biliary cirrhosis patients. Calculation of Autoantibody Units from the ELISA assay is detailed in Example 2.

FIG. 3: ELISA Based Validation of the PBC Autoantigen Hexokinase 1 (HK1) on a new PBC Patient Cohort Never Before Tested on the Proteome Microarrays. The graphed data are the $Log_2$ transformed Autoantibody Units from the ELISA analysis. Calculation of Autoantibody Units from the ELISA assay is detailed in Example 2. Patient samples were scored as HK1 negative or positive based on the cutoff values (dotted red line) which were calculated as detailed in Example 3. The red boxed region indicates the PBC cohort and the unboxed region the normal cohort.

FIG. 4: ELISA Based Validation of the PBC Autoantigen Kelch-Like 12 (KLHL12) on a New PBC Patient Cohort Never Before Tested on the Proteome Microarrays. The graphed data are the $Log_2$ transformed Autoantibody Units from the ELISA analysis. Calculation of Autoantibody Units from the ELISA assay is detailed in Example 2. Patient samples were scored as KLHL12 negative or positive based on the cutoff values (dotted red line) which were calculated as detailed in Example 3. The red boxed region indicates the PBC cohort and the unboxed region the normal cohort.

FIG. 5: Detection of the PBC Autoantigen Hexokinase 1 (HK1) on a New PBC Antimitochondrial Antibody (AMA)-Negative Cohort. The graphed data are the $Log_2$ transformed Autoantibody Units from the ELISA assay, as calculated in Example 2. Dotted red line indicates the diagnostic scoring threshold, as previously determined in Example 3. HK1 detected 4 of 17 AMA-negative PBC patients (24% sensitivity). Of note, one AMA-negative PBC patient (green bar) was detected by HK1 but undetected by any of the commercially available FDA-approved ELISA assays from INOVA Diagnostics for PBC.

FIG. 6: Detection of the PBC Autoantigen Kelch-like 12 (KLHL12) on a New PBC Antimitochondrial Antibody (AMA)-Negative Cohort. The graphed data are the $Log_2$ transformed Autoantibody Units from the ELISA assay, as calculated in Example 2. Dotted red line indicates the diagnostic scoring threshold, as previously determined in Example 3. KLHL12 detected 6 of 17 AMA-negative PBC patients (35% sensitivity). Of note, one AMA-negative PBC patient (green bar) was detected by KLHL12 but undetected by any of the commercially available FDA-approved ELISA assays from INOVA Diagnostics for PBC.

FIG. 7: Venn Diagram—Novel PBC-Specific Autoantigens, HK1 and KLHL12, Capture Previously Undetectable AMA-Negative PBC Patients. Each number represents a patient.

FIG. 8: Detection of Hexokinase 1 (HK1) and Kelch-like 12 (KLHL12), in Addition to INOVA Diagnostic's MIT3 Assay, May Reveal a Large Number of Previously Undiagnosed PBC Patients With Atypical Indirect Immunofluorescence Staining (IIF). Serum samples prefixed with "Cyto" or "NM" are from patients with diffuse cytoplasmic or nuclear membrane IIF staining, respectively. To avoid scale effects, graphed data for each antigen is normalized as a percent of the patient having the maximum autoantibody units for that antigen (that patient is marked with a blue arrow for each antigen). We set the Y-axis to INOVA's MIT3 cut-off of 25 units, which corresponded to 17%. All bars shown in the graph represent positive results and the lack of a bar a negative result. The "High Positive" is a selected positive control serum for each of the autoantigens.

FIG. 9A: HK1 Detection By Colorimetric ELISA in Selected PBC Patients—Concordance with Chemiluminescence ELISA Readout. Colorimetric ELISA results are plotted as the signal minus background, with the background being the same serum run against an expression blank (no expressed autoantigen). The chemiluminescence ELISA score is indicated below the X-Axis by a "+" (positive) or "−" (negative). The scores for the chemiluminescent ELISA were those as already determined in Example 4 for the same sera. The bar with the green outline corresponds to the same sample from Example 4 (PB-AMN-044) to score negative on all available PBC ELISA assays from INOVA Diagnostics but positive for HK1.

FIG. 9B: KLHL12 Detection By Colorimetric ELISA in Selected PBC Patients—Concordance with Chemiluminescence ELISA Readout. Colorimetric ELISA results are plotted as the signal minus background, with the background being the same serum run against an expression blank (no expressed autoantigen). The chemiluminescence ELISA score is indicated below the X-Axis by a "+" (positive) or "−" (negative). The scores for the chemiluminescent ELISA were those as already determined in Example 4 for the same sera. The bar with the green outline corresponds to the same sample from Example 4 (PB-AMN-263) to score negative on all available PBC ELISA assays from INOVA Diagnostics but positive for KLHL12.

FIG. 10: Colorimetric Dot Blot of PBC Autoantigen HK1 Probed with PBC and Normal Patient Sera. Newly discovered PBC Autoantigen HK1 was spotted onto nitrocellulose, as well as buffer (negative control) and human IgG (positive control). Diluted sera from a PBC patient and normal patient was allowed to bind and washed before adding colloidal gold labeled anti-human IgG. "hIgG" is human IgG positive control; "AAg" is new PBC autoantigen HK1; "Ctrl" is negative control (carrier buffer).

FIG. 11: Comparison of $T^2$-ELISA to a Commercial (INOVA Diagnostics) ELISA Using the Sp100 Autoantigen and PBC Sera. Serum samples prefixed with "PBC" are from primary biliary cirrhosis patients. Red boxed region represents INOVA ELISA results; yellow boxed region represents $T^2$-ELISA results. *Units above the "Low Positive" control (red line) are scored as diagnostically positive.

FIG. 12: $T^2$-ELISA Versus Conventional ELISA for p53 Autoantibody Detection Cancer Sera. Normal sera are prefixed with an "N" (green box) and all others are CRC sera. Data are normalized as a percent of the maximum sera for that assay.

FIG. 13: Dual-Reporter and Single-Reporter $T^2$-ELISA Assays Against Various Serum-Antigen Pairs. The graphed data are the Autoantibody Units from the ELISA analysis. Calculation of Autoantibody Units from the ELISA assay is detailed in Example 12. Blue text denotes the antigen. Serum samples prefixed with "N" are normal (from healthy individuals), "SLE" systemic lupus erythematosus and "PBC" primary biliary cirrhosis.

FIG. 14: Autoantibody Detection in ELISA with Pre-Purified Human Hexokinase 1 Autoantigen (HK1) Coated Directly to Polystyrene Microtiter Plate Surface. Pre-purified expressed recombinant protein autoantigen was bound directly to the polystyrene microtiter ELISA plate surface and used to assay patient serum for the presence of autoantibodies. The expected result, based on previous microarray and $T^2$-ELISA data (Examples 1 and 2), is listed below the X-Axis as "+" (autoantibody positive) or "−" (autoantibody negative). The actual result of the assay in this Example, is shown based on the scoring cutoff in the bar graph (red dotted line), which was calculated as 2 standard deviations above the mean for the 4 expected negative samples.

FIG. 15: Autoantibody Detection in ELISA with Pre-Purified Human Kelch-Like 12 Autoantigen (KLHL12) Coated Directly to Polystyrene Microtiter Plate Surface. Pre-purified expressed recombinant protein autoantigen was bound directly to the polystyrene microtiter ELISA plate surface and used to assay patient serum for the presence of autoantibodies. The expected result, based on previous microarray and $T^2$-ELISA data (Examples 1 and 2), is listed below the X-Axis as "+" (autoantibody positive) or "−" (autoantibody negative). The actual result of the assay in this Example, is shown based on the scoring cutoff in the bar graph (red dotted line), which was calculated as 2 standard deviations above the mean for the 4 expected negative samples.

FIG. 16: Quantile Normalized Proteome Microarray (ProtoArray) Autoantibody Data for Human Hexokinase 1 (HK1) for 92 Distinct Serum Samples. Autoantibody fluorescence signal intensity, "Array Signal" (quantile normalized across the entire 92-member microarray set on a per lots basis), for each of the patient serum samples is shown for the novel autoantigen human HK1. PBC=Primary Biliary Cirrhosis; Normal or Norm=Healthy Individuals; SLE=Systemic Lupus Erythematosus; SjS=Sjögren's Syndrome; CRC=Colorectal Cancer; AIH=Autoimmune Hepatitis.

FIG. 17: Quantile Normalized Proteome Microarray (ProtoArray) Autoantibody Data for Human Kelch-Like 12 (KLHL12) for 92 Distinct Serum Samples. Autoantibody fluorescence signal intensity, "Array Signal" (quantile normalized across the entire 92-member microarray set on a per lots basis), for each of the patient serum samples is shown for the novel autoantigen human KLHL12. PBC=Primary Biliary Cirrhosis; Normal or Norm=Healthy Individuals; SLE=Systemic Lupus Erythematosus; SjS=Sjögren's Syndrome; CRC=Colorectal Cancer; AIH=Autoimmune Hepatitis.

TABLE I

Primary Biliary Cirrhosis (PBC) Autoantigens

| NCBI GenBank Accession (ID of Nucleic Acid Coding for Protein) | Gene | Fasta Header/Description | M-Statistics P Value | Diagnostic Sensitivity (S) & Specificity (P) in PBC vs all Non PBC |
|---|---|---|---|---|
| BC008730.2 | HK1 | >gi\|33869444\|gb\|BC008730.2\| *Homo sapiens* hexokinase 1, transcript variant 1, mRNA (cDNA clone MGC: 1724 IMAGE: 3163058), complete cds | 0.00000000012 | By Hit Calling Method: (S) 89% (P) 84% By M-Statistics Method: (S) 85% (P) 90% |
| NM_021633.2 | KLHL12 | >gi\|21361889\|ref\|NM_021633.2\| *Homo sapiens* kelch-like 12 (*Drosophila*) (KLHL12), mRNA | 0.000076 | By Hit Calling Method: (S) 33% (P) 98% By M-Statistics Method: (S) 40% (P) 97% |

TABLE II

Compiled ELISA Results for PBC-Specific Autoantigens on Antimitochondrial Antibody (AMA)-Negative PBC Sera PBC-Positive AMA-Negative Sera

| | INOVA | | | | AmberGen | |
|---|---|---|---|---|---|---|
| | | | | PBC Screen | | |
| Sera ID | MIT3 | Gp210 | Sp100 | IgG/IgA | HK1 | KLHL12 |
| PB-AMN-005 | − | − | + | + | + | − |
| PB-AMN-031 | + | − | + | + | − | − |
| PB-AMN-033 | + | − | E | + | − | − |
| *PB-AMN-044 | − | − | − | − | + | − |
| PB-AMN-077 | − | − | + | E | − | + |

TABLE II-continued

Compiled ELISA Results for PBC-Specific Autoantigens on Antimitochondrial Antibody (AMA)-Negative PBC Sera PBC-Positive AMA-Negative Sera

| | INOVA | | | | AmberGen | |
|---|---|---|---|---|---|---|
| | | | | PBC Screen | | |
| Sera ID | MIT3 | Gp210 | Sp100 | IgG/IgA | HK1 | KLHL12 |
| △PB-AMN-084 | − | − | − | − | − | − |
| PB-AMN-095 | − | + | − | + | E | − |
| PB-AMN-105 | − | + | − | − | − | − |
| PB-AMN-109 | − | − | + | − | − | + |
| PB-AMN-110 | + | − | + | + | − | + |
| PB-AMN-120 | + | + | − | + | + | + |
| PB-AMN-217 | − | − | + | + | − | − |
| PB-AMN-223 | − | − | + | + | − | − |
| PB-AMN-224 | − | − | + | + | − | + |
| PB-AMN-225 | − | − | + | + | − | − |
| PB-AMN-262 | − | − | + | + | + | − |
| *PB-AMN-263 | − | − | − | − | − | + |

*Negative by all 4 INOVA tests but detected by AmberGen
△Negative by INOVA and AmberGen tests
E Equivocal-presence or absence of autoantibodies unable to be determined

TABLE III

ELISA Scores for PBC Patient Sera.

| | | Sp100 | Sp140 |
|---|---|---|---|
| Serum ID | INOVA Score | $T^2$-ELISA Score | $T^2$-ELISA Score |
| PB-AMP-002 | + | + | + |
| PB-AMN-005 | + | + | − |
| PB-AMP-006 | − | − | − |
| PB-AMP-011 | − | − | − |
| PB-AMP-018 | + | + | − |
| *PB-AMP-020 | − | − | + |
| PB-AMP-021 | + | + | + |
| PB-AMP-024 | + | + | − |
| PB-AMP-029 | + | + | − |
| PB-AMN-031 | + | + | − |

TABLE III-continued

ELISA Scores for PBC Patient Sera.

| | Sp100 | | Sp140 |
|---|---|---|---|
| Serum ID | INOVA Score | T²-ELISA Score | T²-ELISA Score |
| PB-AMN-033 | E | − | − |
| PB-AMP-035 | + | + | − |
| PB-AMP-036 | + | + | − |
| PB-AMP-039 | + | + | + |
| PB-AMP-046 | − | − | − |
| PB-AMP-047 | + | + | + |
| PB-AMP-048 | + | + | − |
| PB-AMP-059 | + | + | − |
| PB-AMP-063 | + | + | − |
| PB-AMP-066 | + | + | − |
| PB-AMP-068 | E | − | − |
| PB-AMN-077 | + | + | + |
| PB-AMP-080 | + | + | − |
| *PB-AMN-08 | − | − | + |
| PB-AMP-102 | + | + | − |
| PB-AMN-109 | + | + | + |
| PB-AMN-110 | + | + | − |
| PB-AMP-113 | + | + | − |
| PB-AMP-122 | + | + | + |
| PB-AMN-217 | + | + | + |
| PB-AMP-218 | + | + | − |
| PB-AMN-223 | + | + | + |
| PB-AMN-224 | + | + | − |
| PB-AMN-225 | + | + | − |
| PB-AMN-262 | + | + | + |

E = equivocal, i.e. inconclusive (too close to cutoff; only used in INOVA assay).
Asterisks indicate samples negative for Sp100 but positive for Sp140.

TABLE IV

Dual detection ELISA is as efficient as single detection ELISA

| Reporter Labeled Probes Added | AP Detection (Autoantibody) | HRP Detection (Rap55 Autoantigen Expression) |
|---|---|---|
| A. Single Reporter (Control) Versus Dual Reporter (Percent of Control) T²-ELISA Against Rap55 Autoantigen and PBC Patient Serum Percent of Control | | |
| anti-VSV-HRP | 0.02 | 100.00 (control) |
| anti-human-AP | 100.00 (control) | 0.23 |
| anti-VSV-AP then anti-human AP | 97.38 | 96.48 |
| B. Single Reporter Versus Dual Reporter T²-ELISA Against Rap55 Autoantigen and PBC Patient Serum (Signal to Noise) Signal to Noise | | |
| anti-VSV-HRP | 3.98 | 697.86 (control) |
| anti-human-AP | 20.15 (control) | 4.51 |
| anti-VSV-AP, then anti-human AP | 20.22 | 760.00 |

TABLE V

Human Hexokinase 1 (HK1) and Human Kelch-Like 12 (KLHL12) Sequences on ProtoArray v.4.0 (Invitrogen, Carlsbad, CA) (Example 1), on the T²-Elisa (several Examples) and on the Conventional ELISA of Example 12

| NCBI Genbank or Protein Accession and SEQ ID NO: | Fasta Header/Description | Sequence |
|---|---|---|
| | ProtoArray v.4.0 (Invitrogen, Carlsbad, CA) - Recombinant human HK1 and KHLK12 expressed in a baculovirus/Sf9 insect cell system. Note that HK1 and KLHL12 from the ProtoArray contained an N-terminal GST fusion tag (sequence not shown) commonly known to those skilled in the art. | |
| BC008730.2 SEQ ID NO: 1 | >gi\|33869444\|gb\|BC008730.2\| Homo sapiens hexokinase 1, transcript variant 1, mRNA (cDNA clone MGC:1724 IMAGE:3163058), complete cds | MIAAQLLAYYFTELkDDQVKKIDKYLYAMRLSDETLIDIMTRFRKEMKNGLSRDFNPTA TVKMLPTFVRSIPDGSEKGDFIALDLGGSSFRILRVQVNHEKNQNVHMESEVYDTPENI VHGSGSQLFDHVAECLGdFMEKRKIKDKKLPVGFTFSFPCQQSKIDEAILITWTKRFKA SGVEGADVVKLLNKAIKKRGDYDANIVAVVNDTVGTMMTCGYDDQHCEVGLIIGTGTNA CYMMELRHIDLVEGDEGRMCINTEWGAFGDDGSLEDIRTEFDREIDRGSLNPGKQLFEK MVSGMYLGELVRLILVKMAKEGLLFEGRITPELLTRGKFNTSDVSAIEKNKEGLHNAKE ILTRLGVEPSDDDCVSVQHVCTIVSFRSANLVAATLGAILNRLRDNKGTPRLRTTVGVD GSLYKTHPQYSRRFHKTLRRLVPDSDVRFLLSESGSGKGAAMVTAVAYRLAEQHRQIEE TLAHFHLTKDMLLEVKKRMRAEMELGLRKQTHNNAVVKMLPSFVRRTPDGTENGDFLAL DLGGTNFRVLLVKIRSGKKRTVEMHNKIYAIPIEIMQGTGEELFDHIVSCISDFLDYMG IKGPRMPLGFTFSFPCQQTSLDAGILITWTKGFKATDCVGHDVVTLLRDAIKRREEFDL DVVAVVNDTVGTMMTCAYEEPTCEVGLIVGTGSNACYMEEMKNVEMVEGDQGQMCINME WGAFGDNGCLDDIRTHYDRLVDEYSLNAGKQRYEKMISGMYLGEIVRNILIDFTKKGFL FRGQISETLKTRGIFETKFLSQIESDRLALLQVRAILQQLGLNSTCDDSILVKTVCGVV SRRAAQLCGAGMAAVVDKIRENRGLDRLNVTVGVDGTLYKLHPHFSRIMHQTVKELSPK CNVSFLLSEDGSGKGAALITAVGVRLRTEASS |
| NM_021633.2 SEQ ID NO: 2 | >gi\|21361889\|ref\|NM_021633.2\| Homo sapiens kelch-like family member 12 (KLHL12), mRNA | MGGIMAPKDIMTNTHAKSILNSMNSLRKSNTLCDVTLRVEQKDFPAHRIVLAACSDYFC AMFTSELSEKGKPYVDIQGLTASTMEILLDFVYTETVHVTVENVQELLPAACLLQLKGV KQACCEFLESQLDPSNCLGIRDFAETHNCVDLMQAAEVFSQKHFPEVVQHEEFILLSQG EVEKLIKCDEIQVDSEEPVFEAVINWVKHAKKEREESLPNLLQYVRMPLLTPRYITDVI |

TABLE V-continued

Human Hexokinase 1 (HK1) and Human Kelch-Like 12 (KLHL12) Sequences on ProtoArray v.4.0 (Invitrogen, Carlsbad, CA) (Example 1), on the $T^2$-Elisa (several Examples) and on the Conventional ELISA of Example 12

| NCBI Genbank or Protein Accession and SEQ ID NO: | Fasta Header/Description | Sequence |
| --- | --- | --- |
| | | DAEPFIRCSLQCRDLVDEAKKFHLRPELRSQMQGPRTRARLGANEVLLVVGGFGSQQSP IDVVEKYDPKTQEWSFLPSITRKRRYVASVSLHDRIYVIGGYDGRSRLSSVECLDYTAD EDGVNYSVAPMNVRRGLAGATTLGDMIYVSGGFDGSRRHTSMERYDPNIDQWSMLGDMQ TAREGAGLVVASGVIYCLGGYDGLNILNSVEKYDPHTGHWTNVTPMATKRSGAGVALLN DHIYVVGGFDGTAHLSSVEAYNIRTDSWTTVTSMTTPRCYVGATVLRGRLYAIAGYDGN SLLSSIECYDPIIDSWEVVTSMGTQRCDAGVCVLREK |
| | $T^2$ ELISA - Recombinant human HK1 and KLHL12 cell-free expressed in a rabbit reticulocyte lysate. Note that the underlined sequences are exogenously added N-teminal and C-terminal epitope tags as well as vector-derived sequences | |
| CV026580 (EST) SEQ ID NO: 3 | >gi\|51484591\|gb\|CV026580.1\| CV026580 4566 Full Length cDNA from the Mammalian Gene Collection Homo sapiens cDNA 5' similar to BC008730 (HK1), mRNA sequence | <u>MAIYTDIEMNRLGK</u>MIAAQLLAYYFTELKDDQVKKIDKYLYAMRLSDETLIDIMTRFRK EMKNGLSRDFNPTATVKMLPTFVRSIPDGSEKGDFIALDLGGSSFRILRVQVNHEKNQN VHMESEVYDTPENIVHGSGSQLFDHVAECLGDFMEKRKIKDKKLPVGFTFSFPCQQSKI DEAILITWTKRFKASGVEGADVVKLLNKAIKKRGDYDANIVAVVNDTVGTMMTCGYDDQ HCEVGLIIGTGTNACYMEELRHIDLVEGDEGRMCINTEWGAFGDDGSLEDIRTEFDREI DRGSLNPGKQLFEKMVSGMYLGELVRLILVKMAKEGLLFEGRITPELLTRGKFNTSDVS AIEKNKEGLHNAKEILTRLGVEPSDDDCVSVQHVCTIVSFRSANLVAATLGAILNRLRD NKGTPRLRTTVGVDGSLYKTHPQYSRRFHKTLRRLVPDSDVRFLLSESGSGKGAAMVTA VAYRLAEQHRQIEETLAHFHLTKDMLLEVKKRMRAEMELGLRKQTHNNAVVKMLPSFVR RTPDGTENGDFLALDLGGTNFRVLLVKIRSGKKRTVEMHNKIYAIPIEIMQGTGEELFD HIVSCISDFLDYMGIKGPRMPLGFTFSFPCQQTSLDAGILITWTKGFKATDCVGHDVVT LLRDAIKRREEFDLDVVAVVNDTVGTMMTCAYEEPTCEVGLIVGTGSNACYMEEMKNVE MVEGDQGQMCINMEWGAFGDNGCLDDIRTHYDRLVDEYSLNAGKQRYEKMISGMYLGEI VRNILIDFTKKGFLFRGQISETLKTRGIFETKFLSQIESDRLALLQVRAILQQLGLNST CDDSILVKTVCGVVSRRAAQLCGAGMAAVVDKIRENRGLDRLNVTVGVDGTLYKLHPHF SRIMHQTVKELSPKCNVSFLLSEDGSGKGAALITAVGVRLRTEASS<u>LSRELVDPNSVQA RLQDVDGTIDTRSKLAAAQLYTRASQPELAPEDPEDLEHHHHHH</u> |
| BC003183.1 SEQ ID NO: 4 | >gi\|13112018\|gb\|BC003183.1\| Homo sapiens kelch-like 12 (Drosophila), mRNA (cDNA clone MGC:4435 IMAGE:2958852), complete cds | <u>M</u>YTDIEMNRLGKMGGIMAPKDIMTNTHAKSILNSMNSLRKSNTLCDVTLRVEQKDFPAH RIVLAACSDYFCAMFTSELSEKGKPYVDIQGLTASTMEILLDFVYTETVHVTVENVQEL LPAACLLQLKGVKQACCEFLESQLDPSNCLGIRDFAETHNCVDLMQAAEVFSQKHFPEV VQHEEFILLSQGEVEKLIKCDEIQVDSEEPVFEAVINWVKHAKKEREESLPNLLQYVRM PLLTPRYITDVIVAEPFIRCSLQCRDLVLVDEAKKFHLPELRSQMQGPRTRARLGANEVL LVVGGFGSQQSPIDVVEKYDPLTQEWSFLPSITRKRRYVASVSLHDRIYVIGGYDGRSR LSSVECLDYTADEDGVWYSVAPMNVRRGLAGATTLGDMIYVSGGFDGSRRHTSMERYDP NIDQWSMLGDMQTAREGAGLVVASGVIYCLGGYDGLNILNSVEKYDPHTGHWTNVTPMA TKRSGAGVALLNDHIYVVGGFDGTAHLSSVEAYNIRTDSWTTVTSMTTPRCYVGATVLR GRLYAIAGYDGNSLLSSIECYDPIIDSWEVVTSMGTQRCDAGVCVLREK<u>QPELAPEDPE D</u> |
| | Conventional ELISA - Recombinant human HK1 and KLHL12 (Abnova, Taipei City, 114, Taiwan) cell-free expressed in a wheat germ based system. Note that HK1 and KLHL12 contained an N-terminal GST fusion tag (sequence not shown) commonly known to those skilled in the art. | |
| AAH08730 SEQ ID NO: 5 | >gi\|14250554\|gb\|AAH08730.1\| Hexokinase 1 [Homo sapiens] | MIAAQLLAYYFTELKDDQVKKIDKYLYAMRLSDETLIDIMTRFTKEMKNGLSRDFNPTA TVKMLPTFVRSIPDGSEKGDFIALDLGGSSFRILRVQVNHEKNQNVHMESEVYDTPENI VHGSGSQLFDHVAECLGDFMEKRKIKDKKLPVGFTFSFPCQQSKIDEAILITWTKRFKA SGVEGADVVKLLNKAIKKRGDYDANIVAVVNDTNGTMMTCGYDDQHCEVGLIIGTGTNA CYMEELRHIDLVEGDEGRMCINTEWGAFGDDGSLEDIRTEFDREIDRGSLNPGKQLFEK MVSGMYLGELVRLILVKMAKEGLLFEGRITPELLTRGKFNTSDVSAIEKNKEGLHNAKE ILTRLGVEPSDDDCVSVQHVCTIVSFRSANLVAATLGAILNRLRDNKGTPRLRTTVGVD GSLYKTHPQYSRRFHKTLRRLVPDSDVRFLLSESGSGKGAAMVTAVAYRLAEQHRQIEE TLAHFHLTKDMLLEVKKRMRAEMELGLRKQTHNNAVVKMLPSFVRRTPDGTENGDFLAL DLGGTNFRVLLVKIRSGKKRTVEMHNKIYAIPIEIMQGTGEELFDHIVSCISDFLDYMG IKGPRMPLGFTFSFPCQQTSLDAGILITWTKGFKATDCVGHDVVTLLRDAIKRREEFDL DVVAVVNDTVGTMMTCAYEEPTCEVGLIVGTGSNACTMEEMKNVEMVEGDQGQMCINME WGAFGDNGCLDDIRTHYDRLVDEYSLNAGKQRYEKMISGMYLGEIVRNILIDFTKKGFL FRGQISETLKTRGIFETKFLSQIESDRLALLQVRAILQQLGLNSTCDDSILVKTVCGVV SRRAAQLCGAGMAAVVDKIRENRGLDRLNVTVGVDGTLYKLHPHFSRIMHQTVKELSPK CNVSFLLSEDGSGKGAALITAVGVRLRTEASS |
| NP_067646.1 SEQ ID NO: 6 | >gi\|11056006\|ref\|NP_067646.1\| kelch-like protein 12 [Homo sapiens] | MGGIMAPKDIMTNTHAKSILNSMNSLRKSNTLCDVTLRVEQKDFPAHRIVLAACSDYFC AMFTSELSEKGKPYVDIQGLTASTMEILLDFVYTETVHVTVENVQELLPAACLLQLKGV KQACCEFLESQLDPSNCLGIRDFAETHNCVDLMQAAEVFSQKHFPEVVQHEEFILLSQG EVEKLIKCDEIQVDSEEPVFEAVINWVKHAKKEREESLPNLLQYVRMPLLTPRYITDVI DAEPFIRCSLQCRDLVDEAKKFHLRPELRSQMQGPRTRARLGANEVLLVVGGFGSQQSP |

TABLE V-continued

Human Hexokinase 1 (HK1) and Human Kelch-Like 12 (KLHL12) Sequences on ProtoArray v.4.0 (Invitrogen, Carlsbad, CA) (Example 1), on the $T^2$-Elisa (several Examples) and on the Conventional ELISA of Example 12

| NCBI Genbank or Protein Accession and SEQ ID NO: | Fasta Header/Description | Sequence |
|---|---|---|
| | | IDVVEKYDPKTQEWSFLPSITRKRRYVASVSLHDRIYVIGGYDGRSRLSSVECLDYTAD EDGVWYSVAPMNVRRGLAGATTLGDMIYVSGGFDGSRRHTSMERYDPNIDQWSMLGDMQ TAREGAGLVVASGVIYCLGGYDGLNILNSVEKYDPHTGHWTNVTPMATKRSGAGVALLN DHIYVVGGFDGTAHLSSVEAYNIRTDSWTTVTSMTTPRCYVGATVLRGRLYAIAGYDGN SLLSSIECYDPIIDSWEVVTSMGTQRCDAGVCVLREK |

TABLE VI

Example of Homologous Sequences for HK1 and KLH12

| NCBI Protein Accession (Gene Nmae) SEQ ID NO: | Fasta Header/Description | Sequence |
|---|---|---|
| HEXOKINASE 1 and Homologs | | |
| NP_277031.1 (HK1) SEQ ID NO: 7 | >gi\|15991827\|ref\| NP_2777031.1\|hexokinase-1 isoform HKI-R [Homo sapiens] | MDCEHSLSLPCRGAEAWEIGIDKYLYAMRLSDETLIDIMTRFRKEMKNGLSRDFNPTATVK MLPTFVRSIPDGSEKGDFIALDLGGSSFRILRVQVNHEKNQNVHMESEVYDTPENIVHGSG SQLFDHVAECLGDFMEKRKIKDKKLPVGFTFSFPCQQSKIDEAILITWTKRFKASGVEGAD VVKLLNKAIKKRGDYDANIVAVVNDTVGTMMTCGYDDQHCEVGLIIGTGTNACYMEELRHI DLVEGDEGRMCINTEWGAFGDDGSLEDIRTEFDREIDRGSLNPGKQLFEKMVSGMYLGELV RLILVKAMKEGLLFEGRITPELLTRGKFNTSDVSAIEKNKEGLHNAKEILTRLGVEPSDDD CVSVQHVCTIVSFRSANLVAATLGAILNRLRDNKGTPRLRTTVGVDGSLYKTHPQYSRRFH KTLRRLVPDSDVRFLLSESGSGKGAAMVTAVAYRLAEQHRQIEETLAHFHLTKDMLLEVKK RMRAEMELGLRKQTHNNAVVKMLPSFVRRTPDGTENGDFLALDLGGTNFRVLLVKIRSGKK RTVEMHNKIYAIPIRIMQGTGEELFDHIVSCISDFLDYMGIKGPRMPLGFTFSFPCQQTSL DAGILITWTKGFKATDCVGHDVVTLLRDAIKRREEFDLDVVAVVNDTVGTMMTCAYEEPTC EVGLIVGTGSNACYMEEMKNVEMVEGDQGQMCINMEWGAFGDNGCLDDIRTHYDRLVDEYS LNAGKQRYEKMISGMYLGEIVRNILIDFTKKGFLFRGQISETLKTRGIFETKFLSQIESDR LALLQVRAILQQLGLNSTCDDSILVKTVCGVVSRRAAQLCGAGMAAVVDKIRENRGLDRLN VTVGVDGTLYKLHPHFSRIMHQTVKELSPKCNVSFLLSEDGSGKGAALITAVGVRLRTEAS S |
| NP_000180.2 (HK2) SEQ ID NO: 8 | >gi\|15553127\|ref\| NP_000180.2\|hexokinase-2 [Homo sapiens] | MIASHLLAYFFTELNHDQVQKVDQYLYHMRLSDETLLEISKRFRKEMEKGLGATTHPTAAV KMLPTFVRSTPDGTEHGEFLALDLGGTNFRVLQVKVTDNGLQKVEMENQIYAIPEDIMRGS GTQLFDHIAECLANFMDKLQIDKKLPLGFTFSFPCHQTKLDESFLVSWTKGFKSSGVEGR DVVALIRKAIQRRGDFDIDIVAVVNDTVGTMMTCGYDDHNCEIGLIVGTGSNAOYMEEMRH IDMVEGDEGRMCINMEWGAFGDDGSLNDIRTEFDQEIDMGSLNPGKQLFEKMISGMYMGEL VRLILVKMAKEELLFGGKLSPELLNTGRFETDISDIEGEKDGIRKAREVLMRLGLDTPTQE DCVATHRICQIVSTRSASLCAATLAAVLQRIKENKGEERLRSTIGVDGSVYKKHPFAKRL HKTVRRLVPGCDVRFLRSEDGSGKGAAMVTAVAYRLADQHRARQKTLEHLQLSHDQLLEVK RRMKVEMERGLSKETHASAPVKMLPTYVCATPDGTEKGDFLALDLGGTNFRVLLVRVRNGK WGGVEMHNKIYAIPQEVMHGTGDELFDHIVQCIADFLEYMGMKGVSLPLGFTSFPCQQNS LDESILLKWTKGFKASGCEGEDVVTLLKEAIHRREEFDLDVVAVVNDTVGTMMTCGFEDPH CEVGLIVGTGSNACYMEEMRNVELVEGEEGRMCVNMEWGAFGDNGCLDDFRTEFDVAVDEL SLNPGKQRFEKMISGMYLGEIVRNILIDFTKRGLLFRGRISERLKTRGIFETKFLSQIESD CLALLQVRAILQHLGLESTCDDSIIVKEVCTVVARRAAQLCGAGMAAVVDRIRENRGLDAL KVTVGVDGTLYKLHPHFAKVMHETVKDLAPKCDVSFLQSEDGSGKGAALITAVACRIREAG QR |
| NP_002106.2 (HK3) SEQ ID NO: 9 | >gi\|194097330\|ref\| NP_002106.2\|hexokinase-3 [Homo sapiens] | MDSIGSSGLRQGEETLSCSEEGLPGPSDSSELVQECLQQFKVTRAQLQQIQASLLGSMEQA LRGQASPAPAVRMLPTYVGSTPHGTEQGDFVVLELGATGASLRVLWVTLTGIEGHRVEPRS QEFVIPQEVMLGAGQQLFDFAAHCLSEFLDAQPVNKQGLQLGFSFSFPCHQTGLDRSTLIS WTKGFRCSGVEGQDVVQLLRDAIRRQGAYNIDVVAVVNDTVGTMMGCEPGVRPCEVGLVVD TGTNACYMEEARHVAVLDEDRGVCVSVEWGSFSDDGALGPVLTTFDHTLDHESLNPGAQR FEKMIGGLYLGELVRLVLAHLARCGVLFGGCTSPALLSQGSILLEHVAEMEDPSTGAARVH AILQDLGLSPGASDVELVQHCVCAAVCTRAAQLCAAALAAVLSCLQHSREQQTLQVAVATGG RVCERHPRFCSVLQGTVMLLAPECDVSLIPSVDGGGRGVAMVTAVAARLAAHRRLLEETLA PFRLNHDQLLAVQAQMRKAMAKGLRGEASSLRMLPTFVRATPDGSERGDFLALDLGGTNFR VLLVRVTTGVQITSEIYSIPETVAQGSGQQLFDHIVDCIVDFQQKQGLSGQSLPLGFTFSF PCRQLGLDQGILLNWTKGFKASDCEGQDVVSLLREAITRRQAGVNLNVVAIVNDTVGTMMSC GYEDPRCEIGLIVGTGTNACYMEELRNVAGVPGDSGRMCINMEWGAFGDRGSLAMLSTRFD ASVDQASINPGKQRFEKMISGMYLGEIVRHILLHLTSLGVLFRGQQIQRLQTRDIFKTKFL SEIESDSLALRQVRAILEDLGLPLTSDDALMVLEVCQAVSQRAAQLCGAGVAAVVEKIREN RGLEELAVSVGVDGTLYKLHPRFSSLVAATVRELAPRCVVTFLQSEDGSGKGAALVTAVAC RLAQLTRV |

TABLE VI-continued

Example of Homologous Sequences for HK1 and KLH12

| NCBI Protein Accession (Gene Name) SEQ ID NO: | Fasta Header/Description | Sequence |
|---|---|---|
| NP_277042.1 (HK4) SEQ ID NO: 10 | >gi\|15967159\|ref\| NP_277042.1\|glucokinase isoform 2 [Homo sapiens] | MAMDVTRSQAQTALTLVEQILAEFQLQEEDLKKVMRRMQKEMDRGLRLETHEEASVKMLPT YVRSTPEGSEVGDFLSLDLGGTNFRVMLVKVGEGEEGQWSVKTKHQMYSIPEDAMTGTAEM LFDYISECISDFLDKHQMKHKKLPLGFTFSFPVRHEDIDKGILLNWTKGFKASGAEGNNVV GLLRDAIKRRGDFEMDVVAMVNDTVATMISCYYEDHQCEVGMIVGTGCNACYMEEMQNVEL VEGDEGRMCVNTEWGAFGDSGELDEFLLEYDRLVDESSANPGQQLYEKLIGGKYMGELVRL VLLRLVDENLLFHGEASEQLRTRGAFETRFVSQVESDTGDTKQIYNILSTLGLRPSTTDCD IVRRACESVSTRAAHMCSAGLAGVINRMRESRSEDVMRITVGVDGSVYKLHPSFKERFHAS VRRLTPSCEITFIESEEGSRGAALVSAVACKKACMLGQ |
| NP_079406.3 (HKDC1) SEQ ID NO: 11 | >gi\|156151420\|ref\| NP_079406.3\| putative hexokinase HKDC1 [Homo sapiens] | MFAVHLMAFYFSKLKEDQIKKVDRFLYHMRLSDDTLLDIMRRFRAEMEKGLAKDTNPTAAV KMLPTFVRAIPDGSENGEFLSLDLGGSKFRVLKVQVAEEGKRHVQMESQFYPTPNEIIRGN GTELFEYVADCLADFMKTKDLHKKLPLGLTFSFPCRQTKLEEGVLLSWTKKFKARGVQDT DVVSRLTKAMRRHKDMDVDILALVNDTVGTMMTCAYDDPYCEVGIIGTGTNACYMEDMSN IDLVEGDEGRMCINTEWGAFGDNGALEDIRTEFDRELDLGSLNPGKQLFEKMISGLYLGEL VRLILLKMAKAGLLFGGEKSSALHTKGKIETRHVAAMEKYKEGLANTREILVDLGLEPSEA DCIAVQHVCTIVSFRSANLCAAALAAILTRLRENKKVERLRTTVGMDGTLYKIHPQYPKRL HKVVRKLVPSCDVRFLLSESGSTKGAAMVTAVASRVQAQRKQIDRVLALFQLTREQLVDVQ AKMRAELEYGLKKKSHGLATVRMLPTYVCGLPDGTEKGKFLADLGGTNFRVLLVKIRSGR RSVRMYNKIFAIPLEIMQGTGEELFDHIVQCIADFLDYMGLKGASLPLGFRFSFPCRQMSI DKGTLIGWTKGFKATDCEGEDVVDMLREAIKRRNEFDLDIVAVVNDTVGTMMTCGYEDPNC EIGLIAGTGSNMCYMEDMRNIEMVEGGEGKMCINTEWGGFGDNGCIDDIRTRYDTEVDEGS LNPGKQRYEKMTSGMYLGEIVRQILIDLTKQGLLFRGQISERLRTRGIFETKFLSQIESDR LALLQVRRILQQLGLDSTCEDSIVVKEVCGAVSRRAAQLCGAGLAAIVEKRREDQGLEHLR ITVGVDGTLYKLHPHFSRILQETVKELAPRCDVTFMLSEDGSGKGAALITAVAKRLQQAQK EN |

KELCH-LIKE 12 and Homologs

| NCBI Protein Accession (Gene Name) SEQ ID NO: | Fasta Header/Description | Sequence |
|---|---|---|
| NP_0676446.1 (KLHL12) SEQ ID NO: 12 | >gi\|11056006\|ref\| NP_067646.1\|kelch-like protein 12 [Homo sapiens] | MGGIMAPKDIMTNTHAKSILNSMNSLRKSNTLCDVTLRVEQKDFPAHRIVLAACSDYFCAM FTSELSEKGKPYVDIQGLTASTMEILLDPVYTETVHVTVENVQELLPAACLLQLKGVKQAC CEFLESQLDPSNCLGIRDFAETHNCVDLMQAAEVFSQKHFPEVVQHEEFILLSQGEVEKLI KCDEIQVDSEEPVFEAVINWVKHAKKEREESLPNLLQYVRMPLLTPRYITDVIDAEPFIRC SLQCRDLVDEAKKFHLRPELRSQMQGPRTRARLGANEVLLVVGGFGSQQSPIDVVEKYDPK TQEWSFLPSITRKRRYVASVSLHDRIYVIGGYDGRSTLSSVECLDYTADEDGVWYSVAPMN VRRGLAGATTLGDMIYVSGGFDGSRRHTSMERYDPNIDQWSMLGDMQTAREGAGLVVASGV IYCLGGYDGLNILNSVEKYDPHTGHWTNVTPMATKRSGAGVALLNDHIYVVGGFDGTAHLS SVEAYNIRTDSWTTVTSMTTPRCYVGATVLRGRLYAIAGYDGNSLLSSIECYDPIIDSWEV VTSMGTQRCDAGVCVLREK |
| NP_055273.2 (KLHL20) SEQ ID NO: 13 | >gi\|40807500\|ref\| NP_055273.2\|kelch-like protein 20 [Homo sapiens] | MEGKPMRRCTNIRPGETGMDVTSRCTLGDPNKLPEGVPQPARMPYISDKHPRQTLEVINLL RKHRELCDVVLVVGAKKIYAHRVILSACSPYFRAMFTGELAESRQTEVVIRDIDERAMELL IDFAYTSQITVEEGNVQTLLPAACLLQLAEIQEACCEFLKRQLDPSNCLGIRAFADTHSCR ELLRIADKFTQHNFPQEVMESEEFMLLPANQLIDIISSDELNVRSEEQVFNAVMAWVKYSIQ ERRPQLPQVLQHVRLPLLSPKFLVGTVGSDPLIKSDEECRDLVDEAKNYLLLPQERPLMQG PRTRPRKPIRCGEVLFAVGGWCSGDAISSVERYDPQTNEWRMVASMSKRRCGVGVSVLDDL LYAVGGHDGSSYLNSVERYDPKTNQWSSDVAPTSTCRTSVGVAVLGGFLYAVGGQDGVSCL NIVERYDPKENKWTRVASMSTRRLGVAVAVLGGFLYAVGGSDGTSPLNTVERYNPQENRWH TIAPMGTRRKHLGCAVYQDMIYAVGGRDDTELSSAERYNPRTNQWSPVVAMTSRRSGVGL AVVNGQLMAVGGFDGTTYLKTIEVFDPDANTWRLYGGMNYRRLGGGVGVIKMTHCESHIW |
| NP_059111.2 (KLHL3) SEQ ID NO: 14 | >gi\|166235129\|ref\| NP_059111.2\|kelch-like protein 3 isoform 1 [Homo sapiens] | MEGESVKLSSQTLIQAGDDEKNDRTITVNPAHMGKAFKVMNELRSKQLLCDVMIVAEDVEI EAHRVVLAACSPYFCAMFTGDMSESKAKKIEIKDVDGQTLSKLIDYIYTAEIEVTEENVQV LLPAASLLQLMDVRQNCCDFLQSQLHPTNCLGIRAFADVHTCTDLLQQANAYAEQHFPEVM LGEEFLSLSLDQVCSLISSDKLTVSSEEKVFEAVISWINYEKETRLEHMAKLMEHVRLPLL PRDYLVQTVEEEALIKNNNTCKDFLIEAMKYHLLPLDQRLLIKNPRTKPRTPVSLPKVMIV VGGQAPKAIRSVECYDFEEDRWDQIAELPSRRCRAGVVFMAGHVYAVGGFNFSLRVRTVDV YDGVKDQWTSIASMQERRSTLGAAVLNDDLLYAVGGFDGSTGLASVEAYSYKTNEWFFVAPM NTRRSSVGVGVVEGKLYAVGGYDGASRQCLSTVEQYNPATNEWIYVADMSTRRSGAGVGVL SGQLYATGGHDGPLVRKSVEVYDPGTNTWKQVADMNMCRRNAGVCAVNGLLYVVGGDDGSC NLASVEYYNPVTDKWTLLPTNMSTGRSYAGVAVIHKSL |
| NP_938073.1 (KLHL17) SEQ ID NO: 15 | >gi\|38194229\|ref\| NP_938073.1\|kelch-like protein 17 [Homo sapiens] | MQPRSERPAGRTQSPEHGSPGPGPEAPPPPPPQPPAPEAERTRPRQARPAAPMEGAVQLLS REGHSVAHNSKRHYHDAFVAMSRMRQRGLLCDIVLHVAAKEIRAHKVVLASCSPYFHAMFT NEMSESRQTHVTLHDIDPQALDQLVQFAYTAEIVVGEGNVQTLLPAASLLQLNGVRDACCK FLLSQLDPSNCLGIRGFADAHSCSDLLKAAHRYVLQHFVDVAKTEEFMLLPLKQVLELVSS DSLNVPSEEEVYRAVLSWVKHDVDARRQHVPRLMKCVRLPLLSRDFLLGHVDAESLVRHHP DCKDLLIEALKFHLLPEQRGVLGTSRTRPRRCEGAGPVLFAVGGSLFAIHGDCEAYDTRT DRWHVASMSTRRARVGVAAVGNRLYAVGGYDGTSDLATVESYDPVTNTWQPEVSMGTRRS CLGVAALHGLLYSAGGYDGASCLNSAERYDPLTGTWTSVAAMSTRRRYVRVATLDGNLYAV GGYDSSSHLATVEKYEPQVNVWSPVASMLSRRSSAGVAVLEGALYVAGGNDGTSCLNSVER YSPKAGAWESVAPMNIRRSTHDLVAMDGWLYAVGGNDGSSSLNSIEKYNPRTNKWVAASCM FTRRSSVGVAVLELLNFPPPSSPTLSVSSTSL |

TABLE VI-continued

Example of Homologous Sequences for HK1 and KLH12

| NCBI Protein Accession (Gene Nmae) SEQ ID NO: | Fasta Header/Description | Sequence |
|---|---|---|
| NP_001154993.1 (KLHL2 isoform 2) SEQ ID NO: 16 | >gi\|239835722\|ref\| NP_001154993.1\| kelch-like protein 2 isoform 2 [Homo sapiens] | MVWLEARPQILFVCTKQGHQKPLDSKDDNTEKHCPVTVNPWHMKKAFKVMNELRSQNLLCD VTIVAEDMEISAHRVVLAACSPYFHAMFTGEMSESRAKRVRIKEVDGWTLRMLIDYVYTAE IQVTEENVQVLLPAAGLLQLQDVKKTCCEFLESQLHPVNCLGIRAFADMHACTDLLNKANT YAEQHFADVVLSEEFLNLGIEQVCSLISSDKLTISSEEKVFEAVIAWVNHDKDVRQEFMAR LMEHVRLPLLPREYLVQRVEEEALVKNSSACKDYLIEAMKYHLLPTEQRILMKSVRTRLRT PMNLPKLMVVVGGQAPKAIRSVECYDFKEERWHQVAELPSRRCRAGMVYMAGLVFAVGGFN GSLRVRTVDSYDPVKDQWTSVANMRDRRSTLGAAVLNGLLYAVGGFDGSTGLSSVEAYNIK SNEWFHVAPMNTRRSSVGVGVVGGLLYAVGGYDGASRQCLSTVECYNATTNEWTYIAEMST RRSGAVGVGLNNLLYAVGGHDGPLVRKSVEVYDPTTNAWRQVADMNMCRRNAGVCAVNGLL YVVGGDDGSCNLASVEYYNPTTDKWTVVSSCMSTGRSYAGVTVIDKPL |
| NP_009177.3 (KLHL2 isoform 1) SEQ ID NO: 17 | >gi\|239835720\|ref\| NP_009177.3\| kelch-like protein 2 isoform 1 [Homo sapiens] | METPPLPPACTKQGHQKPLDSKDDNTEKHCPVTVNPWHMKKAFKVMNELRSQNLLCDVTIV AEDMEISAHRVVLAACSPYFHAMFTGEMSESRAKRVRIKEVDGWTLRMLIDYVYTAEIQVT EENVQVLLPAAGLLQLQDVKKTCCEFLESQLHPVNCLGIRAFADMHACTDLLNKANTYAEQ HFADVVLSEEFLNLGIEQVCSLISSDKLTISSEEKVFEAVIAWVNHDKDVRQEFMARLMEH VRLPLLPREYLVQRVEEEALVKNSSACKDYLIEAMKYHLLPTEQRILMKSVRTRLRTPMNL PKLMVVVGGQAPKAIRSVECYDFKEERWHQVAELPSRRCRAGMVYMAGLVFAVGGFNHSLR VRTVDSYDPVKDQWTSVANMRDRRSTLGAAVLNGLLYAVGGFDGSTGLSSVEAYNIKSNEW FHVAPMNTRRSSVGVGVVGGLLYAVGGYDGASRQCLSTVECYNATTNEWTYIAEMSTRRSG AGVGVGLNNLLYAVGGHDGPLVRKSVEVYDPTTNAWRQVADMNMCRRNAGVCAVNGLLYVVG GDDGSCNLASVEYYNPTTDKWTVVSSCMSTGRSYAGVTVIDKPL |
| NP_079286.2 (KLHL18) SEQ ID NO: 18 | >gi\|55925604\|ref\| NP_079286.2\|kelch-like protein 18 [Homo sapiens] | MVEDGAEELEDLVHFSVSELPSRGYGVMEEIRRQGKLCDVTLKIGDHKFSAHRIVLAASIP YFHAMFTNDMMECKQDEIVMQGMDPSALEALINFAYNGNLAIDQQNVQSLLMGASFLQLQS IKDACCTFLRERLHPKNCLGVRQFAETMMCAVLYDAANSFIHQHFVEVSMSEEFLALPLED VLELVSRDELNVKSEEQVFEAA;AWVRYDREQRGPYLPELLSNIRLPLCRPQFLSDRVQQD DLVRCCHKCRDLVDEAKDYHLMPERRPHLPAFRTRPRCCTSIAGLIYAVGGLNSAGDSLNV VEVFDPIANCWERCRPMTTARSRVGAVVNGLLYAIGGYDGQLRLSTVEAYNPETDTWTRV GSMNSKRSAMGTVVLDGQIYVCGGYDGNSSLSSVETYSPETDKWTVVTSMSSNRSAAGVTV FEGRIYVSGGHDGLQIFSSVEHYNHHTATWHPAAGMLNKRCRHGAASLGSKMFVCGGYDGS GFLSIAEMYSSVADQWCLIVPMHTRRSRVSLVASCGRLYAVGGYDGQSNLSSVEMYDPETD CWTFMAPMACHEGGVGVGCIPLLTI |

What is claimed is:

1. A method of diagnosing primary biliary cirrhosis (PBC) comprising:
   a. contacting a test sample from an individual suspected of having PBC with one or more purified recombinant target antigens of hexokinase 1 comprising SEQ ID NO: 1 or a homologous sequence of hexokinase 1, comprising a sequence selected from the group consisting of SEQ ID NOS. 7, 8 and 11;
   b. detecting binding of the one or more purified recombinant target antigens to one or more autoantibodies specific for the one or more purified recombinant target antigens in the test sample; and
   c. comparing the level of autoantibodies to a control; wherein an increased level of the one or more autoantibodies bound to the one or more purified recombinant target antigens as compared to a threshold level of hexokinase 1 or a homologous sequence of hexokinase 1 autoantibodies obtained from a healthy individual is indicative of primary biliary cirrhosis.

2. The method of claim 1, wherein the one or more purified recombinant target antigens are immobilized on a solid support.

3. The method of claim 1, wherein the test sample is contacted with two or more of the purified recombinant target antigens.

4. The method of claim 1, wherein the test sample is contacted with three or more of the purified recombinant target antigens.

5. The method of claim 1, wherein the test sample is contacted with four or more of the purified recombinant target antigens.

6. The method of claim 1, wherein the test sample is cells, tissues or body fluids.

7. The method of claim 1, wherein the test sample is blood, plasma or serum.

8. The method of claim 1, wherein the one or more purified recombinant target antigens are produced using cell-free protein expression.

9. The method of claim 1, wherein the one or more purified recombinant target antigens further comprises a tag sequence located at the C-terminal or N-terminal, or at both the C-terminal and N-terminal.

10. The method of claim 1, wherein the detection step further comprises a labeled anti-immunoglobulin (IG) antibody and wherein the one or more purified recombinant target antigen, autoantibody, and anti-IG antibody form a complex.

11. The method of claim 2, wherein the one or more purified recombinant target antigens further comprises a tag sequence located at the C-terminal, N-terminal, or at both the C-terminal and N-terminal.

12. The method of claim 11, wherein the one or more purified recombinant target antigens are immobilized on the solid support using the tag sequence.

* * * * *

UNITED STATES PATENT AND TRADEMARK OFFICE
CERTIFICATE OF CORRECTION

PATENT NO. : 8,852,956 B2  
APPLICATION NO. : 13/500411  
DATED : October 7, 2014  
INVENTOR(S) : Mark J. Lim et al.

Page 1 of 1

It is certified that error appears in the above-identified patent and that said Letters Patent is hereby corrected as shown below:

On the Title page, left column, item (75) please delete "Ostendorf" and replace therefore with -- Ostendorff --.

In the Claims

At column 107, line 2, please delete the phrase "or more.".

Signed and Sealed this  
Twenty-third Day of June, 2015

Michelle K. Lee  
*Director of the United States Patent and Trademark Office*